(12) United States Patent
Konishi et al.

(10) Patent No.: US 10,000,743 B2
(45) Date of Patent: Jun. 19, 2018

(54) 2-DEOXY-SCYLLO-INOSOSE REDUCTASE

(71) Applicant: Asahi Kasei Chemicals Corporation, Tokyo (JP)

(72) Inventors: Kazunobu Konishi, Tokyo (JP); Nobuya Itoh, Toyama (JP); Junji Kurokawa, Toyama (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days. days.

(21) Appl. No.: 14/914,500

(22) PCT Filed: Dec. 5, 2014

(86) PCT No.: PCT/JP2014/082244
§ 371 (c)(1),
(2) Date: Feb. 25, 2016

(87) PCT Pub. No.: WO2015/093320
PCT Pub. Date: Jun. 25, 2015

(65) Prior Publication Data
US 2016/0208224 A1 Jul. 21, 2016

(30) Foreign Application Priority Data
Dec. 16, 2013 (JP) .................................. 2013-259354

(51) Int. Cl.
| | |
|---|---|
| *C12P 7/02* | (2006.01) |
| *C12N 1/21* | (2006.01) |
| *C12N 9/04* | (2006.01) |
| *C12N 15/53* | (2006.01) |
| *C12N 9/02* | (2006.01) |
| *C12P 7/18* | (2006.01) |

(52) U.S. Cl.
CPC ......... *C12N 9/0006* (2013.01); *C12N 9/0008* (2013.01); *C12P 7/02* (2013.01); *C12P 7/18* (2013.01); *C12Y 101/01018* (2013.01); *C12Y 101/01329* (2015.07)

(58) Field of Classification Search
None
See application file for complete search history.

(56) References Cited

U.S. PATENT DOCUMENTS

| | | | |
|---|---|---|---|
| 2006/0240534 A1* | 10/2006 | Yamaguchi .......... | C12N 9/0006 435/131 |
| 2007/0075289 A1 | 4/2007 | Egawa et al. | |

FOREIGN PATENT DOCUMENTS

| | | |
|---|---|---|
| JP | H11-12210 A | 1/1999 |
| JP | 2000-004890 A | 1/2000 |
| JP | 2005-000070 A | 1/2005 |
| JP | 2005-000072 A | 1/2005 |
| JP | 2010-215876 A | 9/2010 |
| WO | 2005/091413 A1 | 9/2005 |

OTHER PUBLICATIONS

Wahl et al., Molecular Hybridization of Immobilized Nucleic Acids: Theoretical Concepts and Practical Considerations, Methods Enz., 1987, 152, 399-407.*
GenBank, Accession No. CP001013, 2011, www.ncbi.nih.gov.*
GenBank, Accession No. AJHK02000012, 2012, www.ncbi.nlm.nih.gov.*
Uniprot, Accession No. K8RK49, 2013, www.uniprot.org.*
Guo et al., Protein tolerance to random amino acid change, Proc. Natl. Acad. Sci. USA, 2004, 101, 9205-10.*
Wahl et al., Molecular Hybridization of Immobilized Nucleic Acids: Theoretical Concepts and Practical Considerations, Methods Enz ., 1987, 152, 399-407.*
Daniellou et al., Stereoselective oxidation of protected inositol derivatives catalyzed by inositol dehydrogenase from Bacillus subtilis , Org. Biomol. Chem., 2005, 3, 401-03.*
GenBank, Accession No. ADU72508, 2011, www.ncbi.nlm.nih.gov.*
Itoh et al., Identification and characterization of a novel (−)-vibo-quercitol 1-dehydrogenase from Burkholderia terrae suitable for production of (−)-vibo-quercitol from 2-deoxy-scyllo-inosose, Appl, Microbiol. Biotechnol., 2017, 101, 7545-55.*
Database UniProtKB/TrEMBL, [online], Accession No. K8RK49 (2013).
Database UniProtKB/TrEMBL, [online], Accession No. E6WM73 (2013).
Database UniProtKB/TrEMBL, [online], Accession No. I4KWR4 (2013).
Database UniProtKB/TrEMBL, [online], Accession No. I4KGN5 (2013).
"inositol 2-dehydrogenase [Pseudomonas synxantha]," NCBI GenBank accession No. WP_005787932 (2013).
"inositol 2-dehydrogenase [*Burkholderia* sp. SJ98]," NCBI GenBank accession No. WP_008348849 (2013).
inositol 2-dehydrogenase [*Pantoea* sp. At-9b], NCBI GenBank accession No. WP_013512337 (2013).
Office Action issued in related Taiwanese Patent Application No. 103143451 dated Jan. 25, 2016.
International Search Report issued in corresponding International Patent Application No. PCT/JP2014/082244 dated Mar. 10, 2015.
Office Action issued in counterpart Chinese Patent Application No. 201480048371.5 dated Mar. 28, 2017.
inositol 2-dehydrogenase [*Acidiphillum* sp. PM], NCBI Reference Sequence: WP_007421624.1 (2013).

* cited by examiner

*Primary Examiner* — Robert B Mondesi
*Assistant Examiner* — Todd M Epstein
(74) *Attorney, Agent, or Firm* — Morgan, Lewis & Bockius LLP

(57) ABSTRACT

The disclosure provides 2-deoxy-scyllo-inosose reductases derived from a microorganism having the ability to utilize (−)-vibo-quercitol, recombinant vectors and transformants comprising genes encoding the same, and methods of use thereof.

16 Claims, 14 Drawing Sheets

FIG. 1

*Pseudomonas abietaniphila* AKC-019
<Identities = 647/653 (99%), Gaps = 5/653 (0%)>
TACTTTGACGGCAGGTCTACACATGCAGTCGAGCGGATGAGGGAGCTTGCTCCCTGATTCAGCGGCGGA
CGGGTGAGTATGCCTAGGAATCTGCCTGGTAGTGGGGGACAACGTCTCGAAAGGGACGCTAATACCGC
ATACGTCCTACGGGAGAAAGTGGGGGATCTTCGGACCTCACGCTATCAGATGAGCCTAGGTCGGATTA
GCTAGTTGGTGAGGTAATGGCTCACCAAGGCGACGATCCGTAACTGGTCTGAGAGGATGATCAGTCAC
ACTGGAACTGAGACACGGTCCAGACTCCTACGGGAGGCAGCAGTGGGGAATATTGGACAATGGGCGA
AAGCCTGATCCAGCCATGCCGCGTGTGTGAAGAAGGTCTTCGGATTGTAAAGCACTTTAAGTTGGGAGG
AAGGGCATTAACCTAATACGTTAGTGTTTTGACGTTACCGACAGAATAAGCACCGGCTAACTCTGTGCCA
GCAGCCGCGGTAATACAGAGGGTGCAAGCGTTAATCGGAATTACTGGGCGTAAAGCGCGCGTAGGTG
GTTTGTTAAGTTGAATGTGAAATCCCCGGGCTCAACCTGGGAACTGCATCCAAACTGGCAAGCTAGAGT
AGGGCAGAGGGTGGTGGAATTTCCTGTGTAGCGGTGAAATG (SEQ ID NO: 74)

*Burkholderia terrae* AKC-020
<Identities = 567/579 (98%), Gaps = 11/579 (1%)>
TTCTTGGGCGGCTGCCTTCCATGCAGTCGACGGCAGCGCGGGGGCACCCTGGCGGCGAAGTGGCGAAC
GGGTGAGTATACATCGGACGTGTCCTGGAGTGGGGGATAGCCCGGCGAAAGCCGGATTAATACCGCAT
ACGATCCTGGGATGAAAGCGGGGGACCGAAAGGCCTCGCGCTCAAGGGGCGGCCGATGGCAGATTAG
CTAGTTGGTGGGGTAAAGGCCTACCAAGGCGACGATCTGTAGCTGGTCTGAGAGGACGACCAGCCACA
CTGGGACTGAGACACGGCCCAGACTCCTACGGGAGGCAGCAGTGGGGAATTTTGGACAATGGGGGCA
ACCCTGATCCAGCAATGCCGCGTGTGTGAAGAAGGCCTTCGGGGTTGTAAAGCACTTTTGTCCGGAAAG
AAAACCTCCGTCCTAATACGGTGGGGGGGATGACGGTACCGGAAGAATAAGCACCGGCTAACTACGTG
CCAGCAGCCGCGGTAATACGTAGGGTGCAAGCGTTAATCGGAATTACTGGGCGTAAAGCGTGCGCAGG
CGGTTCGCTAAGACCGATGTGAAATCCCCGGGCT (SEQ ID NO: 75)

*Pseudomonas sp.*
GACCTGGGCGGCAGGCCTAACCATGCAGTCGAGCGGATGACAGGAGCTTGCTCCTGATTCAGCGGCGG
ACGGGTGAGTATGCCTAGGAATCTGCCTGGTAGTGGGGGACAACGTTTCGAAAGGAACGCTAATACCG
CATACGTCCTACGGGAGAAAGCAGGGGACCTTCGGGCCTTGCGCTATCAGATGAGCCTAGGTCGGATT
AGCTAGTTGGTGAGGTAATGGCTCACCAAGGCGACGATCCGTAACTGGTCTGAGAGGATGATCAGTCA
CACTGGAACTGAGACACGGTCCAGACTCCTACGGGAGGCAGCAGTGGGGAATATTGGACAATGGGCG
AAAGCCTGATCCAGCCATGCCGCGTGTGTGAAGAAGGTCTTCGGATTGTAAAGCACTTTAAGTTGGGAG
GAAGGGCAGTAAATTAATACTTTGCTGTTTTGACGTTACCGACAGAATAAGCACCGGCTAACTCTGTGCC
AGCAGCCGCGGTAATACAGAGGGTGCAAGCGTTAATCGGAATTACTGGGCGTAAAGCGCGCGTAGGTG
GTTTGT (SEQ ID NO: 76)

Figure 1 –continued

*Pseudomonas sp.*
CACCCTTGGCGCAGGTCTACACATGCAGTCGAGCGGCAGCCGGGTACTTGTACCTGGTGGCGAGCGGC
GGACGGGTGAGTATGCCTAGGATCTGCCTGGTAGTGGGGGATGACGTTCGGAAACGAACGCTAATACC
GCATACGTCCTACGGGAGAAGCAGGGGACCTTCGGGCCTTGCGCTATCAGATGAGCCTAGGTCGGATT
AGCTAGTTGGTGAGGTAATGGCTCACCAAGGCGACGATCCGTAACTGGTCTGAGAGGATGATCAGTCA
CACTGGAACTGAGACACGGTCCAGACTCCTACAGGAGGCAGCAGTGGGGAATATTGGACAATGGGCGA
AAGCCTGATCCAGCCATGCCGCGTGTGTGAAGAAGGTCTTCGGATTGTAAAGCACTTTAAGTTGGGAGG
AAGGGCAGTTACCTAATACGTGATTGTTTTGACGTTACCGACAGAATAAGCACCGGCTAACTCTGTGCCA
GCAGCCGCGGTAATACAGAGGGTGCAAGCGTTAATCGGAATTACTGGGCGTAAAGCGCGCGTAGGTG
GTTCG (SEQ ID NO: 77)

*Pseudomonas sp.*
GCCTGGGCGCAGGTCTACCATGCAGTCGAGCGGCAGCACGGGTACTTGTACCTGGTGGCGAGCGGCGG
ACGGGTGAGTAATGCCTAGGAATCTGCCTGGTAGTGGGGGATAACGTTCGGAAACGAACGCTAATACC
GCATACGTCCTACGGGAGAAAGCAGGGGACCTTCGGGCCTTGCGCTATCAGATGAGCCTAGGTCGGAT
TAGCTAGTTGGTGAGGTAATGGCTCACCAAGGCGACGATCCGTAACTGGTCTGAGAGGATGATCAGTC
ACACTGGAACTGAGACACGGTCCAGACTCCTACGGGAGGCAGCAGTGGGGAATATTGGACAATGGGC
GAAAGCCTGATCCAGCCATGCCGCGTGTGTGAAGAAGGTCTTCGGATTGTAAAGCACTTTAAGTTGGGA
GGAAGGGCAGTTACCTAATACGTGATTGTTTTGACGTTACCGACAGAATAAGCACCGGCTAACTCTGTG
CCAGCAGCCGCGGTAATACAGAGGGTGCAAGCGTTAATCGGAATTACTGGGCGTAAAGCGCGCGTAGG
TGGTTCGTTAAGT (SEQ ID NO: 78)

*Pseudomonas sp.*
TCCCTGGGCGGCAGCCTAACCATGCAGTCGAGCGGATGACAGAGAGCTTGCTCCTGGATTCAGCGGCG
GACGGGTGAGTAATGCCTAGGAATCTGCCTGGTAGTGGGGGACAACGTTTCGAAAGGAACGCTAATAC
CGCATACGTCCTACGGGAGAAAGCAGGGGACCTTCGGGCCTTGCGCTATCAGATGAGCCTAGGTCGGA
TTAGCTAGTTGGTGAGGTAATGGCTCACCAAGGCGACGATCCGTAACTGGTCTGAGAGGATGATCAGTC
ACACTGGAACTGAGACACGGTCCAGACTCCTACGGGAGGCAGCAGTGGGGAATATTGGACAATGGGC
GAAAGCCTGATCCAGCCATGCCGCGTGTGTGAAGAAGGTCTTCGGATTGTAAAGCACTTTAAGTTGGGA
GGAAGGGCAGTAAATTAATACTTTGCTGTTTTGACGTTACCGACAGAATAAGCACCGGCTAACTCTGTG
CCAGCAGCCGCGGTAATACAGAGGTGTTTTATGCGTTTAATCGGAATTACTGGGCGTAAAGCGCGCGTA
GGTGGTTTTGTTAAGT (SEQ ID NO: 79)

*Pseudomonas sp.*
TAATTGGCCGGCAGTCTAACCATGCAGTCGAGCGGATGACGGGAGCTTGCTCCCGAATTCAGCGGCGG
ACGGGTGAGTATGCCTAGGAATCTGCCTGGTAGTGGGGGACAACGTCTCGAAAGGGACGCTAATACCG
CATACGTCCTACGGGAGAAAGTGGGGGATCTTCGGACCTCACGCTATCAGATGAGCCTAGGTCGGATTA
GCTAGTTGGTGAGGTAATGGCTCACCAAGGCGACGATCCGTAACTGGTCTGAGAGGATGATCAGTCAC
ACTGGAACTGAGACACGGTCCAGACTCCTACGGGAGGCAGCAGTGGGGAATATTGGACAATGGGCGA
AAGCCTGATCCAGCCATGCCGCGTGTGTGAAGAAGGTCTTCGGATTGTAAAGCACTTTAAGTTGGGAGG
AAGGGCATTAACCTAATACGTTGATGTTTTGACGTTACCGACAGAATAAGCACCGGCTAACTCTGTGCCA
GCAGCCGCGGTAATACAGAGGGTGCAAGCGTTAATCGGAATTACTGGGCGTAAAGCGCGCGTAGGTG
GTTTGTTAAGTTGGATGTGAAAGCCCCGGGCTCAACCTGGGAACTGCATCCAAAACTGGCAAGCTAGAG
TAGGGCAGAGGGTGGTGGAATTTCCTGTGTAGCG (SEQ ID NO: 80)

Figure 1 – continued

*Burkholderia sediminicola*
GCCCTGGGCGCCTGCCTTAACATGCAGTCGACGGCAGCACGGGAGCAATCCTGGTGGCGAGTGGCGAA
CGGGTGAGTAATACATCGGAACGTGTCCTGTAGTGGGGGATAGCCCGGCGAAAGCCGGATTAATACCG
CATACGCTCTACGGAGGAAAGGGGGGGATCTTAGGACCTCCCGCTACAGGGGCGGCCGATGGCAGATT
AGCTAGTTGGTGGGGTAAAGGCCTACCAAGGCGACGATCTGTAGCTGGTCTGAGAGGACGACCAGCCA
CACTGGGACTGAGACACGGCCCAGACTCCTACGGGAGGCAGCAGTGGGGAATTTTGGACAATGGGCG
AAAGCCTGATCCAGCAATGCCGCGTGTGTGAAGAAGGCCTTCGGGTTGTAAAGCACTTTTGTCCGGAAA
GAAAACCTCCGCCCTAATATGGTGGGGGGATGACGGTACCGGAAGAATAAGCACCGGCTAACTACGTG
CCAGCAGCCGCGGTAATACGTAGGGTGCAAGCGTTAATCGGAATTACTGGGCGTAAAGCGTGCGCAGG
CGGTCCGCTAA (SEQ ID NO: 81)

*Burkholderia terrae*
TCACCTTGGCCGGCATGCTTCACATGCAGTCGACGGCAGCGCGGGGGCACCCTGGTGGCGAGTGGCGA
ACGGGTGAGTATACATCGGAACGTGTCCTGGAGTGGGGGATAGCCCGGCGAAAGCCGGATTAATACCG
CATACGATCTCAGGATGAAAGCGGGGGACCGAAAGGCCTCGCGCTCAAGGGGCGGCCGATGGCAGAT
TAGCTAGTTGGTGGGGTAAAGGCCTACCAAGGCGACGATCTGTAGCTGGTCTGAGAGGACGACCAGCC
ACACTGGGACTGAGACACGGCCCAGACTCCTACGGGAGGCAGCAGTGGGGAATTTTGGACAATGGGG
GCAACCCTGATCCAGCAATGCCGCGTGTGTGAAGAAGGCCTTCGGGTTGTAAAGCACTTTTGTCCGGAA
AGAAAACCTCCGTCCTAATACGGTGGGGGGATGACGGTACCGGAAGAATAAGCACCGGCTAACTACGT
GCCAGCAGCCGCGGTAATACGTAGGGTGCAAGCGTTAATCGGAATTACTGGGCGTAAAGCGTGCGCAG
GCGGTTCGCTAAGACCGATGTGAAATCCCCGGGCTTAACCTGGGAACTGCATTGGTGACTGGCGGGCTA
GAG (SEQ ID NO: 82)

*Burkholderia sp.*
TCCCCTTGGCGGCATGCCTTCCATGCAGTCGACGGCAGCACGGGGGCAACCCTGGTGGCGAGTGGCGA
ACGGGTGAGTATACATCGGAACGTGTCCTGGAGTGGGGGATAGCCCGGCGAAAGCCGGATTAATACCG
CATACGATCCCTGGATGAAAGCGGGGGACCGAAAGGCCTCGCGCTCAAGGGGCGGCCGATGGCAGAT
TAGCTAGTTGGTGGGGTAAAGGCCTACCAAGGCGACGATCTGTAGCTGGTCTGAGAGGACGACCAGCC
ACACTGGGACTGAGACACGGCCCAGACTCCTACGGGAGGCAGCAGTGGGGAATTTTGGACAATGGGG
GCAACCCTGATCCAGCAATGCCGCGTGTGTGAAGAAGGCCTTCGGGTTGTAAAGCACTTTTGTCCGGAA
AGAAAACCTCCGTCCTAATACGGTGGGGGGATGACGGTACCGGAAGAATAAGCACCGGCTAACTACGT
GCCAGCAGCCGCGGTAATACGTAGGGTGCAAGCGTTAATCGGAATTACTGGGCGTAAAGCGTGCGCAG
GCGGTTCGCTAAGACCGATGTGAAATCCCCGGGCTTAACCTGGGAACTGCATTGGTGACTGGCGGGCTA
GAGTATGGCAGAGGGGGTAGAATTTCCACGTGTAGCAGTGAAATGCGTAGAGATG (SEQ ID NO: 83)

Lane M: Prestained XL-Ladder (broad)
Lane 1: Crude enzyme solution
Lane 2: Ammonium sulfate fraction
Lane 3: Butyl-Toyopearl fraction
Lane 4: Resoure Q fraction
Lane 5: Gel filtration fraction (acetone concentrated)

FIG. 4:

FIG. 5:
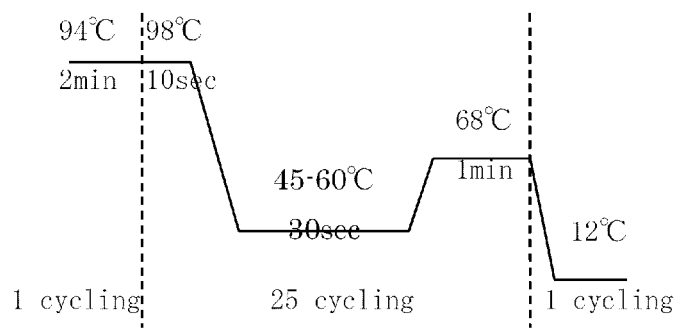
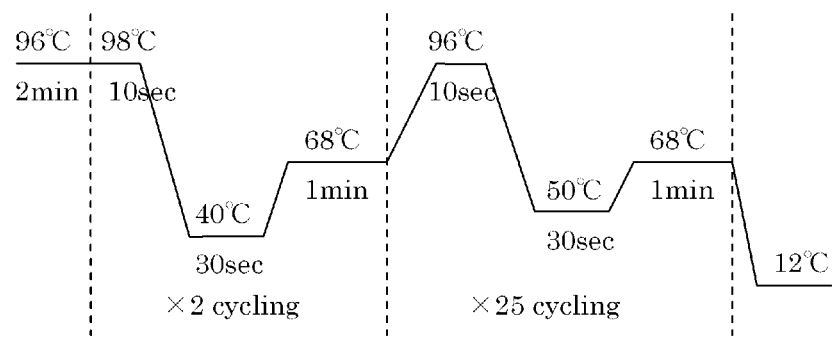

FIG. 8:

```
doir      1 mlriavlgagrigrlihagnvaaspnaqlvvvadpvesaaksllatrllgceastdpagvller   SEQ ID NO: 2
bh-iolg   1 mtriavlgagrigklihaanvasnsdakllvvvadpfegaanslaekllgceastdclsvller   SEQ ID NO: 4
ps-idh    1 mlriavlgagrlakihaanvaahpnatllvllvadpwregvdallstqllgceaaydcaavlnr   SEQ ID NO: 8
pa-idh    1 -mkiavlgagrignvhamnvasnpnvellvaiadpfidnaikltekyggkavkepmellies    SEQ ID NO: 6 doir     61 kdidavvigtptdthitfmleavrrgkavlcekpidldmekslaaanevergrgrvmlaf
bh-iolg  61 ddvdavvigtptdthiqfmlhavskgkavlcekpidldmkkslaaakeverhdgrvmlaf
ps-idh   61 kdidavvigtptdthidlllaavaqgkavlcekpidldiakarsaaqtverqggkvmlgf
pa-idh   60 navdaviiatptdthvdlmlsaarngkavlcekpvdlnleraevacaelkqcdvpvmlaf doir    121 nrrfdptsqafrnaidagdvgevrqviissrdpgmpprdyvehsggifrdmvihdldmar
bh-iolg 121 nrrfdptsqafrkaiddgevgdvrqvvitsrdpgmppreyvthsggifrdmvihdldlar
ps-idh  121 nrrfdpdmlrlrqaldagqigavrqviitsrdpglapreylehsggilrdmtihdfdtar
pa-idh  120 nrrfdpsaaemhsaiakgevgelhqimissrdpgfasmdylrhsggifrdmtihdfdmar doir    181 wllgeepvevmamasrlideslekltdfdtvmvqlrtasgkqchinccreavygydqrme
bh-iolg 181 wflgeepievmatgsrlvepslaevpdfdtvmlqlrtesgkqchinccreavygydqrle
ps-idh  181 hllgeepvcvsafasrlvdpsleqiddydsvmvllrtasgkqchinccrqavygydqrve
pa-idh  180 wllgeepvcvfasasrmlepaleplndfdtvmvqmitksgkqchincsrqavyghdqrie doir    241 vsgskgmllqenlrpstirrwskeatdvrepllnfflervyeaaykaeleafvdalntnsp
bh-iolg 241 vfgsrgmllqenlrpstirrwsasatdarepllnfflervyeaayktelfafvealrtntt
ps-idh  241 vsgasgvlltdnhrpstlrhwsaehtealeplqhfflervyadayrnelmqfvdalnegre
pa-idh  240 aygsagmllndnlrpstlrrfnksatdarvplvhfflervyadayrmeleafisavkhakp doir    301 lptsvqdglkalrladaalesalsgkavkv-----
bh-iolg 301 fptsvadglkalrladcalesamscrsvkv-----
ps-idh  301 lptgmrdglyalhladcalesvktgrsvavcydr
pa-idh  300 vpvtpydgymalkladcaqqsaetglpvql-----
```

FIG. 9:

atgacagtgagatttggtcttctgggcgccggacgcatcggcaaggttcacgcgaaagccgtcagcggca
atccggacgccgtgctcgtggcggttgccgatgcctttccggccgccgctgaagcaatcgccaaggccta
tggctgcgaggttcgcagcatcgaggcgatcgaggcggcctccgacatcgacgccgtggtcatctgcacg
ccgaccgacacgcatgccgacctgatcgagcgttttgcccgggccggcaaggccatcttctgcgaaaagc
cgatcgatctcgacgtcgatcgcgtcaaggcctgcctgaaggtggtctccgaaaccggggcgaagctgat
ggtcggcttcaaccgcgcttctacccatttatggccgtgcgaaaggcgatcgacgccggcacgattggc
gacgtcgagatggtgacgatcacctcgcgcgatccgggcgccccgccggtcgactatatcaagcggtcgg
gcggcatcttccgcgacatgacgatccacgatttcgacatggcgcgcttcctgctcggcgaggagccggt
ttcagtgacggccaccgccgccgtattggtcgacaaggcgatcggcgcagcgggcgacttcgacagcgtc
tccgtgatcctgcagacggcatccggcaagcaggcggtcatctccaactcgcgtcgcgccacctacggct
acgatcagcgcatcgaggtgcatggctcgaagggcgccgtcgcggccgagaaccagcgccccgtgtcgat
cgagatcgccaccggcgagggttatacgcgcccgccgctgcacgatttcttcatgacgcgctacaccgaa
gcctatgccaacgagatcgagagcttcatcgccgcgatcgagaagggcgcggaaatcacccgtccggca
aggatggcctcgcggcactcgcccttgccgacgcggccgtccgctcggtcgcggaaaagcgccagatcag
cgtcgcctga (SEQ ID NO: 68)

mtvrfgllgagrigkvhakavsgnpdavlvavadafpaaaeaiakaygcevrsieaieaasdidavvict
ptdthadlierfaragkaifcekpidldvdrvkaclkvvsetgaklmvgfnrastpfmavrkaidagtig
dvemvtitsrdpgappvdyikrsggifrdmtihdfdmarfllgeepvsvtataavlvdkaigaagdfdsv
svilqtasgkqavisnsrratygydqrievhgskgavaaenqrpvsieiatgegytrpplhdffmtryte
ayaneiesfiaaiekgaeitpsgkdglaalaladaavrsvaekrqisva (SEQ ID NO: 69)

FIG. 10:

atggaacatcaagtaagatgtgcagtattgggattaggaaggctcggttattatcatgcgaaaaatctcg
tcaccagtgtgccgggggcaaagctggtttgtgtcggtgatccgttaaaagggagagcggagcaggttgc
cagagaactcggtatcgaaaaatggtcagaggacccgtatgaagtgttagaagatcccggcattgatgct
gtcattatcgtaacgccgacaagcacacatggtgatatgatcatcaaagcagccgagaacggcaaacaga
tctttgttgaaaaaccgctgacattaagccttgaggaatcaaaagcagcttctgaaaaagttaaggagac
aggtgtcatctgccaagtcggctttatgagacggttcgatcccgcatacgcagatgccaaacggcggatc
gacgctggagaaatcggcaaacctatctattataaaggctttacgcgcgaccaaggcgcgcctcccgcag
aatttatcaaacacagcggtggaattttttatcgactgttccatccatgactatgatattgcccgttattt
gctaggggcggaaatcacttctgtttcaggacacggcaggattctgaacaatccgtttatggagcagtat
ggcgatgtggatcaggcgctgacgtatattgaatttgactcgggcgcagcggggacgtcgaggcaagca
gaacctctccatacggacatgacatccgggcggaggtgatcgggacagagggcagtattttcatagggac
attgagacatcaacatgtgaccatcctatcggctaaaggagcagttttgatatcattccagactttcaa
actcgttttcatgaagcctactgcttggagcttcagcatttcgccgagtgtgtccggaatggaaaaacac
cgattgtgactgatattgatgcgacgatcaatttagaagtgggtatcgccgcaaccaattcctttcgaaa
cggcatgccggtacagctagatgtgaagcgcgcttatacaggtatgtaa (SEQ ID NO: 70)

mehqvrcavlglgrlgyyhaknlvtsvpgaklvcvgdplkgracqvarclgickwscdpycvlcdpgida
viivtptsthgdmiikaaengkqifvekpltlsleeskaasekvketgvicqvgfmrrfdpayadakrri
dageigkpiyykgftrdqgappaefikhsggifidcsihdydiaryllgaeitsvsghgrilnnpfmeqy
gdvdqaltyiefdsgaagdveasrtspyghdiraevigtegsifigtlrhqhvtilsakgssfdiipdfq
trfheayclelqhfaecvrngktpivtdidatinlevgiaatnsfrngmpvqldvkraytgm (SEQ ID NO: 71)

FIG. 11:

atgttgataacgctttttaaaggggagaagaaaagtggatacgatcaaggttggaatattaggatacggat
tgtccggttctgtttttcacgggccgctgctggatgttctggatgaatatcaaatcagcaaaatcatgac
atcacggacagaagaagtgaaacgggattttccagatgctgaggttgtacatgagcttgaagaaatcaca
aatgaccctgccattgagcttgtcattgtcaccaccccgagcggccttcattacgagcatactatggcat
gcatacaggccggaaaacatgttgtgatggaaaaaccaatgacagcaacggccgaagaggggggaaacatt
aaaaagggctgccgatgaaaaaggcgtattattaagcgtatatcataaccgacgctgggataacgatttt
ttaacgattaaaaagctgatctctgagggatcccttgaagatatcaatacatatcaagtttcctataacc
gctacagacctgaagttcaagcgcggtggcgggaaaaagaaggcactgccactggtacgctgtatgatct
cggctcccacatcatagaccaaaccctgcatttgtttgggatgcctaaagccgtgactgcaaacgtgatg
gcccagcgggaaaatgccgaaacggttgactattttcatttaaccctggattatggcaagcttcaagcca
ttctatacggaggatcaatcgttccggcaaacggacctcgttatcaaatccatggaaaagattctagctt
tatcaaatatggaattgacggacaggaagacgcactcagagcgggaagaaaaccagaggatgacagctgg
ggtgcggatgttccggagttttacggaaagcttacaaccattcgtggctccgacaaaaaaacagaaacga
ttccatcagtaaatggctcctaccttacttattaccgtaaaatagcggaaagcatacgagaaggtgctgc
gctgccagtcactgctgaggaaggtattaatgtcatccgcatcattgaagccgcgatggaaagcagtaaa
gagaaacgaaccattatgctggagcactaa (SEQ ID NO: 72)

mlitllkgrrkvdtikvgilgyglsgsvfhgplldvldeyqiskimtsrteevkrdfpdaevvheleeit
ndpaielvivttpsglhyehtmaciqagkhvvmekpmtataeegetlkraadekgvllsvyhnrrwdndf
ltikklisegslediintyqvsynryrpevqarwrekegtatgtlydlgshiidqtlhlfgmpkavtanvm
aqrenaetvdyfhltldygklqailyggsivpangpryqihgkdssfikygidgqedalragrkpeddsw
gadvpcfygklttirgsdkktctipsvngsyltyyrkiacsiregaalpvtaccginviriicaamcssk
ekrtimleh (SEQ ID NO: 73)

| Lane M: | XL-ladder marker (low) | |
|---|---|---|
| 1: | E. coli BL21 (DE3) pETDuet-DOIR | soluble fraction |
| 2: | " pET21b-BH-IolG | " |
| 3: | " pET21b-Pa-Idh | " |
| 4: | " pET21b-Ps-Idh | " |
| 5: | " pET21b-Sf-Idh | " |
| 6: | " pET21b-Bs-IolX | " |
| 7: | " pET21b-Bs-IolW | " |
| 8: | " Pet21B(+) | " |
| 9: | " Pet21B-Bs-IolX | insoluble fraction |
| 10: | " Pet21B-Bs-IolW | " |

SEQUENCE LISTING

<160> NUMBER OF SEQ ID NOS: 86

<210> SEQ ID NO 1
<211> LENGTH: 993
<212> TYPE: DNA
<213> ORGANISM: Burkholderia terrae AKC-020
<220> FEATURE:
<221> NAME/KEY: CDS
<222> LOCATION: (1)..(993)

<400> SEQUENCE: 1

```
atg att cga atc gcc gta ctc ggt gcc ggc cgc att ggt cgc att cac      48
Met Ile Arg Ile Ala Val Leu Gly Ala Gly Arg Ile Gly Arg Ile His
1               5                   10                  15 gct ggc aac gtc gcc gct agt ccg aat gca caa ctg gtc gtg gtg gca      96
Ala Gly Asn Val Ala Ala Ser Pro Asn Ala Gln Leu Val Val Val Ala
                20                  25                  30 gac ccg gtt gaa agt gca gca aaa tcg ttg gct acc cgt ctg ggc tgc     144
Asp Pro Val Glu Ser Ala Ala Lys Ser Leu Ala Thr Arg Leu Gly Cys
            35                  40                  45 gaa gcc tcg acg gac ccc gcg ggc gtg ctc gaa cgc aaa gat atc gat     192
Glu Ala Ser Thr Asp Pro Ala Gly Val Leu Glu Arg Lys Asp Ile Asp
        50                  55                  60 gcg gtc gtc atc ggc acg ccg acg gac acg cac atc acg ttc atg ctt     240
Ala Val Val Ile Gly Thr Pro Thr Asp Thr His Ile Thr Phe Met Leu
65                  70                  75                  80 gaa gcc gtc agg cgc ggc aag gct gtt ctg tgt gag aag ccc atc gac     288
Glu Ala Val Arg Arg Gly Lys Ala Val Leu Cys Glu Lys Pro Ile Asp
                85                  90                  95 ctc gac atg gaa aag tcg ctt gcc gcg gca aac gag gtc gag cgc cag     336
Leu Asp Met Glu Lys Ser Leu Ala Ala Ala Asn Glu Val Glu Arg Gln
                100                 105                 110 cgt ggc cgc gtc atg ctc gct ttc aat cga cgt ttc gac ccg acg tcg     384
Arg Gly Arg Val Met Leu Ala Phe Asn Arg Arg Phe Asp Pro Thr Ser
            115                 120                 125 caa gca ttc cgc aac gcg att gac gcg ggc gat gtt ggc gaa gtg cgc     432
Gln Ala Phe Arg Asn Ala Ile Asp Ala Gly Asp Val Gly Glu Val Arg
        130                 135                 140 cag gtc atc att tcg agc cgc gac ccg ggc atg cct ccg cgt gac tat     480
Gln Val Ile Ile Ser Ser Arg Asp Pro Gly Met Pro Pro Arg Asp Tyr
145                 150                 155                 160 gtc gag cac tcg ggc ggc atc ttc cgc gac atg gtg atc cac gac ctg     528
Val Glu His Ser Gly Gly Ile Phe Arg Asp Met Val Ile His Asp Leu
                165                 170                 175
```

```
gat atg gcg cgc tgg ttg ctc ggc gaa gag ccc gtc gag gta atg gcg       576
Asp Met Ala Arg Trp Leu Leu Gly Glu Glu Pro Val Glu Val Met Ala
        180                 185                 190 atg gcc agc cgc ctc atc gac gag tcg ctc gaa aaa ctg acc gac ttc       624
Met Ala Ser Arg Leu Ile Asp Glu Ser Leu Glu Lys Leu Thr Asp Phe
    195                 200                 205 gat acg gtg atg gtg cag tta cgg acc gcg tcg ggc aag caa tgc cat       672
Asp Thr Val Met Val Gln Leu Arg Thr Ala Ser Gly Lys Gln Cys His
210                 215                 220 atc aac tgc tgt cgc gaa gcc gtg tac ggc tac gac cag cgc atg gaa       720
Ile Asn Cys Cys Arg Glu Ala Val Tyr Gly Tyr Asp Gln Arg Met Glu
225                 230                 235                 240 gtc tcg ggt tcg aag gga atg ctc ctt caa gag aat ctt cga ccg tcg       768
Val Ser Gly Ser Lys Gly Met Leu Leu Gln Glu Asn Leu Arg Pro Ser
            245                 250                 255 acg atc cgg cgc tgg tcc aag gaa gcg acc gac gtt cgc gag ccg ctg       816
Thr Ile Arg Arg Trp Ser Lys Glu Ala Thr Asp Val Arg Glu Pro Leu
        260                 265                 270 ctc aac ttc ttc ctg gag cgc tac gag gct gcg tac aag gcg gag ctc       864
Leu Asn Phe Phe Leu Glu Arg Tyr Glu Ala Ala Tyr Lys Ala Glu Leu
    275                 280                 285 gaa gcc ttc gtc gat gcg ctg aac acg aac tcg ccg ctg ccg acg tcc       912
Glu Ala Phe Val Asp Ala Leu Asn Thr Asn Ser Pro Leu Pro Thr Ser
290                 295                 300 gtg cag gac ggt ctg aag gcg ttg cgc ctc gcg gat gcg gca ctc gag       960
Val Gln Asp Gly Leu Lys Ala Leu Arg Leu Ala Asp Ala Ala Leu Glu
305                 310                 315                 320 tcc gcg ctg tcg ggc aaa gcc gtc aag gtg taa                           993
Ser Ala Leu Ser Gly Lys Ala Val Lys Val
            325                 330

<210> SEQ ID NO 2
<211> LENGTH: 330
<212> TYPE: PRT
<213> ORGANISM: Burkholderia terrae AKC-020

<400> SEQUENCE: 2

Met Ile Arg Ile Ala Val Leu Gly Ala Gly Arg Ile Gly Arg Ile His
1               5                   10                  15

Ala Gly Asn Val Ala Ala Ser Pro Asn Ala Gln Leu Val Val Ala
            20                  25                  30

Asp Pro Val Glu Ser Ala Ala Lys Ser Leu Ala Thr Arg Leu Gly Cys
        35                  40                  45

Glu Ala Ser Thr Asp Pro Ala Gly Val Leu Glu Arg Lys Asp Ile Asp
    50                  55                  60

Ala Val Val Ile Gly Thr Pro Thr Asp Thr His Ile Thr Phe Met Leu
65                  70                  75                  80

Glu Ala Val Arg Arg Gly Lys Ala Val Leu Cys Glu Lys Pro Ile Asp
                85                  90                  95

Leu Asp Met Glu Lys Ser Leu Ala Ala Ala Asn Glu Val Glu Arg Gln
            100                 105                 110

Arg Gly Arg Val Met Leu Ala Phe Asn Arg Arg Phe Asp Pro Thr Ser
        115                 120                 125

Gln Ala Phe Arg Asn Ala Ile Asp Ala Gly Asp Val Gly Glu Val Arg
    130                 135                 140

Gln Val Ile Ile Ser Ser Arg Asp Pro Gly Met Pro Pro Arg Asp Tyr
145                 150                 155                 160
```

```
Val Glu His Ser Gly Gly Ile Phe Arg Asp Met Val Ile His Asp Leu
            165                 170                 175
Asp Met Ala Arg Trp Leu Leu Gly Glu Pro Val Glu Val Met Ala
        180                 185                 190
Met Ala Ser Arg Leu Ile Asp Glu Ser Leu Glu Lys Leu Thr Asp Phe
        195                 200                 205
Asp Thr Val Met Val Gln Leu Arg Thr Ala Ser Gly Lys Gln Cys His
    210                 215                 220
Ile Asn Cys Cys Arg Glu Ala Val Tyr Gly Tyr Asp Gln Arg Met Glu
225                 230                 235                 240
Val Ser Gly Ser Lys Gly Met Leu Leu Gln Glu Asn Leu Arg Pro Ser
                245                 250                 255
Thr Ile Arg Arg Trp Ser Lys Glu Ala Thr Asp Val Arg Glu Pro Leu
            260                 265                 270
Leu Asn Phe Phe Leu Glu Arg Tyr Glu Ala Ala Tyr Lys Ala Glu Leu
        275                 280                 285
Glu Ala Phe Val Asp Ala Leu Asn Thr Asn Ser Pro Leu Pro Thr Ser
    290                 295                 300
Val Gln Asp Gly Leu Lys Ala Leu Arg Leu Ala Asp Ala Ala Leu Glu
305                 310                 315                 320
Ser Ala Leu Ser Gly Lys Ala Val Lys Val
                325                 330
```

```
<210> SEQ ID NO 3
<211> LENGTH: 993
<212> TYPE: DNA
<213> ORGANISM: Burkholderia sp. SJ98
<220> FEATURE:
<221> NAME/KEY: CDS
<222> LOCATION: (1)..(993)

<400> SEQUENCE: 3
```

```
atg act cgc att gca gtt ctc gga gca ggc cgt atc gga aag att cac      48
Met Thr Arg Ile Ala Val Leu Gly Ala Gly Arg Ile Gly Lys Ile His
1               5                   10                  15 gca gcg aac gtt gca tcg aac tcg gac gcg aag ctc gtc gtg gtt gca      96
Ala Ala Asn Val Ala Ser Asn Ser Asp Ala Lys Leu Val Val Val Ala
                20                  25                  30 gac ccg ttc gaa ggc gca gcc aac tct ttg gcg gag aag ctc ggt tgc     144
Asp Pro Phe Glu Gly Ala Ala Asn Ser Leu Ala Glu Lys Leu Gly Cys
            35                  40                  45 gaa gcg tcc acc gac tgt ctc tct gtt atc gag agg gac gac gtc gat     192
Glu Ala Ser Thr Asp Cys Leu Ser Val Ile Glu Arg Asp Asp Val Asp
        50                  55                  60 gct gtc gtc att ggc acg ccg acc gat acc cac atc cag ttc atg ctt     240
Ala Val Val Ile Gly Thr Pro Thr Asp Thr His Ile Gln Phe Met Leu
65                  70                  75                  80 cat gcg gtt tca aaa ggg aag gca gtt ctc tgc gag aaa ccc atc gac     288
His Ala Val Ser Lys Gly Lys Ala Val Leu Cys Glu Lys Pro Ile Asp
                85                  90                  95 ctg gat atg aaa aag tcg ctc gcg gca gcc aag gag gtc gaa cgg cac     336
Leu Asp Met Lys Lys Ser Leu Ala Ala Ala Lys Glu Val Glu Arg His
            100                 105                 110 gat gga cgc gtg atg ctg gca ttc aat cgt cga ttc gac ccg acg tcg     384
Asp Gly Arg Val Met Leu Ala Phe Asn Arg Arg Phe Asp Pro Thr Ser
        115                 120                 125 cag gcc ttc cgg aaa gcc atc gat gat ggg gaa gtc ggt gat gtc cga     432
Gln Ala Phe Arg Lys Ala Ile Asp Asp Gly Glu Val Gly Asp Val Arg
    130                 135                 140
```

```
cag gtt gtc att acc agt cgc gac ccc ggt atg ccc ccg cga gag tat        480
Gln Val Val Ile Thr Ser Arg Asp Pro Gly Met Pro Pro Arg Glu Tyr
145                 150                 155                 160 gtg acg cac tcc ggc ggc atc ttc cgc gac atg gtt att cac gac ctt        528
Val Thr His Ser Gly Gly Ile Phe Arg Asp Met Val Ile His Asp Leu
                165                 170                 175 gac ctc gca cga tgg ttt ctt gga gaa gag ccc att gaa gtg atg gcc        576
Asp Leu Ala Arg Trp Phe Leu Gly Glu Glu Pro Ile Glu Val Met Ala
            180                 185                 190 act ggt agc cgg ctc gtg gaa cca agc ctc gcg gaa gtt ccg gac ttc        624
Thr Gly Ser Arg Leu Val Glu Pro Ser Leu Ala Glu Val Pro Asp Phe
        195                 200                 205 gat acg gtc atg ctg caa ctg cgt acc gaa agc gga aag caa tgc cac        672
Asp Thr Val Met Leu Gln Leu Arg Thr Glu Ser Gly Lys Gln Cys His
    210                 215                 220 atc aat tgc tgt cgc gag gcc gtc tac ggt tac gac caa cgc ctc gaa        720
Ile Asn Cys Cys Arg Glu Ala Val Tyr Gly Tyr Asp Gln Arg Leu Glu
225                 230                 235                 240 gtg ttc ggc tcc cgc ggc atg ctc ctt cag gaa aat ctg cga ccc tcc        768
Val Phe Gly Ser Arg Gly Met Leu Leu Gln Glu Asn Leu Arg Pro Ser
                245                 250                 255 acg att cgc cgc tgg agc gcg agt gca acc gat gcc cgt gag ccg ctc        816
Thr Ile Arg Arg Trp Ser Ala Ser Ala Thr Asp Ala Arg Glu Pro Leu
            260                 265                 270 ctt aac ttt ttc ctg gag cgc tat gaa gcg gca tat aag acg gag ctc        864
Leu Asn Phe Phe Leu Glu Arg Tyr Glu Ala Ala Tyr Lys Thr Glu Leu
        275                 280                 285 acc gcc ttt gta gag gca ttg cga acg aac act acg ttc ccg act tct        912
Thr Ala Phe Val Glu Ala Leu Arg Thr Asn Thr Thr Phe Pro Thr Ser
    290                 295                 300 gtt gcg gac ggg ctt aaa gcg ttg cgg ctt gct gac tgc gct ctt gaa        960
Val Ala Asp Gly Leu Lys Ala Leu Arg Leu Ala Asp Cys Ala Leu Glu
305                 310                 315                 320 tct gcg atg tcg tgt agg tca gtt aaa gtc taa                            993
Ser Ala Met Ser Cys Arg Ser Val Lys Val
                325                 330
```

<210> SEQ ID NO 4
<211> LENGTH: 330
<212> TYPE: PRT
<213> ORGANISM: Burkholderia sp. SJ98

<400> SEQUENCE: 4

```
Met Thr Arg Ile Ala Val Leu Gly Ala Gly Arg Ile Gly Lys Ile His
1               5                   10                  15

Ala Ala Asn Val Ala Ser Asn Ser Asp Ala Lys Leu Val Val Ala
            20                  25                  30

Asp Pro Phe Glu Gly Ala Ala Asn Ser Leu Ala Glu Lys Leu Gly Cys
        35                  40                  45

Glu Ala Ser Thr Asp Cys Leu Ser Val Ile Glu Arg Asp Asp Val Asp
    50                  55                  60

Ala Val Val Ile Gly Thr Pro Thr Asp Thr His Ile Gln Phe Met Leu
65                  70                  75                  80

His Ala Val Ser Lys Gly Lys Ala Val Leu Cys Glu Lys Pro Ile Asp
                85                  90                  95

Leu Asp Met Lys Lys Ser Leu Ala Ala Ala Lys Glu Val Glu Arg His
            100                 105                 110

Asp Gly Arg Val Met Leu Ala Phe Asn Arg Arg Phe Asp Pro Thr Ser
```

```
            115                 120                 125
    Gln Ala Phe Arg Lys Ala Ile Asp Asp Gly Glu Val Gly Asp Val Arg
        130                 135                 140

Gln Val Val Ile Thr Ser Arg Asp Pro Gly Met Pro Pro Arg Glu Tyr
    145                 150                 155                 160

Val Thr His Ser Gly Ile Phe Arg Asp Met Val Ile His Asp Leu
                    165                 170                 175

Asp Leu Ala Arg Trp Phe Leu Gly Glu Glu Pro Ile Glu Val Met Ala
                180                 185                 190

Thr Gly Ser Arg Leu Val Glu Pro Ser Leu Ala Glu Val Pro Asp Phe
                195                 200                 205

Asp Thr Val Met Leu Gln Leu Arg Thr Glu Ser Gly Lys Gln Cys His
        210                 215                 220

Ile Asn Cys Cys Arg Glu Ala Val Tyr Gly Tyr Asp Gln Arg Leu Glu
    225                 230                 235                 240

Val Phe Gly Ser Arg Gly Met Leu Leu Gln Glu Asn Leu Arg Pro Ser
                    245                 250                 255

Thr Ile Arg Arg Trp Ser Ala Ser Ala Thr Asp Ala Arg Glu Pro Leu
                260                 265                 270

Leu Asn Phe Phe Leu Glu Arg Tyr Glu Ala Ala Tyr Lys Thr Glu Leu
                275                 280                 285

Thr Ala Phe Val Glu Ala Leu Arg Thr Asn Thr Thr Phe Pro Thr Ser
        290                 295                 300

Val Ala Asp Gly Leu Lys Ala Leu Arg Leu Ala Asp Cys Ala Leu Glu
    305                 310                 315                 320

Ser Ala Met Ser Cys Arg Ser Val Lys Val
                    325                 330

<210> SEQ ID NO 5
<211> LENGTH: 990
<212> TYPE: DNA
<213> ORGANISM: Pantoea sp. At-9b
<220> FEATURE:
<221> NAME/KEY: CDS
<222> LOCATION: (1)..(990)

<400> SEQUENCE: 5 atg aaa att gcc gta ctt ggc gca ggc cgc att ggc aac gtc cac gca      48
Met Lys Ile Ala Val Leu Gly Ala Gly Arg Ile Gly Asn Val His Ala
1               5                   10                  15 atg aat gtt gca agc aac ccc aat gtt gaa ctg gtc gcg att gct gat      96
Met Asn Val Ala Ser Asn Pro Asn Val Glu Leu Val Ala Ile Ala Asp
                20                  25                  30 cct ttc atc gac aac gct atc aaa ctg acg gag aaa tat ggt ggc aag     144
Pro Phe Ile Asp Asn Ala Ile Lys Leu Thr Glu Lys Tyr Gly Gly Lys
            35                  40                  45 gcc gtg aaa gag ccg atg gag ttg att gag agc aat gcg gtg gat gcc     192
Ala Val Lys Glu Pro Met Glu Leu Ile Glu Ser Asn Ala Val Asp Ala
        50                  55                  60 gtg atc att gcg aca cct acc gat acg cat gtt gat ctg atg ttg agt     240
Val Ile Ile Ala Thr Pro Thr Asp Thr His Val Asp Leu Met Leu Ser
65                  70                  75                  80 gca gcc cgc aat ggt aaa gcg gta ctg tgt gaa aaa ccg gta gac ctt     288
Ala Ala Arg Asn Gly Lys Ala Val Leu Cys Glu Lys Pro Val Asp Leu
                85                  90                  95 aac ctg gaa cgt gcc gaa gtc gcc tgc gca gag ctt aag caa tgc gat     336
Asn Leu Glu Arg Ala Glu Val Ala Cys Ala Glu Leu Lys Gln Cys Asp
            100                 105                 110
```

```
gtt ccc gtc atg att gcc ttt aac cgc cgc ttt gat ccc agc gca gct      384
Val Pro Val Met Ile Ala Phe Asn Arg Arg Phe Asp Pro Ser Ala Ala
        115                 120                 125 gaa atg cac agc gcc att gcg aaa ggt gaa gtg ggc gaa ctg cat caa      432
Glu Met His Ser Ala Ile Ala Lys Gly Glu Val Gly Glu Leu His Gln
130                 135                 140 atc atg att tcc agc cgt gac ccg ggc ttt gcc tcc atg gac tat ctg      480
Ile Met Ile Ser Ser Arg Asp Pro Gly Phe Ala Ser Met Asp Tyr Leu
145                 150                 155                 160 cgt cac tct ggc ggc atc ttc cgg gac atg acg att cat gat ttt gac      528
Arg His Ser Gly Gly Ile Phe Arg Asp Met Thr Ile His Asp Phe Asp
                165                 170                 175 atg gcg cgc tgg tta ctc ggt gaa gag cct gtg cag gta ttt gcc tct      576
Met Ala Arg Trp Leu Leu Gly Glu Glu Pro Val Gln Val Phe Ala Ser
                180                 185                 190 gcc agc cgt atg ctg gag ccg gca tta gaa ccg ttg aat gat ttc gat      624
Ala Ser Arg Met Leu Glu Pro Ala Leu Glu Pro Leu Asn Asp Phe Asp
                195                 200                 205 acc gtg atg gtt cag atg atc act aaa tcg ggt aag caa tgc cac atc      672
Thr Val Met Val Gln Met Ile Thr Lys Ser Gly Lys Gln Cys His Ile
210                 215                 220 aac tgt agt cgt caa gcc gtc tat gga cat gac caa cgc att gaa gct      720
Asn Cys Ser Arg Gln Ala Val Tyr Gly His Asp Gln Arg Ile Glu Ala
225                 230                 235                 240 tat ggt tct gca ggg atg tta ctc aat gac aat ctt cgc cca tcc act      768
Tyr Gly Ser Ala Gly Met Leu Leu Asn Asp Asn Leu Arg Pro Ser Thr
                245                 250                 255 ctg cgt cgt ttc aat aaa tcg gca acc gat gct cgc gtt cca tta gtc      816
Leu Arg Arg Phe Asn Lys Ser Ala Thr Asp Ala Arg Val Pro Leu Val
                260                 265                 270 cac ttc ttc ctc gaa cgc tat gcg gat gcc tac cgg atg gaa ctg gaa      864
His Phe Phe Leu Glu Arg Tyr Ala Asp Ala Tyr Arg Met Glu Leu Glu
                275                 280                 285 gcc ttc att tcc gcg gtt aag cat gcg aag ccc gtt cct gtt acc cct      912
Ala Phe Ile Ser Ala Val Lys His Ala Lys Pro Val Pro Val Thr Pro
                290                 295                 300 tat gat gga tat atg gcg ctg aag ctc gcc gac tgt gcg caa caa tcg      960
Tyr Asp Gly Tyr Met Ala Leu Lys Leu Ala Asp Cys Ala Gln Gln Ser
305                 310                 315                 320 gct gaa act ggt tta cct gtg cag ctt taa                              990
Ala Glu Thr Gly Leu Pro Val Gln Leu
                325

<210> SEQ ID NO 6
<211> LENGTH: 329
<212> TYPE: PRT
<213> ORGANISM: Pantoea sp. At-9b

<400> SEQUENCE: 6

Met Lys Ile Ala Val Leu Gly Ala Gly Arg Ile Gly Asn Val His Ala
1               5                   10                  15

Met Asn Val Ala Ser Asn Pro Asn Val Glu Leu Val Ala Ile Ala Asp
                20                  25                  30

Pro Phe Ile Asp Asn Ala Ile Lys Leu Thr Glu Lys Tyr Gly Gly Lys
            35                  40                  45

Ala Val Lys Glu Pro Met Glu Leu Ile Glu Ser Asn Ala Val Asp Ala
        50                  55                  60

Val Ile Ile Ala Thr Pro Thr Asp Thr His Val Asp Leu Met Leu Ser
65                  70                  75                  80
```

```
Ala Ala Arg Asn Gly Lys Ala Val Leu Cys Glu Lys Pro Val Asp Leu
                85                  90                  95

Asn Leu Glu Arg Ala Glu Val Ala Cys Ala Glu Leu Lys Gln Cys Asp
            100                 105                 110

Val Pro Val Met Ile Ala Phe Asn Arg Arg Phe Asp Pro Ser Ala Ala
        115                 120                 125

Glu Met His Ser Ala Ile Ala Lys Gly Glu Val Gly Glu Leu His Gln
    130                 135                 140

Ile Met Ile Ser Ser Arg Asp Pro Gly Phe Ala Ser Met Asp Tyr Leu
145                 150                 155                 160

Arg His Ser Gly Gly Ile Phe Arg Asp Met Thr Ile His Asp Phe Asp
                165                 170                 175

Met Ala Arg Trp Leu Leu Gly Glu Pro Val Gln Val Phe Ala Ser
            180                 185                 190

Ala Ser Arg Met Leu Glu Pro Ala Leu Glu Pro Leu Asn Asp Phe Asp
        195                 200                 205

Thr Val Met Val Gln Met Ile Thr Lys Ser Gly Lys Gln Cys His Ile
    210                 215                 220

Asn Cys Ser Arg Gln Ala Val Tyr Gly His Asp Gln Arg Ile Glu Ala
225                 230                 235                 240

Tyr Gly Ser Ala Gly Met Leu Leu Asn Asp Asn Leu Arg Pro Ser Thr
                245                 250                 255

Leu Arg Arg Phe Asn Lys Ser Ala Thr Asp Ala Arg Val Pro Leu Val
            260                 265                 270

His Phe Phe Leu Glu Arg Tyr Ala Asp Ala Tyr Arg Met Glu Leu Glu
        275                 280                 285

Ala Phe Ile Ser Ala Val Lys His Ala Lys Pro Val Pro Val Thr Pro
    290                 295                 300

Tyr Asp Gly Tyr Met Ala Leu Lys Leu Ala Asp Cys Ala Gln Gln Ser
305                 310                 315                 320

Ala Glu Thr Gly Leu Pro Val Gln Leu
                325

<210> SEQ ID NO 7
<211> LENGTH: 1005
<212> TYPE: DNA
<213> ORGANISM: Pseudomonas synxantha BG33R
<220> FEATURE:
<221> NAME/KEY: CDS
<222> LOCATION: (1)..(1005)

<400> SEQUENCE: 7 atg cta cgt att gcc gtt cta ggt gcg ggg cgc atc gcc aag atc cac    48
Met Leu Arg Ile Ala Val Leu Gly Ala Gly Arg Ile Ala Lys Ile His
1               5                   10                  15 gcc gcc aac gtc gct gcc cat ccc aac gcc acg ctg gtg ctg gtg gcc    96
Ala Ala Asn Val Ala Ala His Pro Asn Ala Thr Leu Val Leu Val Ala
            20                  25                  30 gac ccc tgg cgc gaa ggc gtc gat gcc ctg agc acg cag ttg gga tgt   144
Asp Pro Trp Arg Glu Gly Val Asp Ala Leu Ser Thr Gln Leu Gly Cys
        35                  40                  45 gaa gca gca tac gac tgc gcc gcc gtg ctg aac cgc aag gac atc gac   192
Glu Ala Ala Tyr Asp Cys Ala Ala Val Leu Asn Arg Lys Asp Ile Asp
    50                  55                  60 gca gtg gtg atc ggc acg ccc acc gac acc cat atc gac ctg ttg ctg   240
Ala Val Val Ile Gly Thr Pro Thr Asp Thr His Ile Asp Leu Leu Leu
65                  70                  75                  80
```

```
gcc gcc gtg gcc cag ggc aag gcg gta ctc tgt gaa aag ccc atc gac    288
Ala Ala Val Ala Gln Gly Lys Ala Val Leu Cys Glu Lys Pro Ile Asp
            85                  90                  95 ctg gat atc gcc aag gcg cgc agc gca gca caa acc gtg gag cgt cag    336
Leu Asp Ile Ala Lys Ala Arg Ser Ala Ala Gln Thr Val Glu Arg Gln
100                 105                 110 ggc ggc aag gtg atg ctt ggc ttc aac cgc cgt ttc gac ccg gac atg    384
Gly Gly Lys Val Met Leu Gly Phe Asn Arg Arg Phe Asp Pro Asp Met
        115                 120                 125 ctg cgg ctg cgc cag gcc ttg gac gcc ggc cag atc ggc gca gtg cgc    432
Leu Arg Leu Arg Gln Ala Leu Asp Ala Gly Gln Ile Gly Ala Val Arg
    130                 135                 140 cag gtg atc att acc agc cgc gac ccc ggc ctg gct ccg cgc gag tat    480
Gln Val Ile Ile Thr Ser Arg Asp Pro Gly Leu Ala Pro Arg Glu Tyr
145                 150                 155                 160 ctg gaa cat tcc ggt ggc atc ctg cgc gat atg act atc cac gac ttc    528
Leu Glu His Ser Gly Gly Ile Leu Arg Asp Met Thr Ile His Asp Phe
                165                 170                 175 gac act gcc cgg cac ttg ctg ggt gaa gag ccg gtg caa gtc agc gcc    576
Asp Thr Ala Arg His Leu Leu Gly Glu Glu Pro Val Gln Val Ser Ala
            180                 185                 190 ttc gcc agc cgc ctg gta gac ccg agc ctg gaa cag att gac gac tac    624
Phe Ala Ser Arg Leu Val Asp Pro Ser Leu Glu Gln Ile Asp Asp Tyr
        195                 200                 205 gac agc gtg atg gtc ctg ctg cgc acc gcc tcg ggc aag caa tgc cat    672
Asp Ser Val Met Val Leu Leu Arg Thr Ala Ser Gly Lys Gln Cys His
    210                 215                 220 atc aac tgc tgc cgc cag gcg gtg tat ggc tac gat caa cgt gta gaa    720
Ile Asn Cys Cys Arg Gln Ala Val Tyr Gly Tyr Asp Gln Arg Val Glu
225                 230                 235                 240 gtc tcc ggc gcc agc ggc gta ctc acc gat aac cac agg ccc agt       768
Val Ser Gly Ala Ser Gly Val Leu Leu Thr Asp Asn His Arg Pro Ser
                245                 250                 255 acc ttg cga cac tgg agt gct gaa cac act gaa gca ctg gag ccg ttg    816
Thr Leu Arg His Trp Ser Ala Glu His Thr Glu Ala Leu Glu Pro Leu
            260                 265                 270 cag cac ttt ttc ctt gag cgc tat gcg gat gcc tat cgt aat gag ttg    864
Gln His Phe Phe Leu Glu Arg Tyr Ala Asp Ala Tyr Arg Asn Glu Leu
        275                 280                 285 atg cag ttt gtc gat gcg ctg aat gag ggg cgt gag ttg ccc acc ggc    912
Met Gln Phe Val Asp Ala Leu Asn Glu Gly Arg Glu Leu Pro Thr Gly
    290                 295                 300 atg cgt gat ggg ctg tat gcc ttg cac ctg gct gac tgt gcg ttg gag    960
Met Arg Asp Gly Leu Tyr Ala Leu His Leu Ala Asp Cys Ala Leu Glu
305                 310                 315                 320 tcg gtt aag acg ggg cgc agc gtg gcc gtt tgt tat gac cgg tag       1005
Ser Val Lys Thr Gly Arg Ser Val Ala Val Cys Tyr Asp Arg
                325                 330

<210> SEQ ID NO 8
<211> LENGTH: 334
<212> TYPE: PRT
<213> ORGANISM: Pseudomonas synxantha BG33R

<400> SEQUENCE: 8

Met Leu Arg Ile Ala Val Leu Gly Ala Gly Arg Ile Ala Lys Ile His
1               5                   10                  15

Ala Ala Asn Val Ala Ala His Pro Asn Ala Thr Leu Val Leu Val Ala
            20                  25                  30
```

-continued

```
Asp Pro Trp Arg Glu Gly Val Asp Ala Leu Ser Thr Gln Leu Gly Cys
         35                  40                  45

Glu Ala Ala Tyr Asp Cys Ala Ala Val Leu Asn Arg Lys Asp Ile Asp
 50                  55                  60

Ala Val Val Ile Gly Thr Pro Thr Asp Thr His Ile Asp Leu Leu Leu
 65                  70                  75                  80

Ala Ala Val Ala Gln Gly Lys Ala Val Leu Cys Glu Lys Pro Ile Asp
                 85                  90                  95

Leu Asp Ile Ala Lys Ala Arg Ser Ala Ala Gln Thr Val Glu Arg Gln
             100                 105                 110

Gly Gly Lys Val Met Leu Gly Phe Asn Arg Arg Phe Asp Pro Asp Met
         115                 120                 125

Leu Arg Leu Arg Gln Ala Leu Asp Ala Gly Gln Ile Gly Ala Val Arg
130                 135                 140

Gln Val Ile Ile Thr Ser Arg Asp Pro Gly Leu Ala Pro Arg Glu Tyr
145                 150                 155                 160

Leu Glu His Ser Gly Gly Ile Leu Arg Asp Met Thr Ile His Asp Phe
                165                 170                 175

Asp Thr Ala Arg His Leu Leu Gly Glu Glu Pro Val Gln Val Ser Ala
            180                 185                 190

Phe Ala Ser Arg Leu Val Asp Pro Ser Leu Glu Gln Ile Asp Asp Tyr
        195                 200                 205

Asp Ser Val Met Val Leu Leu Arg Thr Ala Ser Gly Lys Gln Cys His
210                 215                 220

Ile Asn Cys Cys Arg Gln Ala Val Tyr Gly Tyr Asp Gln Arg Val Glu
225                 230                 235                 240

Val Ser Gly Ala Ser Gly Val Leu Leu Thr Asp Asn His Arg Pro Ser
                245                 250                 255

Thr Leu Arg His Trp Ser Ala Glu His Thr Glu Ala Leu Glu Pro Leu
            260                 265                 270

Gln His Phe Phe Leu Glu Arg Tyr Ala Asp Ala Tyr Arg Asn Glu Leu
        275                 280                 285

Met Gln Phe Val Asp Ala Leu Asn Glu Gly Arg Glu Leu Pro Thr Gly
290                 295                 300

Met Arg Asp Gly Leu Tyr Ala Leu His Leu Ala Asp Cys Ala Leu Glu
305                 310                 315                 320

Ser Val Lys Thr Gly Arg Ser Val Ala Val Cys Tyr Asp Arg
                325                 330

<210> SEQ ID NO 9
<211> LENGTH: 33
<212> TYPE: DNA
<213> ORGANISM: Burkholderia terrae AKC-020
<220> FEATURE:
<221> NAME/KEY: CDS
<222> LOCATION: (1)..(33)

<400> SEQUENCE: 9 cga atc gcc gta ctc ggt gcc ggc cgc att ggt                    33
Arg Ile Ala Val Leu Gly Ala Gly Arg Ile Gly
 1               5                  10

<210> SEQ ID NO 10
<211> LENGTH: 11
<212> TYPE: PRT
<213> ORGANISM: Burkholderia terrae AKC-020

<400> SEQUENCE: 10
```

```
Arg Ile Ala Val Leu Gly Ala Gly Arg Ile Gly
1               5                   10
```

<210> SEQ ID NO 11
<211> LENGTH: 39
<212> TYPE: DNA
<213> ORGANISM: Burkholderia terrae AKC-020
<220> FEATURE:
<221> NAME/KEY: CDS
<222> LOCATION: (1)..(39)

<400> SEQUENCE: 11

```
gat gcg gtc gtc atc ggc acg ccg acg gac acg cac atc         39
Asp Ala Val Val Ile Gly Thr Pro Thr Asp Thr His Ile
1               5                   10
```

<210> SEQ ID NO 12
<211> LENGTH: 13
<212> TYPE: PRT
<213> ORGANISM: Burkholderia terrae AKC-020

<400> SEQUENCE: 12

```
Asp Ala Val Val Ile Gly Thr Pro Thr Asp Thr His Ile
1               5                   10
```

<210> SEQ ID NO 13
<211> LENGTH: 39
<212> TYPE: DNA
<213> ORGANISM: Burkholderia terrae AKC-020
<220> FEATURE:
<221> NAME/KEY: CDS
<222> LOCATION: (1)..(39)

<400> SEQUENCE: 13

```
ggc aag gct gtt ctg tgt gag aag ccc atc gac ctc gac         39
Gly Lys Ala Val Leu Cys Glu Lys Pro Ile Asp Leu Asp
1               5                   10
```

<210> SEQ ID NO 14
<211> LENGTH: 13
<212> TYPE: PRT
<213> ORGANISM: Burkholderia terrae AKC-020

<400> SEQUENCE: 14

```
Gly Lys Ala Val Leu Cys Glu Lys Pro Ile Asp Leu Asp
1               5                   10
```

<210> SEQ ID NO 15
<211> LENGTH: 33
<212> TYPE: DNA
<213> ORGANISM: Burkholderia terrae AKC-020
<220> FEATURE:
<221> NAME/KEY: CDS
<222> LOCATION: (1)..(33)

<400> SEQUENCE: 15

```
gtc atg ctc gct ttc aat cga cgt ttc gac ccg                 33
Val Met Leu Ala Phe Asn Arg Arg Phe Asp Pro
1               5                   10
```

<210> SEQ ID NO 16
<211> LENGTH: 11
<212> TYPE: PRT
<213> ORGANISM: Burkholderia terrae AKC-020

<400> SEQUENCE: 16

```
Val Met Leu Ala Phe Asn Arg Arg Phe Asp Pro
1               5                   10

<210> SEQ ID NO 17
<211> LENGTH: 27
<212> TYPE: DNA
<213> ORGANISM: Burkholderia terrae AKC-020
<220> FEATURE:
<221> NAME/KEY: CDS
<222> LOCATION: (1)..(27)

<400> SEQUENCE: 17 cac tcg ggc ggc atc ttc cgc gac atg                          27
His Ser Gly Gly Ile Phe Arg Asp Met
1               5

<210> SEQ ID NO 18
<211> LENGTH: 9
<212> TYPE: PRT
<213> ORGANISM: Burkholderia terrae AKC-020

<400> SEQUENCE: 18

His Ser Gly Gly Ile Phe Arg Asp Met
1               5

<210> SEQ ID NO 19
<211> LENGTH: 30
<212> TYPE: DNA
<213> ORGANISM: Burkholderia terrae AKC-020
<220> FEATURE:
<221> NAME/KEY: CDS
<222> LOCATION: (1)..(30)

<400> SEQUENCE: 19 gcg cgc tgg ttg ctc ggc gaa gag ccc gtc                      30
Ala Arg Trp Leu Leu Gly Glu Glu Pro Val
1               5                   10

<210> SEQ ID NO 20
<211> LENGTH: 10
<212> TYPE: PRT
<213> ORGANISM: Burkholderia terrae AKC-020

<400> SEQUENCE: 20

Ala Arg Trp Leu Leu Gly Glu Glu Pro Val
1               5                   10

<210> SEQ ID NO 21
<211> LENGTH: 69
<212> TYPE: DNA
<213> ORGANISM: Burkholderia terrae AKC-020
<220> FEATURE:
<221> NAME/KEY: CDS
<222> LOCATION: (1)..(69)

<400> SEQUENCE: 21 gac ttc gat acg gtg atg gtg cag tta cgg acc gcg tcg ggc aag caa    48
Asp Phe Asp Thr Val Met Val Gln Leu Arg Thr Ala Ser Gly Lys Gln
1               5                   10                  15 tgc cat atc aac tgc tgt cgc                                  69
Cys His Ile Asn Cys Cys Arg
            20

<210> SEQ ID NO 22
<211> LENGTH: 23
<212> TYPE: PRT
<213> ORGANISM: Burkholderia terrae AKC-020
```

-continued

```
<400> SEQUENCE: 22

Asp Phe Asp Thr Val Met Val Gln Leu Arg Thr Ala Ser Gly Lys Gln
1               5                   10                  15

Cys His Ile Asn Cys Cys Arg
            20

<210> SEQ ID NO 23
<211> LENGTH: 24
<212> TYPE: DNA
<213> ORGANISM: Burkholderia terrae AKC-020
<220> FEATURE:
<221> NAME/KEY: CDS
<222> LOCATION: (1)..(24)

<400> SEQUENCE: 23 gcc gtg tac ggc tac gac cag cgc                                         24
Ala Val Tyr Gly Tyr Asp Gln Arg
1               5

<210> SEQ ID NO 24
<211> LENGTH: 8
<212> TYPE: PRT
<213> ORGANISM: Burkholderia terrae AKC-020

<400> SEQUENCE: 24

Ala Val Tyr Gly Tyr Asp Gln Arg
1               5

<210> SEQ ID NO 25
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: h is a, c or t
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: h is a, c or t
<220> FEATURE:
<221> NAME/KEY: misc_feature
<222> LOCATION: (15)..(15)
<223> OTHER INFORMATION: n is a, c, g, or t

<400> SEQUENCE: 25
atgathmgna thgcngt                                                      17

<210> SEQ ID NO 26
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
```

```
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: m is a or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: h is a, c or t

<400> SEQUENCE: 26
ggngcnggnm gnathgg                                               17

<210> SEQ ID NO 27
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 27
gtngcngtna cnga                                                  14

<210> SEQ ID NO 28
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 28
gtngcngtng cnga                                                  14
```

```
<210> SEQ ID NO 29
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (6)..(6)
<223> OTHER INFORMATION: y is t or c
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (15)..(15)
<223> OTHER INFORMATION: n is a, c, g, or t

<400> SEQUENCE: 29
ttytgygara arccnat                                                17

<210> SEQ ID NO 30
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (6)..(6)
<223> OTHER INFORMATION: y is t or c
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: y is t or c

<400> SEQUENCE: 30
ttytgygara arccnyt                                                17

<210> SEQ ID NO 31
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
```

```
<223> OTHER INFORMATION: r is g or a
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c
<220> FEATURE:
<221> NAME/KEY: misc_feature
<222> LOCATION: (15)..(15)
<223> OTHER INFORMATION: y is t or c
<220> FEATURE:
<221> NAME/KEY: misc_feature
<222> LOCATION: (16)..(16)
<223> OTHER INFORMATION: m is a or c

<400> SEQUENCE: 31
cargtnggnt tyaaymg                                                  17

<210> SEQ ID NO 32
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c
<220> FEATURE:
<221> NAME/KEY: misc_feature
<222> LOCATION: (16)..(16)
<223> OTHER INFORMATION: m is a or c

<400> SEQUENCE: 32
cargtnggnt tyatgmg                                                  17

<210> SEQ ID NO 33
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c
<220> FEATURE:
<221> NAME/KEY: misc_feature
```

```
<222> LOCATION: (15)..(15)
<223> OTHER INFORMATION: y is t or c
<220> FEATURE:
<221> NAME/KEY: misc_feature
<222> LOCATION: (16)..(16)
<223> OTHER INFORMATION: m is a or c

<400> SEQUENCE: 33
atggtnggnt tyaaymg                                                  17

<210> SEQ ID NO 34
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c
<220> FEATURE:
<221> NAME/KEY: misc_feature
<222> LOCATION: (16)..(16)
<223> OTHER INFORMATION: m is a or c

<400> SEQUENCE: 34
atggtnggnt tyatgmg                                                  17

<210> SEQ ID NO 35
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: r is g or a
<220> FEATURE:
<221> NAME/KEY: misc_feature
<222> LOCATION: (7)..(7)
<223> OTHER INFORMATION: r is g or a
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: r is g or a
<220> FEATURE:
<221> NAME/KEY: misc_feature
<222> LOCATION: (16)..(16)
<223> OTHER INFORMATION: d is a, g or t

<400> SEQUENCE: 35
catrtcraar tcrtgdat                                                 18

<210> SEQ ID NO 36
<211> LENGTH: 17
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (6)..(6)
<223> OTHER INFORMATION: r is g or a
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: r is g or a
<220> FEATURE:
<221> NAME/KEY: misc_feature
<222> LOCATION: (15)..(15)
<223> OTHER INFORMATION: d is a, g or t

<400> SEQUENCE: 36
acrtcraart crtgdat                                                 17

<210> SEQ ID NO 37
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: r is g or a
<220> FEATURE:
<221> NAME/KEY: misc_feature
<222> LOCATION: (7)..(7)
<223> OTHER INFORMATION: d is a, g or t
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: r is g or a
<220> FEATURE:
<221> NAME/KEY: misc_feature
<222> LOCATION: (16)..(16)
<223> OTHER INFORMATION: d is a, g or t

<400> SEQUENCE: 37
catrtcdatr tcrtgdat                                                18

<210> SEQ ID NO 38
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (6)..(6)
<223> OTHER INFORMATION: d is a, g or t
<220> FEATURE:
<221> NAME/KEY: misc_feature
<222> LOCATION: (9)..(9)
<220> FEATURE:
<221> NAME/KEY: misc_feature
<222> LOCATION: (12)..(12)
<220> FEATURE:
<221> NAME/KEY: misc_feature
```

```
<222> LOCATION: (15)..(15)
<223> OTHER INFORMATION: d is a, g or t

<400> SEQUENCE: 38
acrtcdatrt crtgdat                                                  17

<210> SEQ ID NO 39
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: k is g or t
<220> FEATURE:
<221> NAME/KEY: misc_feature
<222> LOCATION: (3)..(3)
<223> OTHER INFORMATION: y is t or c
<220> FEATURE:
<221> NAME/KEY: misc_feature
<222> LOCATION: (6)..(6)
<223> OTHER INFORMATION: r is g or a
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: r is g or a

<400> SEQUENCE: 39
ckytgrtcrt anccrta                                                  17

<210> SEQ ID NO 40
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: k is g or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: r is g or a
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: r is g or a

<400> SEQUENCE: 40
cknacrtcrt anccrta                                                  17
```

```
<210> SEQ ID NO 41
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: r is g or a
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: r is g or a
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: y is t or c

<400> SEQUENCE: 41
gcrtcnacra angcytc                                                  17

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tcgacatgga aaagtcgctt gc                                            22

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
tgcctccgcg tgactatgt                                                19

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
tgaccgactt cgatacggtg at                                            22

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tcaatcgcgt tgcggaatgc                                               20
```

```
<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
ttctcacaca gaacagcctt gc                                              22

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
tagccaacga ttttgctgca ct                                              22

<210> SEQ ID NO 48
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (8)..(8)
<223> OTHER INFORMATION: w is a or t
<220> FEATURE:
<221> NAME/KEY: misc_feature
<222> LOCATION: (10)..(10)
<223> OTHER INFORMATION: s is g or c
<220> FEATURE:
<221> NAME/KEY: misc_feature
<222> LOCATION: (12)..(12)
<223> OTHER INFORMATION: w is a or t

<400> SEQUENCE: 48
ntcgastwts gwgtt                                                      15

<210> SEQ ID NO 49
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(7)
<223> OTHER INFORMATION: s is g or c
<220> FEATURE:
<221> NAME/KEY: misc_feature
<222> LOCATION: (8)..(8)
<223> OTHER INFORMATION: w is a or t
<220> FEATURE:
<221> NAME/KEY: misc_feature
<222> LOCATION: (11)..(11)
```

```
<223> OTHER INFORMATION: n is a, c, g, or t
<220> FEATURE:
<221> NAME/KEY: misc_feature
<222> LOCATION: (13)..(13)
<223> OTHER INFORMATION: w is a or t

<400> SEQUENCE: 49
ngtcgaswga nawgaa                                                       16

<210> SEQ ID NO 50
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: w is a or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 50
wgtgnagwan canaga                                                       16

<210> SEQ ID NO 51
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: w is a or t
<220> FEATURE:
<221> NAME/KEY: misc_feature
<222> LOCATION: (13)..(13)
<223> OTHER INFORMATION: n is a, c, g, or t

<400> SEQUENCE: 51
wgcnagtnag wanaag                                                       16

<210> SEQ ID NO 52
<211> LENGTH: 16
<212> TYPE: DNA
<213> ORGANISM: Artificial Sequence
```

-continued

```
<220> FEATURE:
<223> OTHER INFORMATION: Primer
<220> FEATURE:
<221> NAME/KEY: misc_feature
<222> LOCATION: (2)..(2)
<223> OTHER INFORMATION: w is a or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (13)..(13)
<223> OTHER INFORMATION: n is a, c, g, or t

<400> SEQUENCE: 52
awgcangncw ganata                                                   16

<210> SEQ ID NO 53
<211> LENGTH: 16
<212> TYPE: DNA
<213> ORGANISM: Artificial Sequence
<220> FEATURE:
<223> OTHER INFORMATION: Orimer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(7)
<223> OTHER INFORMATION: s is g or c
<220> FEATURE:
<221> NAME/KEY: misc_feature
<222> LOCATION: (8)..(8)
<223> OTHER INFORMATION: w is a or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: w is a or t

<400> SEQUENCE: 53
gtncgaswca nawgtt                                                   16

<210> SEQ ID NO 54
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: w is a or t
<220> FEATURE:
```

```
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: w is a or t

<400> SEQUENCE: 54
agwgnagwan cawagg                                                16

<210> SEQ ID NO 55
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: s is g or c
<220> FEATURE:
<221> NAME/KEY: misc_feature
<222> LOCATION: (7)..(7)
<223> OTHER INFORMATION: w is a or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: w is a or t
<220> FEATURE:
<221> NAME/KEY: misc_feature
<222> LOCATION: (16)..(16)
<223> OTHER INFORMATION: n is a, c, g, or t

<400> SEQUENCE: 55
gtcgaswgan awgaan                                                16

<210> SEQ ID NO 56
<211> LENGTH: 18
<212> TYPE: DNA
<213> ORGANISM: Artificial Sequence
<220> FEATURE:
<223> OTHER INFORMATION: Primer

<400> SEQUENCE: 56
tacggcgtgg aactcatc                                              18

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
tgagtgatac caagacatgc c                                          21

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
agaggatcca atgattcgaa tcgccgtact                                  30
```

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
agagaagctt caccttgacg gctttgc                                                27

<210> SEQ ID NO 60
<211> LENGTH: 346
<212> TYPE: PRT
<213> ORGANISM: Lactobacillus casei

<400> SEQUENCE: 60

```
Met Val Val Lys Val Gly Val Ile Gly Thr Gly Ala Met Gly Arg Ala
1               5                   10                  15

His Ile Asp Arg Leu Thr Asn Val Leu Thr Gly Ala Glu Val Val Ala
            20                  25                  30

Val Thr Asp Ile Asp His Glu Ala Ala Glu Ala Ala Val Arg Asp Phe
        35                  40                  45

His Leu Asn Ala Lys Val Tyr Pro Asp Thr Ser Leu Leu Gln Asp
    50                  55                  60

Pro Asp Ile Asp Ala Val Phe Val Val Ser Phe Gly Gly Ala His Glu
65                  70                  75                  80

Ala Thr Val Leu Lys Ala Leu Asp Thr Asp Lys Phe Ile Phe Thr Glu
                85                  90                  95

Lys Pro Leu Ala Thr Thr Leu Glu Gly Ala Lys Arg Ile Val Asp Lys
            100                 105                 110

Glu Leu Thr Lys Ser Lys Lys Val Ile Gln Val Gly Phe Met Arg Arg
        115                 120                 125

Tyr Asp Gln Gly Ile Arg Ala Leu Lys Glu Lys Leu Asp Thr Gly Ile
    130                 135                 140

Ile Gly Ala Pro Leu Val Val Arg Ala Ser His Ile Asn Pro Asn Val
145                 150                 155                 160

Ala Ser Asn Tyr Ser Asn Glu Met Ala Ile Thr Asp Thr Leu Ile His
                165                 170                 175

Glu Ile Asp Glu Met His Trp Leu Leu Asp Asp Glu Tyr Thr Ser Ile
            180                 185                 190

Gln Ile Thr Tyr Pro Arg Gln Ser Ala Glu Val Arg Asn Glu Gly Leu
        195                 200                 205

His Asp Pro Gln Leu Ala Thr Leu Thr Thr Lys Lys Gly Thr Val Ile
    210                 215                 220

Gln Val Leu Val His Val Thr Ala Gln Tyr Gly Tyr Glu Val Lys Leu
225                 230                 235                 240

Glu Val Ile Gly Glu Thr Gly Glu Leu Gln Leu Pro Asn Tyr Gly Leu
                245                 250                 255

Gly Pro Ile Leu Arg Ser Asn Ala Asn Gln Gln Thr Ala Val Glu Met
            260                 265                 270

Ser Trp Ile Asn Arg Phe Ile Gln Ala Tyr Asn Thr Glu Val Gln Glu
        275                 280                 285

Phe Ile Asp Gln Val Ala Lys Ser Glu Pro Pro Val Gly Pro Ser Ala
    290                 295                 300

Trp Asp Gly Tyr Ile Ala Ala Ile Thr Ala Ala Ala Ala Asn Arg Ser
```

```
            305                 310                 315                 320
Gln Lys Asp Gln Glu Thr Val Leu Ile Asn Val Ala Gly Thr Pro Thr
                    325                 330                 335

Phe Tyr Gln Asn Lys Asn Ala Ile His Ala
                340                 345

<210> SEQ ID NO 61
<211> LENGTH: 350
<212> TYPE: PRT
<213> ORGANISM: Lactobacillus casei

<400> SEQUENCE: 61

Met Thr Gln Lys Thr Ile Lys Ile Gly Ile Val Gly Leu Gly Arg Leu
1               5                   10                  15

Gly Lys Ile His Ala Thr Asn Ile Ala Thr Lys Ile Gln His Ala Lys
                20                  25                  30

Leu Gln Ala Ala Thr Ser Val Val Pro Ala Glu Leu Asp Trp Ala Lys
            35                  40                  45

Lys Glu Leu Gly Val Glu Glu Val Phe Glu Asp Phe Asp Asp Met Val
        50                  55                  60

Gln His Ala Asp Ile Asp Ala Val Phe Ile Val Ser Pro Ser Gly Phe
65                  70                  75                  80

His Leu Gln Gln Ile Glu Ser Ala Leu Asn Ala Gly Lys His Val Phe
                85                  90                  95

Ser Glu Lys Pro Ile Gly Leu Asp Ile Glu Ala Ile Glu His Thr Gln
                100                 105                 110

Gln Val Ile Ala Gln His Ala Asn Leu Lys Phe Gln Leu Gly Phe Met
            115                 120                 125

Arg Arg Phe Asp Asp Ser Tyr Arg Tyr Ala Lys Gln Leu Val Asp Gln
130                 135                 140

Gly Lys Ile Gly Asp Ile Thr Leu Ile Arg Ser Tyr Ser Ile Asp Pro
145                 150                 155                 160

Ala Ala Gly Met Ala Ser Phe Val Lys Phe Ala Thr Ser Ala Asn Ser
                165                 170                 175

Gly Gly Leu Phe Leu Asp Met Ser Ile His Asp Ile Asp Val Ile Arg
            180                 185                 190

Trp Phe Thr Gly Lys Glu Ile Asp Lys Val Trp Ala Ile Gly Leu Asn
        195                 200                 205

Arg Ala Tyr Pro Val Leu Asp Lys Ala Gly Glu Leu Glu Thr Gly Ala
210                 215                 220

Ala Leu Met Gln Leu Glu Asp Lys Thr Met Ala Ile Leu Val Ala Gly
225                 230                 235                 240

Arg Asn Ala Ala His Gly Tyr His Val Glu Thr Glu Ile Ile Gly Thr
                245                 250                 255

Lys Gly Met Leu Arg Ile Ala Gln Val Pro Glu Lys Asn Leu Val Thr
            260                 265                 270

Val Met Asn Glu Glu Gly Ile Ile Arg Pro Thr Ser Gln Asn Phe Pro
        275                 280                 285

Glu Arg Phe Ala Gln Ala Phe Leu Ser Glu Gln Ala Phe Val Asn
290                 295                 300

Ser Ile Leu Asn Asn Gln Asp Val Gly Ile Thr Ala Glu Asp Gly Leu
305                 310                 315                 320

Gln Gly Thr Lys Ala Ala Leu Ala Leu Gln Glu Ala Phe Glu Lys Asn
                325                 330                 335
```

```
Asp Ile Val Gln Val Ala Ser Val Asp Lys Lys Val Gly Ala
            340                 345                 350

<210> SEQ ID NO 62
<211> LENGTH: 330
<212> TYPE: PRT
<213> ORGANISM: Sinorhizobium meliloti

<400> SEQUENCE: 62

Met Thr Val Arg Phe Gly Leu Leu Gly Ala Gly Arg Ile Gly Lys Val
1               5                   10                  15

His Ala Lys Ala Val Ser Gly Asn Ala Asp Ala Arg Leu Val Ala Val
            20                  25                  30

Ala Asp Ala Phe Pro Ala Ala Ala Glu Ala Ile Ala Gly Ala Tyr Gly
        35                  40                  45

Cys Glu Val Arg Thr Ile Asp Ala Ile Glu Ala Ala Asp Ile Asp
    50                  55                  60

Ala Val Val Ile Cys Thr Pro Thr Asp Thr His Ala Asp Leu Ile Glu
65                  70                  75                  80

Arg Phe Ala Arg Ala Gly Lys Ala Ile Phe Cys Glu Lys Pro Ile Asp
                85                  90                  95

Leu Asp Ala Glu Arg Val Arg Ala Cys Leu Lys Val Val Ser Asp Thr
            100                 105                 110

Lys Ala Lys Leu Met Val Gly Phe Asn Arg Arg Phe Asp Pro His Phe
        115                 120                 125

Met Ala Val Arg Lys Ala Ile Asp Asp Gly Arg Ile Gly Glu Val Glu
    130                 135                 140

Met Val Thr Ile Thr Ser Arg Asp Pro Ser Ala Pro Pro Val Asp Tyr
145                 150                 155                 160

Ile Lys Arg Ser Gly Gly Ile Phe Arg Asp Met Thr Ile His Asp Phe
                165                 170                 175

Asp Met Ala Arg Phe Leu Leu Gly Glu Glu Pro Val Ser Val Thr Ala
            180                 185                 190

Thr Ala Ala Val Leu Ile Asp Lys Ala Ile Gly Asp Ala Gly Asp Tyr
        195                 200                 205

Asp Ser Val Ser Val Ile Leu Gln Thr Ala Ser Gly Lys Gln Ala Ile
    210                 215                 220

Ile Ser Asn Ser Arg Arg Ala Thr Tyr Gly Tyr Asp Gln Arg Ile Glu
225                 230                 235                 240

Val His Gly Ser Lys Gly Ala Val Ala Ala Glu Asn Gln Arg Pro Val
                245                 250                 255

Ser Ile Glu Ile Ala Thr Gly Asp Gly Tyr Thr Arg Pro Pro Leu His
            260                 265                 270

Asp Phe Phe Met Thr Arg Tyr Thr Glu Ala Tyr Ala Asn Glu Ile Glu
        275                 280                 285

Ser Phe Ile Ala Ala Ile Glu Lys Gly Ala Glu Ile Ala Pro Ser Gly
    290                 295                 300

Asn Asp Gly Leu Ala Ala Leu Ala Leu Ala Asp Ala Ala Val Arg Ser
305                 310                 315                 320

Val Ala Glu Lys Arg Gln Ile Ser Ile Ala
                325                 330

<210> SEQ ID NO 63
<211> LENGTH: 344
<212> TYPE: PRT
<213> ORGANISM: Bacillus subtilis
```

<400> SEQUENCE: 63

Met Ser Leu Arg Ile Gly Val Ile Gly Thr Gly Ala Ile Gly Lys Glu
1               5                   10                  15

His Ile Asn Arg Ile Thr Asn Lys Leu Ser Gly Ala Glu Ile Val Ala
            20                  25                  30

Val Thr Asp Val Asn Gln Glu Ala Ala Gln Lys Val Val Glu Gln Tyr
        35                  40                  45

Gln Leu Asn Ala Thr Val Tyr Pro Asn Asp Ser Leu Leu Ala Asp
    50                  55                  60

Glu Asn Val Asp Ala Val Leu Val Thr Ser Trp Gly Pro Ala His Glu
65                  70                  75                  80

Ser Ser Val Leu Lys Ala Ile Lys Ala Gln Lys Tyr Val Phe Cys Glu
                85                  90                  95

Lys Pro Leu Ala Thr Thr Ala Glu Gly Cys Met Arg Ile Val Glu Glu
            100                 105                 110

Glu Ile Lys Val Gly Lys Arg Leu Val Gln Val Gly Phe Met Arg Arg
        115                 120                 125

Tyr Asp Ser Gly Tyr Val Gln Leu Lys Glu Ala Leu Asp Asn His Val
130                 135                 140

Ile Gly Glu Pro Leu Met Ile His Cys Ala His Arg Asn Pro Thr Val
145                 150                 155                 160

Gly Asp Asn Tyr Thr Thr Asp Met Ala Val Val Asp Thr Leu Val His
                165                 170                 175

Glu Ile Asp Val Leu His Trp Leu Val Asn Asp Tyr Glu Ser Val
            180                 185                 190

Gln Val Ile Tyr Pro Lys Lys Ser Lys Asn Ala Leu Pro His Leu Lys
        195                 200                 205

Asp Pro Gln Ile Val Ile Glu Thr Lys Gly Gly Ile Val Ile Asn
210                 215                 220

Ala Glu Ile Tyr Val Asn Cys Lys Tyr Gly Tyr Asp Ile Gln Cys Glu
225                 230                 235                 240

Ile Val Gly Glu Asp Gly Ile Ile Lys Leu Pro Glu Pro Ser Ser Ile
                245                 250                 255

Ser Leu Arg Lys Glu Gly Arg Phe Ser Thr Asp Ile Leu Met Asp Trp
            260                 265                 270

Gln Arg Arg Phe Val Ala Ala Tyr Asp Val Glu Ile Gln Asp Phe Ile
        275                 280                 285

Asp Ser Ile Gln Lys Lys Gly Glu Val Ser Gly Pro Thr Ala Trp Asp
290                 295                 300

Gly Tyr Ile Ala Ala Val Thr Thr Asp Ala Cys Val Lys Ala Gln Glu
305                 310                 315                 320

Ser Gly Gln Lys Glu Lys Val Glu Leu Lys Glu Lys Pro Glu Phe Tyr
                325                 330                 335

Gln Ser Phe Thr Thr Val Gln Asn
            340

<210> SEQ ID NO 64
<211> LENGTH: 365
<212> TYPE: PRT
<213> ORGANISM: Galdieria sulphuraria

<400> SEQUENCE: 64

Met Gln Thr Asp Gln Val Thr Gln Thr Phe Tyr Lys Gln Ala Thr Ser
1               5                   10                  15

Ser Leu Gln Leu Glu Ala Ser Asp Ile Ser Lys Leu Val Arg Ile Gly
        20                  25                  30

Val Ile Gly Cys Gly Arg Ile Gly Gln Leu His Ile Asp Asn Ile Asn
        35                  40                  45

Ser Arg Ile Ala Asn Ala Gln Val Val Cys Val Ser Asp Phe Ile Pro
50                  55                  60

Asn Ala Ala Ile Gln Val Ala Lys Lys Phe His Ile Pro Met Ala Cys
65                  70                  75                  80

Thr Lys His Glu Asp Leu Leu Asp His Ala Lys Val Asp Ala Val Ile
                85                  90                  95

Val Cys Ser Pro Thr Asp Thr His Ala Gln Ile Ile Lys Asp Ala Ala
            100                 105                 110

Lys Arg Gly Ile His Val Phe Cys Glu Lys Pro Ile Asp Thr Gln Leu
        115                 120                 125

Ala Val Ile Arg Asp Ala Ile Gln Thr Thr Lys Gln Tyr Gly Ile Lys
    130                 135                 140

Phe Met Val Gly Phe Gln Arg Arg Phe Asp Arg Asn Phe Gln Arg Val
145                 150                 155                 160

Leu Glu Ala Arg Lys Ser Gly Ser Leu Gly Asp Pro Leu Lys Leu Thr
                165                 170                 175

Leu Ile Ser Arg Asp Pro Ala Pro Pro Met Glu Tyr Leu Lys Gln
            180                 185                 190

Ser Gly Gly Ile Phe Leu Asp Gln Ala Ile His Asp Phe Asp Met Ala
        195                 200                 205

Arg Phe Leu Met Gly Glu Asp Ile Val Glu Ile Tyr Ala Thr Gly Phe
    210                 215                 220

Ala Arg Asp Pro Lys Val Ala Glu Ile Gly Asp Ile Asp Asn Ala Thr
225                 230                 235                 240

Cys His Val Lys Phe Gln Ser Gly Ala Ile Gly Ile Asp Asn Ala
                245                 250                 255

Arg Glu Thr His Tyr Gly Tyr Asp Gln Arg Ala Glu Leu Phe Gly Ser
            260                 265                 270

Lys Gly Thr Ile Ser Ile Asp Asn Asp Phe Pro Asn Thr Ala His Thr
        275                 280                 285

Leu Ser Pro Asn Gly Leu Thr Ser Asp Leu Pro Leu His Phe Phe Met
    290                 295                 300

Glu Arg Tyr Ser Asn Ala Tyr Leu Glu Glu Met Gln Ala Phe Ile Arg
305                 310                 315                 320

Cys Leu Gln Glu Asn Lys Pro Val Pro Val Gly Gly Glu Glu Gly Leu
                325                 330                 335

Ile Pro Val Val Tyr Ser Glu Ala Ala Lys Lys Ser Phe Gln Glu Asn
            340                 345                 350

Arg Pro Val Leu Val Lys Glu Ile Asp Pro Ser Leu Pro
        355                 360                 365

<210> SEQ ID NO 65
<211> LENGTH: 329
<212> TYPE: PRT
<213> ORGANISM: Sinorhizobium fredii

<400> SEQUENCE: 65

Met Thr Val Arg Phe Gly Leu Leu Gly Ala Gly Arg Ile Gly Lys Val
1               5                   10                  15

His Ala Lys Ala Val Ser Gly Asn Pro Asp Ala Val Leu Val Ala Val

```
            20                  25                  30
Ala Asp Ala Phe Pro Ala Ala Glu Ala Ile Ala Lys Ala Tyr Gly
        35                  40                  45

Cys Glu Val Arg Ser Ile Glu Ala Ile Glu Ala Ser Asp Ile Asp
    50                  55                  60

Ala Val Val Ile Cys Thr Pro Thr Asp Thr His Ala Asp Leu Ile Glu
65                  70                  75                  80

Arg Phe Ala Arg Ala Gly Lys Ala Ile Phe Cys Glu Lys Pro Ile Asp
                85                  90                  95

Leu Asp Val Asp Arg Val Lys Ala Cys Leu Lys Val Val Ser Glu Thr
                100                 105                 110

Gly Ala Lys Leu Met Val Gly Phe Asn Arg Ala Ser Thr Pro Phe Met
            115                 120                 125

Ala Val Arg Lys Ala Ile Asp Ala Gly Thr Ile Gly Asp Val Glu Met
            130                 135                 140

Val Thr Ile Thr Ser Arg Asp Pro Gly Ala Pro Val Asp Tyr Ile
145                 150                 155                 160

Lys Arg Ser Gly Gly Ile Phe Arg Asp Met Thr Ile His Asp Phe Asp
                165                 170                 175

Met Ala Arg Phe Leu Leu Gly Glu Glu Pro Val Ser Val Thr Ala Thr
            180                 185                 190

Ala Ala Val Leu Val Asp Lys Ala Ile Gly Ala Gly Asp Phe Asp
            195                 200                 205

Ser Val Ser Val Ile Leu Gln Thr Ala Ser Gly Lys Gln Ala Val Ile
    210                 215                 220

Ser Asn Ser Arg Arg Ala Thr Tyr Gly Tyr Asp Gln Arg Ile Glu Val
225                 230                 235                 240

His Gly Ser Lys Gly Ala Val Ala Ala Glu Asn Gln Arg Pro Val Ser
                245                 250                 255

Ile Glu Ile Ala Thr Gly Glu Gly Tyr Thr Arg Pro Pro Leu His Asp
                260                 265                 270

Phe Phe Met Thr Arg Tyr Thr Glu Ala Tyr Ala Asn Glu Ile Glu Ser
            275                 280                 285

Phe Ile Ala Ala Ile Glu Lys Gly Ala Glu Ile Thr Pro Ser Gly Lys
        290                 295                 300

Asp Gly Leu Ala Ala Leu Ala Leu Ala Asp Ala Ala Val Arg Ser Val
305                 310                 315                 320

Ala Glu Lys Arg Gln Ile Ser Val Ala
                325

<210> SEQ ID NO 66
<211> LENGTH: 12
<212> TYPE: PRT
<213> ORGANISM: Burkholderia terrae AKC-020

<400> SEQUENCE: 66

Met Ile Arg Ile Ala Val Leu Gly Ala Gly Arg Ile
1               5                   10

<210> SEQ ID NO 67
<211> LENGTH: 13
<212> TYPE: PRT
<213> ORGANISM: Burkholderia terrae AKC-020

<400> SEQUENCE: 67

Ala Glu Leu Glu Ala Phe Val Asp Ala Leu Asn Thr Asn
```

<210> SEQ ID NO 68
<211> LENGTH: 990
<212> TYPE: DNA
<213> ORGANISM: Sinorhizobium fredii
<220> FEATURE:
<221> NAME/KEY: CDS
<222> LOCATION: (1)..(990)

<400> SEQUENCE: 68

```
atg aca gtg aga ttt ggt ctt ctg ggc gcc gga cgc atc ggc aag gtt      48
Met Thr Val Arg Phe Gly Leu Leu Gly Ala Gly Arg Ile Gly Lys Val
1               5                   10                  15 cac gcg aaa gcc gtc agc ggc aat ccg gac gcc gtc ctc gtg gcg gtt      96
His Ala Lys Ala Val Ser Gly Asn Pro Asp Ala Val Leu Val Ala Val
                20                  25                  30 gcc gat gcc ttt ccg gcc gcc gct gaa gca atc gcc aag gcc tat ggc     144
Ala Asp Ala Phe Pro Ala Ala Ala Glu Ala Ile Ala Lys Ala Tyr Gly
            35                  40                  45 tgc gag gtt cgc agc atc gag gcg atc gag gcg gcc tcc gac atc gac     192
Cys Glu Val Arg Ser Ile Glu Ala Ile Glu Ala Ala Ser Asp Ile Asp
        50                  55                  60 gcc gtg gtc atc tgc acg ccg acc gac acg cat gcc gac ctg atc gag     240
Ala Val Val Ile Cys Thr Pro Thr Asp Thr His Ala Asp Leu Ile Glu
65                  70                  75                  80 cgt ttt gcc cgg gcc ggc aag gcc atc ttc tgc gaa aag ccg atc gat     288
Arg Phe Ala Arg Ala Gly Lys Ala Ile Phe Cys Glu Lys Pro Ile Asp
                85                  90                  95 ctc gac gtc gat cgc gtc aag gcc tgc ctg aag gtg gtc tcc gaa acc     336
Leu Asp Val Asp Arg Val Lys Ala Cys Leu Lys Val Val Ser Glu Thr
            100                 105                 110 ggg gcg aag ctg atg gtc ggc ttc aac cgc gct tct acc cca ttt atg     384
Gly Ala Lys Leu Met Val Gly Phe Asn Arg Ala Ser Thr Pro Phe Met
        115                 120                 125 gcc gtg cga aag gcg atc gac gcc ggc acg att ggc gac gtc gag atg     432
Ala Val Arg Lys Ala Ile Asp Ala Gly Thr Ile Gly Asp Val Glu Met
    130                 135                 140 gtg acg atc acc tcg cgc gat ccg ggc gcc ccg gtc gac tat atc         480
Val Thr Ile Thr Ser Arg Asp Pro Gly Ala Pro Pro Val Asp Tyr Ile
145                 150                 155                 160 aag cgg tcg ggc ggc atc ttc cgc gac atg acg atc cac gat ttc gac     528
Lys Arg Ser Gly Gly Ile Phe Arg Asp Met Thr Ile His Asp Phe Asp
                165                 170                 175 atg gcg cgc ttc ctg ctc ggc gag gag ccg gtt tca gtg acg gcc acc     576
Met Ala Arg Phe Leu Leu Gly Glu Glu Pro Val Ser Val Thr Ala Thr
            180                 185                 190 gcc gcc gta ttg gtc gac aag gcg atc ggc gca gcg ggc gac ttc gac     624
Ala Ala Val Leu Val Asp Lys Ala Ile Gly Ala Ala Gly Asp Phe Asp
        195                 200                 205 agc gtc tcc gtg atc ctg cag acg gca tcc ggc aag cag gcg gtc atc     672
Ser Val Ser Val Ile Leu Gln Thr Ala Ser Gly Lys Gln Ala Val Ile
    210                 215                 220 tcc aac tcg cgt cgc gcc acc tac ggc tac gat cag cgc atc gag gtg     720
Ser Asn Ser Arg Arg Ala Thr Tyr Gly Tyr Asp Gln Arg Ile Glu Val
225                 230                 235                 240 cat ggc tcg aag ggc gcc gtc gcg gcc gag aac cag cgc ccc gtg tcg     768
His Gly Ser Lys Gly Ala Val Ala Ala Glu Asn Gln Arg Pro Val Ser
                245                 250                 255 atc gag atc gcc acc ggc gag ggt tat acg cgc ccg ccg ctg cac gat     816
Ile Glu Ile Ala Thr Gly Glu Gly Tyr Thr Arg Pro Pro Leu His Asp
```

```
                        260                 265                 270
ttc atg acg cgc tac acc gaa gcc tat gcc aac gag atc gag agc       864
Phe Met Thr Arg Tyr Thr Glu Ala Tyr Ala Asn Glu Ile Glu Ser
Phe
    275                 280                 285 ttc atc gcc gcg atc gag aag ggc gcg gaa atc acc ccg tcc ggc aag   912
Phe Ile Ala Ala Ile Glu Lys Gly Ala Glu Ile Thr Pro Ser Gly Lys
290                 295                 300 gat ggc ctc gcg gca ctc gcc ctt gcc gac gcg gcc gtc cgc tcg gtc   960
Asp Gly Leu Ala Ala Leu Ala Leu Ala Asp Ala Ala Val Arg Ser Val
305                 310                 315                 320 gcg gaa aag cgc cag atc agc gtc gcc tga                           990
Ala Glu Lys Arg Gln Ile Ser Val Ala
                325

<210> SEQ ID NO 69
<211> LENGTH: 329
<212> TYPE: PRT
<213> ORGANISM: Sinorhizobium fredii

<400> SEQUENCE: 69

Met Thr Val Arg Phe Gly Leu Leu Gly Ala Gly Arg Ile Gly Lys Val
1               5                   10                  15

His Ala Lys Ala Val Ser Gly Asn Pro Asp Ala Val Leu Val Ala Val
            20                  25                  30

Ala Asp Ala Phe Pro Ala Ala Glu Ala Ile Ala Lys Ala Tyr Gly
        35                  40                  45

Cys Glu Val Arg Ser Ile Glu Ala Ile Glu Ala Ser Asp Ile Asp
    50                  55                  60

Ala Val Val Ile Cys Thr Pro Thr Asp Thr His Ala Asp Leu Ile Glu
65                  70                  75                  80

Arg Phe Ala Arg Ala Gly Lys Ala Ile Phe Cys Glu Lys Pro Ile Asp
                85                  90                  95

Leu Asp Val Asp Arg Val Lys Ala Cys Leu Lys Val Val Ser Glu Thr
            100                 105                 110

Gly Ala Lys Leu Met Val Gly Phe Asn Arg Ala Ser Thr Pro Phe Met
        115                 120                 125

Ala Val Arg Lys Ala Ile Asp Ala Gly Thr Ile Gly Asp Val Glu Met
    130                 135                 140

Val Thr Ile Thr Ser Arg Asp Pro Gly Ala Pro Pro Val Asp Tyr Ile
145                 150                 155                 160

Lys Arg Ser Gly Gly Ile Phe Arg Asp Met Thr Ile His Asp Phe Asp
                165                 170                 175

Met Ala Arg Phe Leu Leu Gly Glu Glu Pro Val Ser Val Thr Ala Thr
            180                 185                 190

Ala Ala Val Leu Val Asp Lys Ala Ile Gly Ala Ala Gly Asp Phe Asp
        195                 200                 205

Ser Val Ser Val Ile Leu Gln Thr Ala Ser Gly Lys Gln Ala Val Ile
    210                 215                 220

Ser Asn Ser Arg Arg Ala Thr Tyr Gly Tyr Asp Gln Arg Ile Glu Val
225                 230                 235                 240

His Gly Ser Lys Gly Ala Val Ala Ala Glu Asn Gln Arg Pro Val Ser
                245                 250                 255

Ile Glu Ile Ala Thr Gly Glu Gly Tyr Thr Arg Pro Leu His Asp
            260                 265                 270

Phe Phe Met Thr Arg Tyr Thr Glu Ala Tyr Ala Asn Glu Ile Glu Ser
        275                 280                 285
```

```
Phe Ile Ala Ala Ile Glu Lys Gly Ala Glu Ile Thr Pro Ser Gly Lys
    290                 295                 300
Asp Gly Leu Ala Ala Leu Ala Leu Ala Asp Ala Ala Val Arg Ser Val
305                 310                 315                 320
Ala Glu Lys Arg Gln Ile Ser Val Ala
                325

<210> SEQ ID NO 70
<211> LENGTH: 1029
<212> TYPE: DNA
<213> ORGANISM: Bacillus subtilis
<220> FEATURE:
<221> NAME/KEY: CDS
<222> LOCATION: (1)..(1029)

<400> SEQUENCE: 70 atg gaa cat caa gta aga tgt gca gta ttg gga tta gga agg ctc ggt       48
Met Glu His Gln Val Arg Cys Ala Val Leu Gly Leu Gly Arg Leu Gly
1               5                   10                  15 tat tat cat gcg aaa aat ctc gtc acc agt gtg ccg ggg gca aag ctg       96
Tyr Tyr His Ala Lys Asn Leu Val Thr Ser Val Pro Gly Ala Lys Leu
                20                  25                  30 gtt tgt gtc ggt gat ccg tta aaa ggg aga gcg gag cag gtt gcc aga     144
Val Cys Val Gly Asp Pro Leu Lys Gly Arg Ala Glu Gln Val Ala Arg
            35                  40                  45 gaa ctc ggt atc gaa aaa tgg tca gag gac ccg tat gaa gtg tta gaa     192
Glu Leu Gly Ile Glu Lys Trp Ser Glu Asp Pro Tyr Glu Val Leu Glu
        50                  55                  60 gat ccc ggc att gat gct gtc att atc gta acg ccg aca agc aca cat     240
Asp Pro Gly Ile Asp Ala Val Ile Ile Val Thr Pro Thr Ser Thr His
65                  70                  75                  80 ggt gat atg atc atc aaa gca gcc gag aac ggc aaa cag atc ttt gtt     288
Gly Asp Met Ile Ile Lys Ala Ala Glu Asn Gly Lys Gln Ile Phe Val
                85                  90                  95 gaa aaa ccg ctg aca tta agc ctt gag gaa tca aaa gca gct tct gaa     336
Glu Lys Pro Leu Thr Leu Ser Leu Glu Glu Ser Lys Ala Ala Ser Glu
                100                 105                 110 aaa gtt aag gag aca ggt gtc atc tgc caa gtc ggc ttt atg aga cgg     384
Lys Val Lys Glu Thr Gly Val Ile Cys Gln Val Gly Phe Met Arg Arg
            115                 120                 125 ttc gat ccc gca tac gca gat gcc aaa cgg cgg atc gac gct gga gaa     432
Phe Asp Pro Ala Tyr Ala Asp Ala Lys Arg Arg Ile Asp Ala Gly Glu
        130                 135                 140 atc ggc aaa cct atc tat tat aaa ggc ttt acg cgc gac caa ggc gcg     480
Ile Gly Lys Pro Ile Tyr Tyr Lys Gly Phe Thr Arg Asp Gln Gly Ala
145                 150                 155                 160 cct ccc gca gaa ttt atc aaa cac agc ggt gga att ttt atc gac tgt     528
Pro Pro Ala Glu Phe Ile Lys His Ser Gly Gly Ile Phe Ile Asp Cys
                165                 170                 175 tcc atc cat gac tat gat att gcc cgt tat ttg cta ggg gcg gaa atc     576
Ser Ile His Asp Tyr Asp Ile Ala Arg Tyr Leu Leu Gly Ala Glu Ile
                180                 185                 190 act tct gtt tca gga cac ggc agg att ctg aac aat ccg ttt atg gag     624
Thr Ser Val Ser Gly His Gly Arg Ile Leu Asn Asn Pro Phe Met Glu
            195                 200                 205 cag tat ggc gat gtg gat cag gcg ctg acg tat att gaa ttt gac tcg     672
Gln Tyr Gly Asp Val Asp Gln Ala Leu Thr Tyr Ile Glu Phe Asp Ser
        210                 215                 220 ggc gca gcg ggg gac gtc gag gca agc aga acc tct cca tac gga cat     720
Gly Ala Ala Gly Asp Val Glu Ala Ser Arg Thr Ser Pro Tyr Gly His
```

```
                225                 230                 235                 240
gac atc cgg gcg gag gtg atc ggg aca gag ggc agt att ttc ata ggg        768
Asp Ile Arg Ala Glu Val Ile Gly Thr Glu Gly Ser Ile Phe Ile Gly
                245                 250                 255 aca ttg aga cat caa cat gtg acc atc cta tcg gct aaa ggg agc agt        816
Thr Leu Arg His Gln His Val Thr Ile Leu Ser Ala Lys Gly Ser Ser
            260                 265                 270 ttt gat atc att cca gac ttt caa act cgt ttt cat gaa gcc tac tgc        864
Phe Asp Ile Ile Pro Asp Phe Gln Thr Arg Phe His Glu Ala Tyr Cys
        275                 280                 285 ttg gag ctt cag cat ttc gcc gag tgt gtc cgg aat gga aaa aca ccg        912
Leu Glu Leu Gln His Phe Ala Glu Cys Val Arg Asn Gly Lys Thr Pro
    290                 295                 300 att gtg act gat att gat gcg acg atc aat tta gaa gtg ggt atc gcc        960
Ile Val Thr Asp Ile Asp Ala Thr Ile Asn Leu Glu Val Gly Ile Ala
305                 310                 315                 320 gca acc aat tcc ttt cga aac ggc atg ccg gta cag cta gat gtg aag        1008
Ala Thr Asn Ser Phe Arg Asn Gly Met Pro Val Gln Leu Asp Val Lys
                325                 330                 335 cgc gct tat aca ggt atg taa                                            1029
Arg Ala Tyr Thr Gly Met
                340
```

<210> SEQ ID NO 71
<211> LENGTH: 342
<212> TYPE: PRT
<213> ORGANISM: Bacillus subtilis

<400> SEQUENCE: 71

```
Met Glu His Gln Val Arg Cys Ala Val Leu Gly Leu Gly Arg Leu Gly
1               5                   10                  15

Tyr Tyr His Ala Lys Asn Leu Val Thr Ser Val Pro Gly Ala Lys Leu
            20                  25                  30

Val Cys Val Gly Asp Pro Leu Lys Gly Arg Ala Glu Gln Val Ala Arg
        35                  40                  45

Glu Leu Gly Ile Glu Lys Trp Ser Glu Asp Pro Tyr Glu Val Leu Glu
    50                  55                  60

Asp Pro Gly Ile Asp Ala Val Ile Val Thr Pro Thr Ser Thr His
65                  70                  75                  80

Gly Asp Met Ile Ile Lys Ala Ala Glu Asn Gly Lys Gln Ile Phe Val
                85                  90                  95

Glu Lys Pro Leu Thr Leu Ser Leu Glu Glu Ser Lys Ala Ala Ser Glu
            100                 105                 110

Lys Val Lys Glu Thr Gly Val Ile Cys Gln Val Gly Phe Met Arg Arg
        115                 120                 125

Phe Asp Pro Ala Tyr Ala Asp Ala Lys Arg Arg Ile Asp Ala Gly Glu
    130                 135                 140

Ile Gly Lys Pro Ile Tyr Tyr Lys Gly Phe Thr Arg Asp Gln Gly Ala
145                 150                 155                 160

Pro Pro Ala Glu Phe Ile Lys His Ser Gly Gly Ile Phe Ile Asp Cys
                165                 170                 175

Ser Ile His Asp Tyr Asp Ile Ala Arg Tyr Leu Leu Gly Ala Glu Ile
            180                 185                 190

Thr Ser Val Ser Gly His Gly Arg Ile Leu Asn Asn Pro Phe Met Glu
        195                 200                 205

Gln Tyr Gly Asp Val Asp Gln Ala Leu Thr Tyr Ile Glu Phe Asp Ser
    210                 215                 220
```

```
Gly Ala Ala Gly Asp Val Glu Ala Ser Arg Thr Ser Pro Tyr Gly His
225                 230                 235                 240

Asp Ile Arg Ala Glu Val Ile Gly Thr Glu Gly Ser Ile Phe Ile Gly
            245                 250                 255

Thr Leu Arg His Gln His Val Thr Ile Leu Ser Ala Lys Gly Ser Ser
        260                 265                 270

Phe Asp Ile Ile Pro Asp Phe Gln Thr Arg Phe His Glu Ala Tyr Cys
            275                 280                 285

Leu Glu Leu Gln His Phe Ala Glu Cys Val Arg Asn Gly Lys Thr Pro
        290                 295                 300

Ile Val Thr Asp Ile Asp Ala Thr Ile Asn Leu Glu Val Gly Ile Ala
305                 310                 315                 320

Ala Thr Asn Ser Phe Arg Asn Gly Met Pro Val Gln Leu Asp Val Lys
                325                 330                 335

Arg Ala Tyr Thr Gly Met
            340

<210> SEQ ID NO 72
<211> LENGTH: 1080
<212> TYPE: DNA
<213> ORGANISM: Bacillus subtilis
<220> FEATURE:
<221> NAME/KEY: CDS
<222> LOCATION: (1)..(1080)

<400> SEQUENCE: 72
```

| | | | | | | | | | | | | | | | | |
|---|---|---|---|---|---|---|---|---|---|---|---|---|---|---|---|---|
| atg ttg ata acg ctt tta aag ggg aga aga aaa gtg gat acg atc aag | | | | | | | | | | | | | | | | 48 |
| Met Leu Ile Thr Leu Leu Lys Gly Arg Arg Lys Val Asp Thr Ile Lys | | | | | | | | | | | | | | | | |
| 1               5                   10                  15 | | | | | | | | | | | | | | | | |
| gtt gga ata tta gga tac gga ttg tcc ggt tct gtt ttt cac ggg ccg | | | | | | | | | | | | | | | | 96 |
| Val Gly Ile Leu Gly Tyr Gly Leu Ser Gly Ser Val Phe His Gly Pro | | | | | | | | | | | | | | | | |
|                 20                  25                  30 | | | | | | | | | | | | | | | | |
| ctg ctg gat gtt ctg gat gaa tat caa atc agc aaa atc atg aca tca | | | | | | | | | | | | | | | | 144 |
| Leu Leu Asp Val Leu Asp Glu Tyr Gln Ile Ser Lys Ile Met Thr Ser | | | | | | | | | | | | | | | | |
|             35                  40                  45 | | | | | | | | | | | | | | | | |
| cgg aca gaa gaa gtg aaa cgg gat ttt cca gat gct gag gtt gta cat | | | | | | | | | | | | | | | | 192 |
| Arg Thr Glu Glu Val Lys Arg Asp Phe Pro Asp Ala Glu Val Val His | | | | | | | | | | | | | | | | |
| 50                  55                  60 | | | | | | | | | | | | | | | | |
| gag ctt gaa gaa atc aca aat gac cct gcc att gag ctt gtc att gtc | | | | | | | | | | | | | | | | 240 |
| Glu Leu Glu Glu Ile Thr Asn Asp Pro Ala Ile Glu Leu Val Ile Val | | | | | | | | | | | | | | | | |
| 65                  70                  75                  80 | | | | | | | | | | | | | | | | |
| acc acc ccg agc ggc ctt cat tac gag cat act atg gca tgc ata cag | | | | | | | | | | | | | | | | 288 |
| Thr Thr Pro Ser Gly Leu His Tyr Glu His Thr Met Ala Cys Ile Gln | | | | | | | | | | | | | | | | |
|                 85                  90                  95 | | | | | | | | | | | | | | | | |
| gcc gga aaa cat gtt gtg atg gaa aaa cca atg aca gca acg gcc gaa | | | | | | | | | | | | | | | | 336 |
| Ala Gly Lys His Val Val Met Glu Lys Pro Met Thr Ala Thr Ala Glu | | | | | | | | | | | | | | | | |
|             100                 105                 110 | | | | | | | | | | | | | | | | |
| gag ggg gaa aca tta aaa agg gct gcc gat gaa aaa ggc gta tta tta | | | | | | | | | | | | | | | | 384 |
| Glu Gly Glu Thr Leu Lys Arg Ala Ala Asp Glu Lys Gly Val Leu Leu | | | | | | | | | | | | | | | | |
|             115                 120                 125 | | | | | | | | | | | | | | | | |
| agc gta tat cat aac cga cgc tgg gat aac gat ttt tta acg att aaa | | | | | | | | | | | | | | | | 432 |
| Ser Val Tyr His Asn Arg Arg Trp Asp Asn Asp Phe Leu Thr Ile Lys | | | | | | | | | | | | | | | | |
|         130                 135                 140 | | | | | | | | | | | | | | | | |
| aag ctg atc tct gag gga tcc ctt gaa gat atc aat aca tat caa gtt | | | | | | | | | | | | | | | | 480 |
| Lys Leu Ile Ser Glu Gly Ser Leu Glu Asp Ile Asn Thr Tyr Gln Val | | | | | | | | | | | | | | | | |
| 145                 150                 155                 160 | | | | | | | | | | | | | | | | |
| tcc tat aac cgc tac aga cct gaa gtt caa gcg cgg tgg cgg gaa aaa | | | | | | | | | | | | | | | | 528 |
| Ser Tyr Asn Arg Tyr Arg Pro Glu Val Gln Ala Arg Trp Arg Glu Lys | | | | | | | | | | | | | | | | |
|                 165                 170                 175 | | | | | | | | | | | | | | | | |

```
gaa ggc act gcc act ggt acg ctg tat gat ctc ggc tcc cac atc ata       576
Glu Gly Thr Ala Thr Gly Thr Leu Tyr Asp Leu Gly Ser His Ile Ile
            180                 185                 190 gac caa acc ctg cat ttg ttt ggg atg cct aaa gcc gtg act gca aac       624
Asp Gln Thr Leu His Leu Phe Gly Met Pro Lys Ala Val Thr Ala Asn
        195                 200                 205 gtg atg gcc cag cgg gaa aat gcc gaa acg gtt gac tat ttt cat tta       672
Val Met Ala Gln Arg Glu Asn Ala Glu Thr Val Asp Tyr Phe His Leu
    210                 215                 220 acc ctg gat tat ggc aag ctt caa gcc att cta tac gga gga tca atc       720
Thr Leu Asp Tyr Gly Lys Leu Gln Ala Ile Leu Tyr Gly Gly Ser Ile
225                 230                 235                 240 gtt ccg gca aac gga cct cgt tat caa atc cat gga aaa gat tct agc       768
Val Pro Ala Asn Gly Pro Arg Tyr Gln Ile His Gly Lys Asp Ser Ser
                245                 250                 255 ttt atc aaa tat gga att gac gga cag gaa gac gca ctc aga gcg gga       816
Phe Ile Lys Tyr Gly Ile Asp Gly Gln Glu Asp Ala Leu Arg Ala Gly
            260                 265                 270 aga aaa cca gag gat gac agc tgg ggt gcg gat gtt ccg gag ttt tac       864
Arg Lys Pro Glu Asp Asp Ser Trp Gly Ala Asp Val Pro Glu Phe Tyr
        275                 280                 285 gga aag ctt aca acc att cgt ggc tcc gac aaa aaa aca gaa acg att       912
Gly Lys Leu Thr Thr Ile Arg Gly Ser Asp Lys Lys Thr Glu Thr Ile
    290                 295                 300 cca tca gta aat ggc tcc tac ctt act tat tac cgt aaa ata gcg gaa       960
Pro Ser Val Asn Gly Ser Tyr Leu Thr Tyr Tyr Arg Lys Ile Ala Glu
305                 310                 315                 320 agc ata cga gaa ggt gct gcg ctg cca gtc act gct gag gaa ggt att      1008
Ser Ile Arg Glu Gly Ala Ala Leu Pro Val Thr Ala Glu Glu Gly Ile
                325                 330                 335 aat gtc atc cgc atc att gaa gcc gcg atg gaa agc agt aaa gag aaa      1056
Asn Val Ile Arg Ile Ile Glu Ala Ala Met Glu Ser Ser Lys Glu Lys
            340                 345                 350 cga acc att atg ctg gag cac taa                                      1080
Arg Thr Ile Met Leu Glu His
        355
```

<210> SEQ ID NO 73
<211> LENGTH: 359
<212> TYPE: PRT
<213> ORGANISM: Bacillus subtilis

<400> SEQUENCE: 73

```
Met Leu Ile Thr Leu Leu Lys Gly Arg Arg Lys Val Asp Thr Ile Lys
1               5                   10                  15

Val Gly Ile Leu Gly Tyr Gly Leu Ser Gly Ser Val Phe His Gly Pro
            20                  25                  30

Leu Leu Asp Val Leu Asp Glu Tyr Gln Ile Ser Lys Ile Met Thr Ser
        35                  40                  45

Arg Thr Glu Glu Val Lys Arg Asp Phe Pro Asp Ala Glu Val Val His
    50                  55                  60

Glu Leu Glu Glu Ile Thr Asn Asp Pro Ala Ile Glu Leu Val Ile Val
65                  70                  75                  80

Thr Thr Pro Ser Gly Leu His Tyr Glu His Thr Met Ala Cys Ile Gln
                85                  90                  95

Ala Gly Lys His Val Val Met Glu Lys Pro Met Thr Thr Ala Glu
            100                 105                 110

Glu Gly Glu Thr Leu Lys Arg Ala Ala Asp Glu Lys Gly Val Leu Leu
```

|  | 115 |  |  |  | 120 |  |  |  | 125 |  |  |  |  |  |
|--|--|--|--|--|--|--|--|--|--|--|--|--|--|--|

Ser Val Tyr His Asn Arg Arg Trp Asp Asn Asp Phe Leu Thr Ile Lys
          130                  135                  140

Lys Leu Ile Ser Glu Gly Ser Leu Glu Asp Ile Asn Thr Tyr Gln Val
145                  150                  155                160

Ser Tyr Asn Arg Tyr Arg Pro Glu Val Gln Ala Arg Trp Arg Glu Lys
          165                  170                  175

Glu Gly Thr Ala Thr Gly Thr Leu Tyr Asp Leu Gly Ser His Ile Ile
              180                  185                190

Asp Gln Thr Leu His Leu Phe Gly Met Pro Lys Ala Val Thr Ala Asn
          195                  200                205

Val Met Ala Gln Arg Glu Asn Ala Glu Thr Val Asp Tyr Phe His Leu
210                  215                  220

Thr Leu Asp Tyr Gly Lys Leu Gln Ala Ile Leu Tyr Gly Gly Ser Ile
225                  230                  235                240

Val Pro Ala Asn Gly Pro Arg Tyr Gln Ile His Gly Lys Asp Ser Ser
          245                  250                  255

Phe Ile Lys Tyr Gly Ile Asp Gly Gln Glu Asp Ala Leu Arg Ala Gly
              260                  265                270

Arg Lys Pro Glu Asp Asp Ser Trp Gly Ala Asp Val Pro Glu Phe Tyr
          275                  280                285

Gly Lys Leu Thr Thr Ile Arg Gly Ser Asp Lys Lys Thr Glu Thr Ile
290                  295                  300

Pro Ser Val Asn Gly Ser Tyr Leu Thr Tyr Tyr Arg Lys Ile Ala Glu
305                  310                  315                320

Ser Ile Arg Glu Gly Ala Ala Leu Pro Val Thr Ala Glu Glu Gly Ile
          325                  330                335

Asn Val Ile Arg Ile Ile Glu Ala Ala Met Glu Ser Ser Lys Glu Lys
          340                  345                350

Arg Thr Ile Met Leu Glu His
          355

<210> SEQ ID NO 74
<211> LENGTH: 656
<212> TYPE: DNA
<213> ORGANISM: Pseudomonas abietaniphila AKC-019

<400> SEQUENCE: 74

```
tactttgacg gcaggtctac acatgcagtc gagcggatga gggagcttgc tccctgattc    60
agcggcggac gggtgagtat gcctaggaat ctgcctggta gtgggggaca acgtctcgaa   120
agggacgcta ataccgcata cgtcctacgg gagaaagtgg gggatcttcg gacctcacgc   180
tatcagatga gcctaggtcg gattagctag ttggtgaggt aatggctcac caaggcgacg   240
atccgtaact ggtctgagag gatgatcagt cacactggaa ctgagacacg gtccagactc   300
ctacgggagg cagcagtggg gaatattgga caatgggcga agcctgatca gccatgccg   360
cgtgtgtga agaaggtctt cggattgtaa agcactttaa gttgggagga agggcattaa   420
cctaatacgt tagtgttttg acgttaccga cagaataagc accggctaac tctgtgccag   480
cagccgcggt aatacagagg gtgcaagcgt taatcggaat tactgggcgt aaagcgcgcg   540
taggtggttt gttaagttga atgtgaaatc cccgggctca acctgggaac tgcatccaaa   600
ctggcaagct agagtagggc agagggtggt ggaatttcct gtgtagcggt gaaatg       656
```

<210> SEQ ID NO 75

```
<211> LENGTH: 577
<212> TYPE: DNA
<213> ORGANISM: Burkholderia terrae AKC-020

<400> SEQUENCE: 75
ttcttgggcg gctgccttcc atgcagtcga cggcagcgcg ggggcaccct ggcggcgaag      60
tggcgaacgg gtgagtatac atcggacgtg tcctggagtg ggggatagcc cggcgaaagc     120
cggattaata ccgcatacga tcctgggatg aaagcggggg accgaaaggc ctcgcgctca     180
aggggcggcc gatggcagat tagctagttg gtggggtaaa ggcctaccaa ggcgacgatc     240
tgtagctggt ctgagaggac gaccagccac actgggactg agacacgccc agactccta     300 cgggaggcag cagtggggaa ttttggacaa tgggggcaac cctgatccag caatgccgcg     360
tgtgtgaaga aggccttcgg ggttgtaaag cacttttgtc cggaaagaaa acctccgtcc     420
taatacggtg gggggatga cggtaccgga agaataagca ccggctaact acgtgccagc      480
agccgcggta atacgtaggg tgcaagcgtt aatcggaatt actgggcgta aagcgtgcgc     540
aggcggttcg ctaagaccga tgtgaaatcc ccgggct                              577

<210> SEQ ID NO 76
<211> LENGTH: 552
<212> TYPE: DNA
<213> ORGANISM: Pseudomonas sp.

<400> SEQUENCE: 76
gacctgggcg gcaggcctaa ccatgcagtc gagcggatga caggagcttg ctcctgattc      60
agcggcggac gggtgagtat gcctaggaat ctgcctggta gtgggggaca acgtttcgaa     120
aggaacgcta ataccgcata cgtcctacgg gagaaagcag gggaccttcg ggccttgcgc     180
tatcagatga gcctaggtcg gattagctag ttggtgaggt aatggctcac caaggcgacg     240
atccgtaact ggtctgagag gatgatcagt cacactggaa ctgagacacg gtccagactc     300
ctacgggagg cagcagtggg gaatattgga caatgggcga agcctgatc cagccatgcc      360 gcgtgtgtga agaaggtctt cggattgtaa agcactttaa gttgggagga agggcagtaa     420
attaatactt tgctgttttg acgttaccga cagaataagc accggctaac tctgtgccag     480
cagccgcggt aatacagagg gtgcaagcgt taatcggaat tactgggcgt aaagcgcgcg     540
taggtggttt gt                                                          552

<210> SEQ ID NO 77
<211> LENGTH: 551
<212> TYPE: DNA
<213> ORGANISM: Pseudomonas sp.

<400> SEQUENCE: 77 caccettggc gcaggtctac acatgcagtc gagcggcagc cgggtacttg tacctggtgg      60
cgagcggcgg acgggtgagt atgcctagga tctgcctggt agtgggggat gacgttcgga     120
aacgaacgct aataccgcat acgtcctacg ggagaagcag gggaccttcg ggccttgcgc     180
tatcagatga gcctaggtcg gattagctag ttggtgaggt aatggctcac caaggcgacg     240
atccgtaact ggtctgagag gatgatcagt cacactggaa ctgagacacg gtccagactc     300
ctacaggagg cagcagtggg gaatattgga caatgggcga agcctgatc cagccatgcc      360 gcgtgtgtga agaaggtctt cggattgtaa agcactttaa gttgggagga agggcagtta     420
cctaatacgt gattgttttg acgttaccga cagaataagc accggctaac tctgtgccag     480
cagccgcggt aatacagagg gtgcaagcgt taatcggaat tactgggcgt aaagcgcgcg     540
```

```
taggtggttc g                                                           551

<210> SEQ ID NO 78
<211> LENGTH: 558
<212> TYPE: DNA
<213> ORGANISM: Pseudomonas sp.

<400> SEQUENCE: 78
gcctgggcgc aggtctacca tgcagtcgag cggcagcacg ggtacttgta cctggtggcg      60
agcggcggac gggtgagtaa tgcctaggaa tctgcctggt agtgggggat aacgttcgga     120
aacgaacgct aataccgcat acgtcctacg ggagaaagca ggggaccttc gggccttgcg     180
ctatcagatg agcctaggtc ggattagcta gttggtgagg taatggctca ccaaggcgac     240
gatccgtaac tggtctgaga ggatgatcag tcacactgga actgagacac ggtccagact     300
cctacgggag gcagcagtgg ggaatattgg acaatgggcg aaagcctgat ccagccatgc     360
cgcgtgtgtg aagaaggtct tcggattgta aagcacttta agttgggagg aagggcagtt    420
acctaatacg tgattgtttt gacgttaccg acagaataag caccggctaa ctctgtgcca     480
gcagccgcgg taatacagag ggtgcaagcg ttaatcggaa ttactgggcg taaagcgcgc     540
gtaggtggtt cgttaagt                                                   558

<210> SEQ ID NO 79
<211> LENGTH: 563
<212> TYPE: DNA
<213> ORGANISM: Pseudomonas sp.

<400> SEQUENCE: 79
tccctgggcg gcagcctaac catgcagtcg agcggatgac agagagcttg ctcctggatt     60
cagcggcgga cgggtgagta atgcctagga atctgcctgg tagtggggga caacgtttcg    120
aaaggaacgc taataccgca tacgtcctac gggagaaagc aggggacctt cgggccttgc    180
gctatcagat gagcctaggt cggattagct agttggtgag gtaatggctc accaaggcga    240
cgatccgtaa ctggtctgag aggatgatca gtcacactgg aactgagaca cggtccagac    300
tcctacggga ggcagcagtg gggaatattg gacaatgggc gaaagcctga tccagccatg    360
ccgcgtgtgt gaagaaggtc ttcggattgt aaagcacttt aagttgggag gaagggcagt    420
aaattaatac tttgctgttt tgacgttacc gacagaataa gcaccggcta actctgtgcc    480
agcagccgcg gtaatacaga ggtgttttat gcgtttaatc ggaattactg ggcgtaaagc    540
gcgcgtaggt ggttttgtta agt                                            563

<210> SEQ ID NO 80
<211> LENGTH: 649
<212> TYPE: DNA
<213> ORGANISM: Pseudomonas sp.

<400> SEQUENCE: 80
taattggccg gcagtctaac catgcagtcg agcggatgac gggagcttgc tcccgaattc     60
agcggcggac gggtgagtat gcctaggaat ctgcctggta gtgggggaca acgtctcgaa    120
agggacgcta ataccgcata cgtcctacgg agaaagtggg ggatcttcg  acctcacgc     180 tatcagatga gcctaggtcg gattagctag ttggtgaggt aatggctcac caaggcgacg    240
atccgtaact ggtctgagag gatgatcagt cacactggaa ctgagacacg gtccagactc    300
ctacgggagg cagcagtggg gaatattgga caatgggcga aagcctgatc cagccatgcc    360
```

```
gcgtgtgtga agaaggtctt cggattgtaa agcactttaa gttgggagga agggcattaa     420
cctaatacgt tgatgttttg acgttaccga cagaataagc accggctaac tctgtgccag     480
cagccgcggt aatacagagg gtgcaagcgt taatcggaat tactgggcgt aaagcgcgcg     540
taggtggttt gttaagttgg atgtgaaagc cccgggctca acctgggaac tgcatccaaa     600
actggcaagc tagagtaggg cagagggtgg tggaatttcc tgtgtagcg                 649

<210> SEQ ID NO 81
<211> LENGTH: 555
<212> TYPE: DNA
<213> ORGANISM: Burkholderia sediminicola

<400> SEQUENCE: 81
gccctgggcg cctgccttaa catgcagtcg acggcagcac gggagcaatc ctggtggcga      60
gtggcgaacg ggtgagtaat acatcggaac gtgtcctgta gtggggata gcccggcgaa     120 agccggatta ataccgcata cgctctacgg aggaaagggg gggatcttag gacctcccgc     180
tacaggggcg gccgatggca gattagctag ttggtggggt aaaggcctac caaggcgacg     240
atctgtagct ggtctgagag gacgaccagc cacactggga ctgagacacg gcccagactc     300
ctacgggagg cagcagtggg gaattttgga caatgggcga agcctgatc cagcaatgcc     360 gcgtgtgtga agaaggcctt cgggttgtaa agcacttttg tccggaaaga aaacctccgc     420
cctaatatgg tgggggatg acggtaccgg aagaataagc accggctaac tacgtgccag     480
cagccgcggt aatacgtagg gtgcaagcgt taatcggaat tactgggcgt aaagcgtgcg     540
caggcggtcc gctaa                                                     555

<210> SEQ ID NO 82
<211> LENGTH: 615
<212> TYPE: DNA
<213> ORGANISM: Burkholderia terrae

<400> SEQUENCE: 82
tcaccttggc cggcatgctt cacatgcagt cgacggcagc gcggggcac cctggtggcg      60 agtggcgaac gggtgagtat acatcggaac gtgtcctgga gtggggata gcccggcgaa     120 agccggatta ataccgcata cgatctcagg atgaaagcgg gggaccgaaa ggcctcgcgc     180
tcaaggggcg gccgatggca gattagctag ttggtgggt aaaggcctac caaggcgacg     240
atctgtagct ggtctgagag gacgaccagc cacactggga ctgagacacg gcccagactc     300
ctacgggagg cagcagtggg gaattttgga caatgggggc aaccctgatc cagcaatgcc     360
gcgtgtgtga agaaggcctt cgggttgtaa agcacttttg tccggaaaga aaacctccgt     420
cctaatacgg tgggggatg acggtaccgg aagaataagc accggctaac tacgtgccag     480
cagccgcggt aatacgtagg gtgcaagcgt taatcggaat tactgggcgt aaagcgtgcg     540
caggcggttc gctaagaccg atgtgaaatc cccgggctta acctgggaac tgcattggtg     600
actggcgggc tagag                                                     615

<210> SEQ ID NO 83
<211> LENGTH: 668
<212> TYPE: DNA
<213> ORGANISM: Burkholderia sp.

<400> SEQUENCE: 83
tccccttggc ggcatgcctt ccatgcagtc gacggcagca cggggggcaac cctggtggcg      60 agtggcgaac gggtgagtat acatcggaac gtgtcctgga gtgggggata gcccggcgaa     120
```

```
agccggatta ataccgcata cgatccctgg atgaaagcgg gggaccgaaa ggcctcgcgc    180
tcaaggggcg gccgatggca gattagctag ttggtggggt aaaggcctac caaggcgacg    240
atctgtagct ggtctgagag gacgaccagc cacactggga ctgagacacg gcccagactc    300
ctacgggagg cagcagtggg gaattttgga caatgggggc aaccctgatc cagcaatgcc    360
gcgtgtgtga agaaggcctt cgggttgtaa agcacttttg tccggaaaga aaacctccgt    420
cctaatacgg tgggggatg acggtaccgg aagaataagc accggctaac tacgtgccag     480
cagccgcggt aatacgtagg gtgcaagcgt taatcggaat tactgggcgt aaagcgtgcg    540
caggcggttc gctaagaccg atgtgaaatc cccgggctta acctgggaac tgcattggtg    600
actggcgggc tagagtatgg cagaggggg tagaatttcc acgtgtagca gtgaaatgcg     660
tagagatg                                                             668

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
agagtttgat cctggctcag                                                  20

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
acggctacct tgttacgact t                                                21

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
agagtttgat cctggctcag                                                  20
```

2-DEOXY-SCYLLO-INOSOSE REDUCTASE

SEQUENCE LISTING SUBMISSION VIA EFS-WEB

A computer readable text file, entitled "SequenceListing.txt," created on or about Feb. 3, 2016 with a file size of about 102 kb contains the sequence listing for this application and is hereby incorporated by reference in its entirety.

TECHNICAL FIELD

The present invention relates to a novel 2-deoxy-scyllo-inosose reductase and a gene for encoding this enzyme. The present invention also relates to a method for producing (−)-vibo-quercitol using an enzyme capable of converting 2-deoxy-scyllo-inosose directly into (−)-vibo-quercitol.

BACKGROUND ART (−)-Vibo-quercitol ((1R,2R,4S,5R)-cyclohexane-1,2,3,4,5-pentol) is a compound having the following chemical structure discovered from plants of the Asclepiadaceae family.

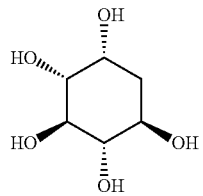

[Chemical formula 1]

(−)-Vibo-quercitol has been shown to have a potent hypoglycemic action. Deoxyinosamine and deoxyinosamidine [sic], which can be obtained by amination of (−)-vibo-quercitol, are also compounds that can serve as synthesis intermediates for various pharmaceuticals and agricultural chemicals (Patent References 1 and 2).

The industrial utility of (−)-vibo-quercitol has also become apparent in recent years. For example, Patent Reference 3 describes (−)-vibo-quercitol as being useful as an additive for preventing freezing of the coolant in a fuel cell. When used for this purpose, (−)-vibo-quercitol is not oxidized even after long-term use and maintains suitable properties.

Patent Reference 4 focuses on the fact that (−)-vibo-quercitol can absorb and emit a large amount of latent heat during the process of dissolution and solidification, and discloses the application of this compound to a heat-storage material for the heat storage of solar heat and for efficiently utilizing inexpensive nighttime power.

A clear need therefore exists to produce (−)-vibo-quercitol efficiently by a simple process. When (−)-vibo-quercitol is utilized as an active ingredient of a pharmaceutical, the bulk form of the compound should be as pure as possible and should not include any unidentified impurities. The production process should therefore also be as simple as possible, and the production history should be easily tracked. The production cost can also affect the feasibility of the technology when (−)-vibo-quercitol is used for industrial purposes such as those mentioned above.

Classically, (−)-vibo-quercitol is extracted from plants of the Asclepiadaceae family. However, a method of culturing microorganisms of the genus *Agrobacterium* or genus *Salmonella* using myo-inositol as a substrate, causing (−)-vibo-quercitol to be produced together with (+)-proto-quercitol and (+)-epi-quercitol in the culture broth, and isolating (−)-vibo-quercitol from the culture broth has been proposed in recent years as a more efficient method. A method of bringing cells of these microorganisms of the genus *Agrobacterium* or genus *Salmonella* into contact with myo-inositol, causing (−)-vibo-quercitol to be produced together with (+)-proto-quercitol and (+)-epi-quercitol in the reaction solution, and isolating (−)-vibo-quercitol from the reaction solution has also been proposed (Patent References 1 and 2).

However, no enzyme that converts myo-inositol into (−)-vibo-quercitol in this method has been isolated, and it is not even clear whether the reaction is due to one enzyme or whether two or more enzymes are involved. Therefore, since culturing microorganism with myo-inositol as a substrate or at least utilizing cells obtained from a culture of these microorganisms is essential in this method, the process remains complex and is associated with the risk of contamination by unknown impurities.

Patent Reference 5 also proposes a method for culturing *Enterobacter* sp. AB10114 (FERM P-19319), a microorganism of the genus *Enterobacter*, using myo-inositol as a substrate, causing (−)-vibo-quercitol to be produced in the culture broth, and isolating (−)-vibo-quercitol from the culture broth. (−)-Vibo-quercitol is obtained at a yield of about 25% from myo-inositol in this method (see Example 1). In this method again, however, no enzyme that converts myo-inositol into (−)-vibo-quercitol has been isolated. Therefore, since culturing microorganisms with myo-inositol as a substrate is essential in this method as well, the process again is complex and associated with a risk of contamination by unknown impurities. In addition, even this method cannot avoid a microbial fermentation process requiring time and effort to obtain the target (−)-vibo-quercitol.

Furthermore, Patent Reference 6 discloses a method for converting (−)-vibo-quercitol into 2-deoxy-scyllo-inosose by contact with the *Enterobacter* sp. AB10114 (FERM P-19319) used in the method of the abovementioned Patent Reference 5. In brief, *Enterobacter* sp. AB10114 (FERM P-19319) is said to convert (−)-vibo-quercitol into 2-deoxy-scyllo-inosose at a yield of 80% (see Example 1). Although the details are not clear since no enzyme is isolated either in Patent Reference 6, it is reasonable to assume that, even if this reaction is catalyzed by a single enzyme, the activity of at least that enzyme is predominant in the direction converting (−)-vibo-quercitol into 2-deoxy-scyllo-inosose, and it is difficult for a substantially reverse reaction to progress.

On the other hand, the inventors do not know of any enzyme previously reported to convert 2-deoxy-scyllo-inosose directly into (−)-vibo-quercitol as shown in the following reaction scheme.

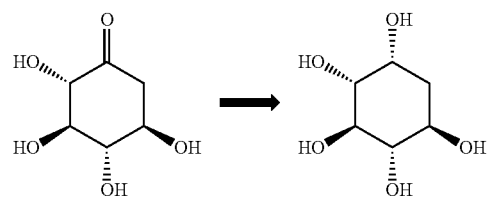

[Chemical formula 2]

2-Deoxy-scyllo-inosose → (−)-vibo-quercitol

PRIOR ART REFERENCES

Patent References

Patent Reference 1: Japanese Laid-Open Patent Application 11-12210
Patent Reference 2: Japanese Laid-Open Patent Application 2000-4890
Patent Reference 3: International Publication WO2005/091413 pamphlet
Patent Reference 4: Japanese Laid-Open Patent Application 2010-215876
Patent Reference 5: Japanese Laid-Open Patent Application 2005-70
Patent Reference 6: Japanese Laid-Open Patent Application 2005-72

SUMMARY OF THE INVENTION

Problems to be Solved by the Invention

Therefore, the purpose of the present invention is to produce (−)-vibo-quercitol efficiently by a simple process. Production by a simple process minimizes the risk of impurity contamination. Efficient production is expected to also permit utilization of (−)-vibo-quercitol in the industrial field.

Particularly intended is the utilization of an enzyme capable of converting 2-deoxy-scyllo-inosose directly into (−)-vibo-quercitol. In brief, 2-deoxy-scyllo-inosose (sometimes abbreviated as "DOI" hereinafter) is known to be produced easily by fermentation via only a two-step enzymatic reaction from glucose (WO2010/109916 pamphlet, WO10/053052 pamphlet, and WO06/109479 pamphlet, etc.), and is expected to be able to serve as an extremely inexpensive raw material.

Means Used to Solve the Above-Mentioned Problems

The inventors screened microorganisms having the ability to produce (−)-vibo-quercitol and discovered microorganisms capable of converting 2-deoxy-scyllo-inosose into (−)-vibo-quercitol. The inventors also succeeded in isolating an enzyme having catalytic activity to convert 2-deoxy-scyllo-inosose directly into (−)-vibo-quercitol from these microorganisms. The inventors also elucidated the amino acid sequence of this enzyme and the base sequence encoding it. Therefore, the first aspect of the present invention includes the following.

(1) A 2-deoxy-scyllo-inosose reductase having the following properties (a) through (c), derived from a microorganism having the ability to utilize (−)-vibo-quercitol:

(a) the enzyme has catalytic activity to convert 2-deoxy-scyllo-inosose into (−)-vibo-quercitol;
(b) the enzyme presents maximum activity at pH 7.0-9.0; and
(c) the molecular mass of a polypeptide moiety of the enzyme measured by SDS-polyacrylamide electrophoresis is 36 kDa.

(2) The 2-deoxy-scyllo-inosose reductase of (1) above wherein the microorganism belongs to the genus *Pseudomonas* or the genus *Burkholderia*.

(3) A protein of any of (a) through (e) below:

(a) a protein comprising an amino acid sequence represented by SEQ ID NO: 2;
(b) a protein comprising an amino acid sequence having 58% or greater identity to an amino acid sequence represented by SEQ ID NO: 2 and having 2-deoxy-scyllo-inosose reductase activity;
(c) a protein comprising an amino acid sequence having 56% or greater identity to an amino acid sequence represented by SEQ ID NO: 4 and having 2-deoxy-scyllo-inosose reductase activity;
(d) a protein comprising an amino acid sequence having 54% or greater identity to an amino acid sequence represented by SEQ ID NO: 6 and having 2-deoxy-scyllo-inosose reductase activity;
(e) a protein comprising an amino acid sequence having 54% or greater identity to an amino acid sequence represented by SEQ ID NO: 8 and having 2-deoxy-scyllo-inosose reductase activity.

(4) The protein of (3) above wherein the protein is any one of (b) through (e), excluding proteins comprising amino acid sequences represented by SEQ ID NOS: 2, 4, 6, and 8.

(5) A gene encoding a protein described in (3) or (4) above.

(6) A gene comprising a nucleotide sequence of (a) or (b) below:

(a) a nucleotide sequence represented by SEQ ID NO: 1; or
(b) a nucleotide sequence hybridizing under stringent conditions with DNA comprising a sequence complementary to a nucleotide sequence comprising at least 18 consecutive bases in a nucleotide sequence represented by SEQ ID NO: 1 and encoding a protein having 2-deoxy-scyllo-inosose reductase activity.

(7) The gene of (6) above wherein the nucleotide sequence comprising at least 18 consecutive bases in (b) is all or part of a sequence selected from the group comprising SEQ ID NO: 9, SEQ ID NO: 11, SEQ ID NO: 13, SEQ ID NO: 15, SEQ ID NO: 17, SEQ ID NO: 19, SEQ ID NO: 21, and SEQ ID NO: 23.

The present invention also provides a method for producing an enzyme having catalytic activity to convert 2-deoxy-scyllo-inosose directly into (−)-vibo-quercitol. Therefore, the second aspect of the present invention intends the following.

(8) A recombinant vector for (−)-vibo-quercitol conversion including a gene of any of (5) through (7) above.

(9) A transformant for (−)-vibo-quercitol conversion having the gene of any of (5) through (7) above or a recombinant vector of (8) above introduced.

(10) A method for producing 2-deoxy-scyllo-inosose reductase characterized in that the transformant of (9) above is cultured for a time and under conditions suited to the production of a protein having 2-deoxy-scyllo-inosose reductase activity, and the protein is purified and recovered from the culture.

The present invention also provides a method for producing (−)-vibo-quercitol using the above enzyme. With respect to this production process, the inventors conducted an amino acid sequence homology search with the 2-deoxy-scyllo-inosose reductase of the present invention discovered for the first time by the inventors, and as a result discovered several proteins previously assumed to have inositol 2-dehydrogenase activity to present high amino acid identity with the novel 2-deoxy-scyllo-inosose of the present invention and to have catalytic activity to convert 2-deoxy-scyllo-inosose directly into (−)-vibo-quercitol. As far as the inventors know, these proteins have not been reported to have catalytic activity convert 2-deoxy-scyllo-inosose directly into (−)-vibo-quercitol.

Therefore, the third aspect of the present invention is as follows.

(11) A method for producing (−)-vibo-quercitol characterized in that the 2-deoxy-scyllo-inosose reductase of (1) or (2) above is brought into contact with 2-deoxy-scyllo-inosose, reacted under conditions of pH 5.0-10.0, and the (−)-vibo-quercitol produced is recovered from the reaction solution.

(12) A method for producing (−)-vibo-quercitol characterized in that a protein of any one of (a) through (e) below:

(a) a protein comprising an amino acid sequence represented by SEQ ID NO: 2;

(b) a protein comprising an amino acid sequence having 58% or greater identity to an amino acid sequence represented by SEQ ID NO: 2 and having 2-deoxy-scyllo-inosose reductase activity;

(c) a protein comprising an amino acid sequence having 56% or greater identity to an amino acid sequence represented by SEQ ID NO: 4 and having 2-deoxy-scyllo-inosose reductase activity;

(d) a protein comprising an amino acid sequence having 54% or greater identity to an amino acid sequence represented by SEQ ID NO: 6 and having 2-deoxy-scyllo-inosose reductase activity; or (e) a protein comprising an amino acid sequence having 54% or greater identity to an amino acid sequence represented by SEQ ID NO: 8 and having 2-deoxy-scyllo-inosose reductase activity, is brought into contact with 2-deoxy-scyllo-inosose, reacted under conditions of pH 5.0-10.0, and the (−)-vibo-quercitol produced is recovered from the reaction solution.

The present invention also provides a method for converting 2-deoxy-scyllo-inosose into (−)-vibo-quercitol using the above enzyme. Therefore, the fourth aspect of the present invention is as follows.

(13) A method for converting 2-deoxy-scyllo-inosose into (−)-vibo-quercitol characterized in that the 2-deoxy-scyllo-inosose reductase described in (1) or (2) above is brought into contact with 2-deoxy-scyllo-inosose and reacted under conditions of pH 5.0-10.0.

(14) A method for converting 2-deoxy-scyllo-inosose into (−)-vibo-quercitol characterized in that a protein of any one of (a) through (e) below:

(a) a protein comprising an amino acid sequence represented by SEQ ID NO: 2;

(b) a protein comprising an amino acid sequence having 58% or greater identity to an amino acid sequence represented by SEQ ID NO: 2 and having 2-deoxy-scyllo-inosose reductase activity;

(c) a protein comprising an amino acid sequence having 56% or greater identity to an amino acid sequence represented by SEQ ID NO: 4 and having 2-deoxy-scyllo-inosose reductase activity;

(d) a protein comprising an amino acid sequence having 54% or greater identity to an amino acid sequence represented by SEQ ID NO: 6 and having 2-deoxy-scyllo-inosose reductase activity; or (e) a protein comprising an amino acid sequence having 54% or greater identity to an amino acid sequence represented by SEQ ID NO: 8 and having 2-deoxy-scyllo-inosose reductase activity, is brought into contact with 2-deoxy-scyllo-inosose and reacted under conditions of pH 5.0-10.0.

Advantages of the Invention

The present invention provides an enzyme catalyzing a novel reaction. The use of the enzyme of the present invention makes it possible to produce (−)-vibo-quercitol simply and efficiently.

BRIEF DESCRIPTION OF THE DRAWINGS

FIG. 1 shows a 16SrRNA gene sequence of a microorganism confirmed to have the ability to convert 2-deoxy-scyllo-inosose into (−)-vibo-quercitol.

FIG. 4 shows known inositol dehydrogenase sequences (the GenBank Accession No. is shown to the left of each sequence), the N-terminal amino acid sequence of the DOI reductase of the present invention (DOI reductase Nterm), and the alignment of the internal sequence of the DOI reductase of the present invention (DOI reductase internal). Also shown are the positions of the various primers used to obtain the DOI reductase gene of the present invention. Parts having high sequence homology are surrounded by a frame in the alignment. An arrow to the right (→) shows the position of a sense strand direction primer; an arrow to the left (←) shows the position of an antisense strand direction primer. Furthermore, the numbers in circles in the figure correspond to the numbers in hard brackets in the text.

FIG. 5 shows the thermal cycle conditions in PCR used to amplify the DOI reductase gene of the present invention. The upper row is the gradient PCR conditions; the lower row is the TAIL-PCR conditions.

FIG. 8 is an alignment of the amino acid sequence of a 2-deoxy-scyllo-inosose reductase produced by strain AKC-020 and the amino acid sequences of GenBank Accession No. EKS70356.1, GenBank Accession No. ADU72508.1, and GenBank Accession No. EIK69154.1, which are known inositol dehydrogenases. These known inositol dehydrogenases have not been reported to date to have catalytic activity to convert 2-deoxy-scyllo-inosose into (−)-vibo-quercitol.

FIG. 9 shows the amino acid sequence and nucleotide sequence of the coding region of an inositol dehydrogenase gene (GenBank Accession No. AAG44816.1) that has been clarified to have low sequence identity with the amino acid sequence of DOI reductase from strain AKC-020 of the present invention and low ability to convert 2-deoxy-scyllo-inosose into (−)-vibo-quercitol.

FIG. 10 shows the amino acid sequence and nucleotide sequence of the coding region of an inositol dehydrogenase gene (GenBank Accession No. CAB12924.1) that has been clarified to have low sequence identity with the amino acid sequence of DOI reductase from strain AKC-020 of the present invention and low ability to convert 2-deoxy-scyllo-inosose into (−)-vibo-quercitol.

FIG. 11 shows the amino acid sequence and nucleotide sequence of the coding region of an inositol dehydrogenase gene (GenBank Accession No. CAB15358) that has been clarified to have low sequence identity with the amino acid sequence of DOI reductase from strain AKC-020 of the present invention and low ability to convert 2-deoxy-scyllo-inosose into (−)-vibo-quercitol.

Figure 2:
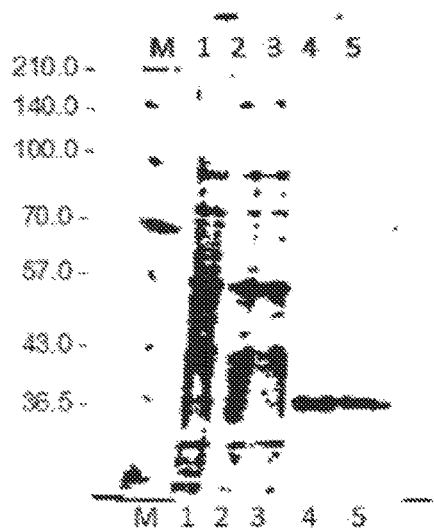
FIG. 2 is a photograph showing the results of SDS-PAGE of samples from each purification step of the 2-deoxy-scyllo-inosose reductase (sometimes abbreviated hereinafter as "DOI reductase" or "DOIR") of the present invention. In order from the left lane: Lane M: Prestained XL-Ladder (Broad); Lane 1: crude enzyme solution; Lane 2: ammonium sulfate fraction; Lane 3: Butyl-Toyopearl fraction; Lane 4: Resource Q fraction; and Lane 5: gel filtration fraction (acetone concentrated).

BEST MODE FOR CARRYING OUT THE INVENTION 1. 2-Deoxy-scyllo-inosose Reductase

The 2-deoxy-scyllo-inosose reductase of the present invention was isolated from microorganisms having the ability to utilize (−)-vibo-quercitol. Therefore, in addition to those described specifically in this specification, the 2-deoxy-scyllo-inositol reductase of the present invention can be obtained from other microorganisms having the ability to utilize (−)-vibo-quercitol. As a method of selecting such microorganisms, for example, microorganisms that exhibit good growth when cultured using one or more among (+)-proto-quercitol, (−)-proto-quercitol, (+)-vibo-quercitol, (−)-vibo-quercitol, (+)-epi-quercitol, (−)-epi-quercitol, (+)-gala-quercitol, (−)-gala-quercitol, (+)-talo-quercitol, (−)-talo-quercitol, (+)-allo-quercitol, (−)-allo-quercitol, scyllo-quercitol, neo-quercitol, cis-quercitol, and muco-quercitol as the sole carbon source may be isolated. Although (−)-vibo-quercitol, which is the direct target substance, is more desirable as a preferred carbon source, it is also possible to use a mixture containing (−)-vibo-quercitol and other quercitol isomers. For example, a mixture of (+)-proto-quercitol, (+)-epi-quercitol, and (−)-vibo-quercitol obtained by implementing a method described in Japanese Kokai Patent No. 2000-4890 and a mixture of (−)-vibo-quercitol and scyllo-quercitol obtained by hydrogenating 2-deoxy-scyllo-inosose (DOI) using a chemical catalyst may be utilized.

As a more specific example, an agar plate is inoculated with a dilute solution of a soil sample and approximately 0.6% (W/V) of a mixture of (−)-vibo-quercitol and scyllo-quercitol. An inorganic nitrogen source (for example, approximately 0.6% (W/V) ammonium sulfate) and inorganic salts necessary for the growth of common microorganisms (for example, $MgSO_4$, $KH_2PO_4$, NaCl, etc.) may preferably be added to this medium. The agar plate is then cultured for from about one day to one week at a temperature of about 20-30° C., and the colonies that appear may be isolated.

It is advantageous to select strains presenting higher 2-deoxy-scyllo-inosose reductase activity from among the microorganisms isolated in this way. To do this, cells of the isolated strains are sonicated, and a cell extract is obtained. This extract is mixed with a buffer containing 2-deoxy-scyllo-inosose (DOI), and an enzymatic reaction is initiated by adding a coenzyme: NADH thereto. The rate at which the NADH in the reaction solution is converted into $NADH^+$, that is, the rate at which 2-deoxy-scyllo-inosose is reduced, is measured as the change in absorbance of the reaction solution at predetermined times, and strains presenting higher 2-deoxy-scyllo-inosose reductase activity can be selected.

The enzyme of the present invention should also produce (−)-vibo-quercitol at a high diastereomer excess. This is because one diastereomer is isolated from the product, and inefficient steps can be omitted. It is therefore preferable to characterize the diastereomer productivity of the strains selected. To do this, for example, the cell extract is mixed with DOI and NADH. An enzymatic reaction can also be made to advance adequately by causing formate dehydrogenase and sodium formate to be jointly present as a coenzyme regeneration system while conducting the reaction. After the reaction, the reaction solution is analyzed, for example, by HPLC using Shodex KS-801 (trade name, manufactured by Showa Denko KK), and strains that produce (−)-vibo-quercitol at a high diastereomer excess can be identified by calculation.

[Chemical formula 3]

$$\text{Diastereomer excess (\% d.e.)} = \frac{[(-)\text{-vibo-quercitol}] - [\text{scyllo-quercitol}]}{[(-)\text{-vibo-quercitol}] + [\text{scyllo-quercitol}]} \times 100$$

Strains capable of converting 2-deoxy-scyllo-inosose into (−)-vibo-quercitol at a diastereomer excess of 80% or higher are preferred. Strains capable of converting 2-deoxy-scyllo-inosose into (−)-vibo-quercitol at a diastereomer excess of 85% or higher are more preferred, and strains capable of converting 2-deoxy-scyllo-inosose into (−)-vibo-quercitol at a diastereomer excess of 95% or higher are most preferred.

As a result of isolating, selecting, and characterizing strains by the method described above, the inventors discovered that six strains of *Pseudomonas* sp., one strain of *Burkholderia sediminicola*, two strains of *Burkholderia terrae*, and one strain of *Burkholderia* sp. have the ability to produce (−)-vibo-quercitol from DOI at a diastereomer excess of 80% or higher.

Therefore, it can be advantageous to screen microorganisms of the present invention having the ability to utilize (−)-vibo-quercitol from among microorganisms of the genus *Pseudomonas* or the genus *Burkholderia*. Examples of especially preferred microorganisms are those isolated by the inventors and named *Burkholderia terrae* AKC-020 and *Pseudomonas* sp. AKC-019.

*Burkholderia terrae* AKC-020 was accessioned with the National Patent Microorganisms Depositary (NPMD) of the National Institute of Technology and Evaluation (Room 122, 2-5-8 Kazusa-Kamatari, Kisarazu, Chiba Prefecture) as NITE P-01745 on Nov. 1, 2013. *Pseudomonas* sp. AKC-019 was accessioned with the National Patent Microorganisms Depositary (NPMD) of the National Institute of Technology and Evaluation (Room 122, 2-5-8 Kazusa-Kamatari, Kisarazu, Chiba Prefecture) as NITE P-01740 on Oct. 24, 2013.

The inventors also succeeded in purifying the 2-deoxy-scyllo-inosose reductase of the present invention from *Burkholderia terrae* AKC-020. Simply put, cultured cells of AKC-020 were sonicated, and a 30% saturated ammonium sulfate solution was produced by adding ammonium sulfate and KPB to the supernatant. The supernatant of this 30% saturated ammonium sulfate solution was subjected to hydrophobic chromatography, and the active fraction was eluted by ammonium sulfate concentration gradient. Next, the active fraction was dialyzed by MOPS buffer, then subjected to anion-exchange chromatography, and the active fraction was eluted by NaCl concentration gradient. Finally, it was purified by gel-filtration chromatography. The active fraction eluted at a retention time corresponding to a molecular mass of about 130 KDa in gel-filtration chromatography, but a single band was subsequently found at about 36 KDa when the purity was further confirmed by SDS-PAGE. Therefore, the 2-deoxy-scyllo-inosose reductase of the present invention produced by strain AKC-020 is presumed to form a homotetramer in solution.

The inventors also studied the properties of the 2-deoxy-scyllo-inosose reductase of the present invention produced by strain AKC-020. This enzyme presented maximum activity at pH 7.0-9.0. This enzyme also presented higher substrate specificity for (−)-vibo-quercitol than myo-inositol in an evaluation of oxidation activity, that is, in an evaluation of the reverse reaction that produces (−)-vibo-quercitol by reduction of 2-deoxy-scyllo-inosose.

Therefore, the 2-deoxy-scyllo-inosose reductase of the present invention can be defined as being derived from a microorganism having the ability to utilize (−)-vibo-quercitol and having the following properties:

(a) having catalytic activity to convert 2-deoxy-scyllo-inosose into (−)-vibo-quercitol;

(b) presenting maximum activity at pH 7.0-9.0; and (c) the molecular mass of a polypeptide moiety of the enzyme measured by SDS-polyacrylamide electrophoresis is 36 kDa.

In addition to the above, the 2-deoxy-scyllo-inosose reductase of the present invention can also be defined as having the following properties:

(d) converts 2-deoxy-scyllo-inosose into (−)-vibo-quercitol at a diastereomer excess of 80% or greater; and (e) presents higher substrate specificity for (−)-vibo-quercitol than myo-inositol in evaluation of oxidation activity.

2. Protein Having 2-deoxy-scyllo-inosose Reductase Activity

The inventors produced approximately 20 degenerate primers, taking into consideration the N-terminal sequence and internal sequence of the 2-deoxy-scyllo-inosose reductase produced by strain AKC-020 and the coding sequence of a known inositol dehydrogenase (sometimes abbreviated hereinafter as "IDH") assumed to be related thereto, and succeeded in acquiring the gene of 2-deoxy-scyllo-inosose reductase produced by strain AKC-020. The amino acid sequence of the 2-deoxy-scyllo-inosose reductase produced by strain AKC-020 was identified as the following from the coding region of the same gene:

[Chemical formula 4]
(SEQ ID NO: 2)
MIRIAVLGAGRIGRIHAGNVAASPNAQLVVVADPVESAAKSLATRLGCEA

STDPAGVLERKDIDAVVIGTPTDTHITFMLEAVRRGKAVLCEKPIDLDME

KSLAAANEVERQRGRVMLAFNRRFDPTSQAFRNAIDAGDVGEVRQVIISS

RDPGMPPRDYVEHSGGIFRDMVIHDLDMARWLLGEEPVEVMAMASRLIDE

SLEKLTDFDTVMVQLRTASGKQCHINCCREAVYGYDQRMEVSGSKGMLLQ

ENLRPSTIRRWSKEATDVREPLLNFFLERYEAAYKAELEAFVDALNTNSP

LPTSVQDGLKALRLADAALESALSGKAVKV

Therefore, it is evident that a protein having the above amino acid sequence presents the 2-deoxy-scyllo-inosose reductase activity of the present invention. Those skilled in the art, however, will appreciate that equivalent substances can also be used for the purposes of the present invention. To this end, the inventors also searched known amino acid sequences showing homology with the above SEQ ID NO: 2. The inventors then caused proteins having the retrieved sequence to be expressed recombinantly in Escherichia coli, and measured the enzymatic activity of proteins having these amino acid sequences. As a result, several inositol dehydrogenases were judged to present the 2-deoxy-scyllo-inosose reductase activity of the present invention.

More specifically, proteins having the following three sequences (see FIG. 8) presenting amino acid sequence identity of 58% or higher with SEQ ID NO: 2 presented catalytic activity to convert 2-deoxy-scyllo-inosose into (−)-vibo-quercitol equivalent to that of the 2-deoxy-scyllo-inosose produced by strain AKC-020.

[Chemical formula 5]
GenBank Accession No. EKS70356.1
(SEQ ID NO: 4)
MTRIAVLGAGRIGKIHAANVASNSDAKLVVVADPFEGAANSLAEKLGCEA

STDCLSVIERDDVDAVVIGTPTDTHIQFMLHAVSKGKAVLCEKPIDLDMK

KSLAAAKEVERHDGRVMLAFNRRFDPTSQAFRKAIDDGEVGDVRQVVITS

RDPGMPPREYVTHSGGIFRDMVIHDLDLARWFLGEEPIEVMATGSRLVEP

SLAEVPDFDTVMLQLRTESGKQCHINCCREAVYGYDQRLEVFGSRGMLLQ

ENLRPSTIRRWSASATDAREPLLNFFLERYEAAYKTELTAFVEALRTNTT

FPTSVADGLKALRLADCALESAMSCRSVKV;

GenBank Accession No. ADU72508.1
(SEQ ID NO: 6)
MKIAVLGAGRIGNVHAMNVASNPNVELVAIADPFIDNAIKLTEKYGGKAV

KEPMELIESNVDAVIIATPTDTHVDLMLSAARNGKAVLCEKPVDLNLERA

EVACAELKQCDVPVMIAFNRRFDPSAAEMHSAIAKGEVGELHQIMISSRD

PGFASMDYLRHSGGIFRDMTIHDFDMARWLLGEEPVQVFASASRMLEPAL

EPLNDFDTVMVQMITKSGKQCHINCSRQAVYGHDQRIEAYGSAGMLLNDN

LRPSTLRRFNKSATDARVPLVHFFLERYADAYRMELEAFISAVKHAKPVP

VTPYDGYMALKLADCAQQSAETGLPVQL;
and

GenBank Accession No. EIK69154.1
(SEQ ID NO: 8)
MLRIAVLGAGRIAKIHAANVAAHPNATLVLVADPWREGVDALSTQLGCEA

AYDCAAVLNRKDIDAVVIGTPTDTHIDLLLAAVAQGKAVLCEKPIDLDIA

KARSAAQTVERQGGKVMLGFNRRFDPDMLRLRQALDAGQIGAVRQVIITS

RDPGLAPREYLEHSGGILRDMTIHDFDTARHLLGEEPVQVSAFASRLVDP

SLEQIDDYDSVMVLLRTASGKQCHINCCRQAVYGYDQRVEVSGASGVLLT

DNHRPSTLRHW3SAEHTEALEPLQHFFLERYADAYRNELMQFVDALNEGR

ELPTGMRDGLYALHLADCALESVKTGRSVAVCYDR

Nonetheless, no reports have yet been made of any of the above three inositol dehydrogenases having catalytic activity to convert 2-deoxy-scyllo-inosose into (−)-vibo-quercitol. Furthermore, inositol dehydrogenases presenting lower homology (50% or less) with SEQ ID NO: 2 were judged to have little or no catalytic activity to convert 2-deoxy-scyllo-inosose into (−)-vibo-quercitol.

Therefore, a protein having the 2-deoxy-scyllo-inosose reductase activity of the present invention can comprise an amino acid sequence having identity of 58% or greater with the amino acid sequence represented by SEQ ID NO: 2. A protein comprising an amino acid sequence having identity of 68% or greater with the amino acid sequence represented by SEQ ID NO: 2 is preferred; a protein comprising an amino acid sequence having identity of 79% or greater is more preferred; a protein comprising an amino acid sequence having identity of 85% or greater is even more preferred; a protein comprising an amino acid sequence having identity of 90% or greater is even more preferred; and a protein comprising an amino acid sequence having identity of 95% or greater is especially preferred.

A protein having the 2-deoxy-scyllo-inosose reductase activity of the present invention can also comprise an amino acid sequence having identity of 56% or greater with the amino acid sequence represented by SEQ ID NO: 4. A protein comprising an amino acid sequence having identity of 64% or greater with the amino acid sequence represented by SEQ ID NO: 4 is preferred; a protein comprising an amino acid sequence having identity of 79% or greater is more preferred; a protein comprising an amino acid sequence having identity of 85% or greater is even more preferred; a protein comprising an amino acid sequence having identity of 90% or greater is even more preferred; and a protein comprising an amino acid sequence having identity of 95% or greater is especially preferred.

A protein having the 2-deoxy-scyllo-inosose reductase activity of the present invention can also comprise an amino acid sequence having identity of 54% or greater with the amino acid sequence represented by SEQ ID NO: 6. A protein comprising an amino acid sequence having identity of 65% or greater with the amino acid sequence represented by SEQ ID NO: 6 is preferred; a protein comprising an amino acid sequence having identity of 80% or greater is more preferred; a protein comprising an amino acid sequence having identity of 85% or greater is even more preferred; a protein comprising an amino acid sequence having identity of 90% or greater is even more preferred; and a protein comprising an amino acid sequence having identity of 95% or greater is especially preferred.

A protein having the 2-deoxy-scyllo-inosose reductase activity of the present invention can also comprise an amino acid sequence having identity of 54% or greater with the amino acid sequence represented by SEQ ID NO: 8. A protein comprising an amino acid sequence having identity of 64% or greater with the amino acid sequence represented by SEQ ID NO: 8 is preferred; a protein comprising an amino acid sequence having identity of 68% or greater is preferred; a protein comprising an amino acid sequence having identity of 80% or greater is more preferred; a protein comprising an amino acid sequence having identity of 85% or greater is even more preferred; a protein comprising an amino acid sequence having identity of 90% or greater is even more preferred; and a protein comprising an amino acid sequence having identity of 95% or greater is especially preferred.

In the above, SEQ ID NO: 4 and SEQ ID NO: 6 present 56% identity; SEQ ID NO: 4 and SEQ ID NO: 8 present 64% identity; and SEQ ID NO: 6 and SEQ ID NO: 8 present 54% identity.

Furthermore, in this specification, the identity of amino acid sequences is shown by the percentage of matching amino acids shared between two sequences when two sequences are aligned in an optimal manner (number of amino acids of matching location/number of amino acids aligned×100). Calculation was performed by the BLAST algorithm which can be accessed at the internet site <http://www.ncbi.n/m.nih.gov/egi-gin/BLAST≥.

In addition, the following eight partial sequences were highly conserved between the above three inositol dehydrogenases presenting amino acid sequence identity of 58% or higher with the 2-deoxy-scyllo-inosose reductase produced by strain AKC-020 of the present invention (see FIG. 8). Therefore, a protein having the 2-deoxy-scyllo-inosose reductase activity of the present invention preferably has one or more of these eight partial sequences.

[Chemical formula 6]

```
                                            (SEQ ID NO: 10)
Partial sequence 1: RIAVLGAGRIG (SEQ ID NO: 12)
Partial sequence 2: DAVVIGTPTDTHI (SEQ ID NO: 14)
Partial sequence 3: GKAVLCEKPIDLD (SEQ ID NO: 16)
Partial sequence 4: VMLAFNRRFDP (SEQ ID NO: 18)
Partial sequence 5: HSGGIFRDM (SEQ ID NO: 20)
Partial sequence 6: ARWLLGEEPV (SEQ ID NO: 22)
Partial sequence 7: DFDTVMVQLRTASGKQCHINCCR (SEQ ID NO: 24)
Partial sequence 8: AVYGYDQR
```

Moreover, it is known that two molecules present the same bioactivity if they have a substantially similar structure even if the amino acid sequences of the two protein molecules are not exactly the same. For example, even substituting valine for leucine, arginine for lysine, or asparagine for glutamine may sometimes not change the function of a protein. Therefore, proteins comprising an amino acid sequence in which one or several amino acids have been deleted, substituted, and/or added in the amino acid sequence shown by SEQ ID NO: 2 also having 2-deoxy-scyllo-inosose reductase activity can also be used suitably for the purposes of the present invention.

3. Gene

As will be described below, it is advantageous to use a gene encoding this enzyme or protein when producing the 2-deoxy-scyllo-inosose reductase and protein having this enzymatic activity of the present invention.

For example, the enzyme can be efficiently produced by transforming an appropriate host cell using the 2-deoxy-scyllo-inosose reductase gene that the inventors isolated from strain AKC-020 and determined the sequence thereof. The nucleotide sequence of the coding region of this gene appears below.

[Chemical formula 7]

```
                                            (SEQ ID NO: 1)
ATGATTCGAATCGCCGTACTCGGTGCCGGCCGCATTGGTCGCATTCACGC

TGGCAACGTCGCCGCTAGTCCGAATGCACAACTGGTCGTGGTGGCAGACC

CGGTTGAAAGTGCAGCAAAATCGTTGGCTACCCGTCTGGGCTGCGAAGCC

TCGACGGACCCCGCGGGCGTGCTCGAACGCAAAGATATCGATGCGGTCGT

CATCGGCACGCCGACGGACACGCACATCACGTTCATGCTTGAAGCCGTCA
```

-continued

GGCGCGGCAAGGCTGTTCTGTGTGAGAAGCCCATCGACCTCGACATGGAA

AAGTCGCTTGCCGCGGCAAACGAGGTCGAGCGCCAGCGTGGCCGCGTCAT

GCTCGCTTTCAATCGACGTTTCGACCCGACGTCGCAAGCATTCCGCAACG

CGATTGACGCGGGCGATGTTGGCGAAGTGCGCCAGGTCATCATTTCGAGC

CGCGACCCGGGCATGCCTCCGCGTGACTATGTCGAGCACTCGGGCGGCAT

CTTCCGCGACATGGTGATCCACGACCTGGATATGGCGCGCTGGTTGCTCG

GCGAAGAGCCCGTCGAGGTAATGGCGATGGCCAGCCGCCTCATCGACGAG

TCGCTCGAAAAACTGACCGACTTCGATACGGTGATGGTGCAGTTACGGAC

CGCGTCGGGCAAGCAATGCCATATCAACTGCTGTCGCGAAGCCGTGTACG

GCTACGACCAGCGCATGGAAGTCTCGGGTTCGAAGGGAATGCTCCTTCAA

GAGAATCTTCGACCGTCGACGATCCGGCGCTGGTCCAAGGAAGCGACCGA

CGTTCGCGAGCCGCTGCTCAACTTCTTCCTGGAGCGCTACGAGGCTGCGT

ACAAGGCGGAGCTCGAAGCCTTCGTCGATGCGCTGAACACGAACTCGCCG

CTGCCGACGTCCGTGCAGGACGGTCTGAAGGCGTTGCGCCTCGCGGATGC

GGCACTCGAGTCCGCGCTGTCGGGCAAAGCCGTCAAGGTGTAA

The 2-deoxy-scyllo-inosose reductase gene that can be utilized for the purposes of the present invention may have any of the mutations that can occur in nature or artificially introduced mutations and modifications. For example, excess codons (redundancy) are known to be present in various codons encoding specific amino acids. Alternative codons that will ultimately be translated into the same amino acid may therefore be utilized in the present invention as well. In other words, since the gene code degenerates, multiple codons can be used to code a certain specific amino acid. An amino acid sequence therefore can be encoded by similar DNA oligonucleotides of any one set. Only one member of this set is the same as the gene sequence of the native enzyme, but DNA capable of hybridizing with the native sequence under stringent despite mismatched DNA oligonucleotides and encoding the native sequence can be identified and isolated, and such genes can also be utilized in the present invention. Furthermore, in this specification, the term stringent conditions means maintaining at a constant temperature of 65° C. for 8-16 hours together with a probe in a solution containing 6×SSC (composition of 1×SSC: 0.15 M sodium chloride, 0.015 M sodium citrate, pH 7.0), 0.5% SDS, 5×Denhardt's solution, and 100 mg/mL of herring sperm DNA, hybridizing, and then washing, for example, by 2×SSC and 0.1% SDS at 68° C., as descried in Molecular Cloning—A Laboratory Manual, $2^{nd}$ edition (Sambrook et al., 1989).

As mentioned above, three inositol dehydrogenases (IDH) presenting amino acid sequence identity of 58% or greater with the 2-deoxy-scyllo-inosose reductase discovered by the inventors existed. The inventors were also the first to clarify that these three IDH also present previously unreported 2-deoxy-scyllo-inosose reductase activity. The inventors also discovered highly conserved amino acid sequences in the eight regions mentioned above by aligning the amino acid sequence of the 2-deoxy-scyllo-inosose reductase discovered by the inventors and the amino acid sequences of these three IDH. Those skilled in the art will therefore appreciate that genes encoding a protein presenting the 2-deoxy-scyllo-inosose reductase activity of the present invention can be isolated easily by using as a probe DNA complementary to the full length or part of the nucleotides encoding the amino acid sequence of any of these eight regions. In other words, typically DNA comprising the full length or part, for example, 15, 18, or 20 consecutive bases, of a sequence complementary to any of the following eight nucleotide sequences is preferred for use as a probe to search for genes of the present invention.

[Chemical formula 8]
Partial sequence 1:
(SEQ ID NO: 9)
cgaatcgccgtactcggtgccggccgcattggt Partial sequence 2:
(SEQ ID NO: 11)
gatgcggtcgtcatcggcacgccgacggacacgcacatc Partial sequence 3:
(SEQ ID NO: 13)
ggcaaggctgttctgtgtgagaagcccatcgacctcgac Partial sequence 4:
(SEQ ID NO: 15)
gtcatgctcgctttcaatcgacgtttcgacccg Partial sequence 5:
(SEQ ID NO: 17)
cactcgggcggcatcttccgcgacatg Partial sequence 6:
(SEQ ID NO: 19)
gcgcgctggttgctcggcgaagagcccgtc Partial sequence 7:
(SEQ ID NO: 21)
gacttcgatacggtgatggtgcagttacggaccgcgtcgggcaagcaatg
ccatatcaactgctgtcgc Partial sequence 8:
(SEQ ID NO: 23)
gccgtgtacggctacgaccagcgc In addition, since virtually all organisms are known to use subsets of specific codons (optimal codons) preferentially (Gene, Vol. 105, pp. 61-72, 1991, and the like), "codon optimization" in accordance with the host microorganism can also be useful in the present invention. Therefore, the gene of the present invention may have a nucleotide sequence encoding a protein having 2-deoxy-scyllo-inosose reductase activity that is a nucleotide sequence in which one or several nucleotides have been deleted, substituted, and/or added in the nucleotide sequence represented by SEQ ID NO: 1.

4. Method for Producing 2-deoxy-scyllo-inosose Reductase

The 2-deoxy-scyllo-inosose reductase and protein having 2-deoxy-scyllo-inosose reductase activity of the present invention can be produced easily by utilizing recombinant DNA technology. Typically, genes encoding these enzyme proteins are introduced into a host cell as an expression cassette. The protein can then be expressed stably inside the transformed host cell (also referred to hereinafter as "transformant").

In this specification, an expression cassette means a nucleotide containing a base sequence for regulating transcription and translation bonded functionally to a nucleic acid to be expressed or a gene to be expressed. Typically, an expression vector of the present invention contains a promoter sequence 5' upstream from the coding sequence, a terminator sequence 3' downstream, and sometimes also a normal regulatory element in a functionally linked state. In such cases, the nucleic acid to be expressed or the gene to be expressed is "introduced expressibly" into the host cell.

A promoter, whether a structural promoter or a regulator promoter, is defined as a DNA sequence that bonds RNA polymerase to DNA and initiates RNA synthesis. A strong promoter is a promoter that initiates mRNA synthesis at high frequency and can also be used suitably in the present invention. The lac system, trp system, TAC or TRC system, main operator and promoter regions of phage lambda, control region for fd coat protein, promoters for glycolytic enzymes (for example, 3-phosphoglycerate kinase, glyceraldehyde-3-phosphate dehydrogenase), glutamate decarboxylase A, and serine hydroxymethyl transferase, and the like can be utilized in accordance with the properties and the like of the host cells. In addition to promoter and terminator sequences, examples of other regulatory elements include selection markers, amplification signals, replication points, and the like. Suitable regulatory sequences are described, for example in "Gene Expression Technology: Methods in Enzymology 185," Academic Press (1990).

The expression cassette explained above is incorporated into a vector comprising a plasmid, phage, transposon, IS element, phasmid, cosmid, or linear or cyclic DNA, or the like (that is, a recombinant vector) and inserted into a host cell. Plasmids and phages are preferred. These vectors may be autonomously replicated or replicated by chromosomes in the host cells. Suitable plasmids include pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, λgt11, or pBdCI from $E.$ $coli$; pUB110, pC194, or pBD214 from $Bacillus$; pSA77 or pAJ667 from the genus $Corynebacterium$, and the like. Plasmids and the like that can be used other than these are described in "Cloning Vectors," Elsevier, 1985. The expression cassette can be introduced into the vector by common methods, including cutting by suitable restriction enzymes, cloning, and ligation.

Methods such as coprecipitation, protoplast fusion, electroporation, retrovirus transfection, and other such common cloning methods and transfection methods, for example, can be used as methods that can be applied to introduce the vector into the host cells and transform them after having constructed a recombinant vector having an expression cassette of the present invention as described above. These examples are described in "Current Protocols in Molecular Biology," F. Ausubel et al., Publ. Wiley Interscience, New York, 1997 or Sambrook et al., "Molecular Cloning—A Laboratory Manual," $2^{nd}$ edition, Cold Spring Harbor Laboratory, Cold Spring Harbor Laboratory Press, Cold Spring Harbor, N.Y., 1989.

Examples of the host cells of the present invention include prokaryotic bacteria, yeasts of the genus $Saccharomyces$, genus $Pichia$, and the like, insect cells such as SF9 and the like, and animal cells such as CHO, COS7, and the like. Preferred hosts are bacteria of the genera $Escherichia$, $Pseudomonas$, $Bacillus$, $Geobacillus$, $Methanomonas$, $Methylobacillus$, $Methylophilius$, $Protaminobacter$, $Methylococcus$, $Corynebacterium$, $Brevibacterium$, $Salmonella$, and $Listeria$. $E.$ $coli$, $Bacillus$ bacteria, $Corynebacterium$ bacteria, and $Salmonella$ bacteria, the use of which has been established in industrial fermentation production, is more preferred. $E.$ $coli$ is an example of an especially preferred host microorganism of the present invention because it has the ability to grow rapidly and fermentation control is easy.

The transformed microorganisms obtained in this way are cultured under conditions suited to the growth of the transformed microorganisms to produce the enzyme protein of the present invention. Suitable medium compositions, culture conditions, and culture time for transformants derived from various types of host microbial cells are known to those skilled in the art. The medium may be a natural, semisynthetic, or synthetic medium containing one or more carbon sources, nitrogen sources, inorganic salts, vitamins, and sometimes trace elements, vitamins, or other such trace components. However, it goes without saying that the medium used must properly satisfy the nutrient requirements of the transformed microorganisms to be cultured. When the transformed microorganisms express useful additional traits, for example, resistance markers to antibiotics, the medium may contain the corresponding antibiotic. This reduces the risk of contamination by unwanted bacteria during fermentation. Furthermore, with respect to additional traits, the enzyme and protein of the present invention can also be produced by transformants as fusion proteins with another protein and a tag, for example, glutathione S transferase, protein A, a hexahistidine tag, FLAG tag, and the like to facilitate subsequent purification. The fusion protein produced can be cut using a suitable protease, for example, thrombin or the like.

Culture may be by batch or continuous. In either case, the medium may be replenished with additional carbon source and the like at appropriate times during culture. Culture should also be continued while maintaining a suitable temperature, oxygen concentration, pH, and the like. A suitable temperature for the culture of transformants derived from common microbial host cells is usually in a range of 15-45° C., preferably 25-37° C. When the host microorganisms are aerobic, shaking (flask culture, etc.) or stirring/ventilation (jar fermenter culture, etc.) is necessary to assure an appropriate oxygen concentration during fermentation. These culture conditions can be established easily by those skilled in the art.

Next, a protein having the 2-deoxy-scyllo-inosose reductase activity of the present invention is purified from the culture obtained by culturing for a suitable length of time under conditions suited to the production of the enzyme protein of the present invention. In short, the protein may be purified from the cultured cells when the protein is accumulated inside the cells of the transformed microorganism; the protein may be purified from the culture supernatant when the protein is released outside the cells of the transformed microorganisms. Several purification methods can be utilized. For example, the enzyme protein of the present invention can be purified from a dissolved cell solution or extract or the culture supernatant through the use of salt fractionation, ion-exchange chromatography, size-exclusion chromatography, hydroxyapatite-adsorption chromatography, and hydrophobic interaction chromatography, individually or in various combinations.

As a concrete example relating to the purification of the enzyme protein of the present invention, the cultured cells are sonicated, and ammonium sulfate is added to the supernatant to produce a 30% saturated ammonium sulfate solution. The supernatant of this 30% saturated ammonium sulfate solution is subjected to hydrophobic chromatography, and the active fraction is eluted by an ammonium sulfate concentration gradient. Next, after dialyzing the active fraction, it is subjected to anion-exchange chromatography, and the active fraction is eluted by NaCl concentration gradient. Finally, it can be purified by gel filtration chromatography.

5. Method for Producing (−)-vibo-quercitol (−)-Vibo-quercitol can be produced very easily and efficiently by utilizing a protein having the 2-deoxy-scylloinosose reductase activity of the present invention. In other words, of course the 2-deoxy-scyllo-inosose reductase having the amino acid sequence of SEQ ID NO: 2 discovered by the inventors can be utilized, as can proteins shown by SEQ ID NOS: 4, 6, and 8 previously known to present only inositol dehydrogenase activity but clarified for the first time by the inventors to have 2-deoxy-scyllo-inosose reductase activity be utilized in the method for producing (−)-vibo-quercitol. Furthermore, the respective coding regions of these genes are as follows.

[Chemical formula 9]

(SEQ ID NO: 3)
atgactcgcattgcagttctcggagcaggccgtatcggaaagattcacgc agcgaacgttgcatcgaactcggacgcgaagctcgtcgtggttgcagacc cgttcgaaggcgcagccaactctttggcggagaagctcggttgcgaagcg tccaccgactgtctctctgttatcgagagggacgacgtcgatgctgtcgt cattggcacgccgaccgatacccacatccagttcatgcttcatgcggttt caaaagggaaggcagttctctgcgagaaacccatcgacctggatatgaaa aagtcgctcgcggcagccaaggaggtcgaacggcacgatggacgcgtgat gctggcattcaatcgtcgattcgacccgacgtcgcaggccttccggaaag ccatcgatgatggggaagtcggtgatgtccgacaggttgtcattaccagt cgcgaccccggtatgccccgcgagagtatgtgacgcactccggcggcat cttccgcgacatggttattcacgaccttgacctcgcacgatggtttcttg gagaagagcccattgaagtgatggccactggtagccggctcgtggaacca agcctcgcggaagttccggacttcgatacggtcatgctgcaactgcgtac cgaaagcggaaagcaatgccacatcaattgctgtcgcgaggccgtctacg gttacgaccaacgcctcgaagtgttcggctcccgcggcatgctccttcag gaaaatctgcgaccctccacgattcgccgctggagcgcgagtgcaaccga tgcccgtgagccgctccttaacttttcctggagcgctatgaagcggcata taagacggagctcaccgcctttgtagaggcattgcgaacgaacactacgt tcccgacttctgttgcggacgggcttaaagcgttgcggcttgctgactgc gctcttgaatctgcgatgtcgtgtaggtcagttaaagtctaa;

(SEQ ID NO: 5)
atgaaaattgccgtacttggcgcaggccgcattggcaacgtccacgcaat gaatgttgcaagcaaccccaatgttgaactggtcgcgattgctgatcctt tcatcgacaacgctatcaaactgacggagaaatatggtggcaaggccgtg aaagagccgatggagttgattgagagcaatgcggtggatgccgtgatcat tgcgacacctaccgatacgcatgttgatctgatgttgagtgcagcccgca atggtaaagcggtactgtgtgaaaaaccggtagaccttaacctggaacgt gccgaagtcgcctgcgcagagcttaagcaatgcgatgttcccgtcatgat tgcctttaaccgccgctttgatcccagcgcagctgaaatgcacagcgcca ttgcgaaaggtgaagtgggcgaactgcatcaaatcatgatttccagccgt gacccgggctttgcctccatggactatctgcgtcactctggcggcatctt ccgggacatgacgattcatgattttgacatggcgcgctggttactcggtg aagagcctgtgcaggtatttgcctctgccagccgtatgctggagccggca ttagaaccgttgaatgatttcgataccgtgatggttcagatgatcactaa atcgggtaagcaatgccacatcaactgtagtcgtcaagccgtctatggac atgaccaacgcattgaagcttatggttctgcagggatgttactcaatgac aatcttcgcccatccactctgcgtcgtttcaataaatcggcaaccgatgc tcgcgttccattagtccacttcttcctcgaacgctatgcggatgcctacc ggatggaactggaagccttcatttccgcggttaagcatgcgaagcccgtt cctgttacccttatgatggatatatggcgctgaagctcgccgactgtgc gaacaatcggctgaaactggtttacctgtgcagctttaa;
and (SEQ ID NO: 7)
atgctacgtattgccgttctaggtgcggggcgcatcgccaagatccacgc cgccaacgtcgctgcccatcccaacgccacgctggtgctggtggccgacc cctggcgcgaaggcgtcgatgccctgagcacgcagttgggatgtgaagca gcatacgactgcgccgcgtgctgaaccgcaaggacatcgacgcagtggt gatcggcacgcccaccgacacccatatcgacctgttgctggccgccgtgg cccagggcaaggcggtactctgtgaaaagcccatcgacctggatatcgcc aaggcgcgcagcgcagcacaaaccgtggagcgtcagggcggcaaggtgat gcttggcttcaaccgccgtttcgacccggacatgctgcggctgcgccagg ccttggacgccggccagatcggcgcagtgcgccaggtgatcattaccagc cgcgaccccggcctggctccgcgcgagtatctggaacattccggtggcat cctgcgcgatatgactatccacgacttcgacactgcccggcacttgctgg gtgaagagccggtgcaagtcagcgccttcgccagccgcctggtagacccg agcctggaacagattgacgactacgacagcgtgatggtcctgctgcgcac cgcctcgggcaagcaatgccatatcaactgctgccgccaggcggtgtatg gctacgatcaacgtgtagaagtctccggcgccagcggcgtactgctcacc gataaccacaggcccagtaccttgcgacactggagtgctgaacacactga agcactggagccgttgcagcacttttttccttgagcgctatgcggatgcct atcgtaatgagttgatgcagtttgtcgatgcgctgaatgaggggcgtgag ttgcccaccggcatgcgtgatgggctgtatgccttgcacctggctgactg tgcgttggagtcggttaagacggggcgcagcgtggccgtttgttatgacc ggtag The enzymatic reaction of the present invention may be carried out in buffer having a pH within a range of about 5.0-10.0, which is the pH at which the 2-deoxy-scyllo-inosose reductase of the present invention presents the maximum activity. The above pH is preferably 5.5-9.5, most preferably 7.0-9.0. For example, KPB or Tris-HCl buffer adjusted to this pH range can be used. The amount of enzyme of the present invention used in the reaction can be selected as is appropriate depending on the substrate concentration, desired reaction time, and the like, but is usually 5-500 U/L.

The 2-deoxy-scyllo-inosose that is the substrate of this enzymatic reaction can be obtained easily by methods described, for example, in WO2010/109916, WO10/053052, WO06/109479, and the like. This substrate can be dissolved in the desired concentration in the above buffer. 10-500 mM can be given as an example, but the concentration is not limited to this range. On the other hand, it is essential to add NADH to the reaction system as a coenzyme to carry out the reductase reaction of the present invention. The amount of NADH added may be an excess over the amount of substrate, but about 1.2-2 times the amount of substrate is usually adequate. The concentration of (−)-vibo-quercitol in the reaction solution may be monitored over time, and the reaction time set at the time when the amount produced peaks, but it is easier to observe the absorbance (for example, at a wavelength of 340 nm) of the buffer which changes as the NADH is converted into NADH⁺, and to set the reaction time at the time when that change no longer occurs. An example of a suitable reaction time is from 20 minutes to 120 hours; 30 minutes to 60 hours is preferred, 30 minutes to 10 hours is more preferred, and 30 minutes to 3 hours is most preferred, from the viewpoint of the stability of the enzyme. The reaction temperature may be decided in light of the maximum activity of the protein having the 2-deoxy-scyllo-inosose reductase activity of the present invention and can typically be about 15-40° C., preferably 25-30° C.

The (−)-vibo-quercitol can be isolated very easily and at high purity from the above enzymatic reaction product. Specifically, since the protein having the 2-deoxy-scyllo-inosose reductase activity of the present invention converts 2-deoxy-scyllo-inosose into (−)-vibo-quercitol at an extremely high yield and diastereomer excess, the use of complicated processes such as chromatography can be avoided. For example, the (−)-vibo-quercitol can be isolated merely by concentrating the reaction solution properly after the reaction has ended and recrystallizing by adding a lower alcohol. As a concrete example, the enzymatic reaction solution is concentrated until the content of (−)-vibo-quercitol is about 20-50% (W/V), and a 0.5-2-fold quantity of ethanol is then added thereto.

Those skilled in the art to whom the above explanation has been given can implement the present invention adequately. Examples are given below for the purpose of further explanation. The present invention therefore is not limited to these examples. Furthermore, unless stated otherwise, "%" in this specification represents a mass/volume percentage (% (W/V)). In addition, nucleotide sequences are described in the direction from 5' to 3'.

EXAMPLES

1. Screening for (−)-vibo-quercitol-utilizing Organisms

Approximately 0.1 g of soil was added to 0.85% sterilized aqueous saline and stirred thoroughly. The mixture was then allowed to stand for three hours, and the sand, plant roots, and the like sedimented. A quantity of 0.1 mL of the supernatant was applied to quercitol agar medium (composition shown in Table 1). Culture was carried out for 1-2 days at 30° C., and the organisms that grew were isolated by LB agar medium (composition shown in Table 1). Strains that formed single colonies were inoculated onto slant medium (quercitol agar medium), cultured at 30° C., and then preserved at 4° C. One hundred nine strains of soil organisms were acquired by conducting this experiment 63 times.

TABLE 1

| Medium composition |
|---|
| Quercitol agar medium: |
| Equal amounts of solutions I and II below were added to make the quercitol agar medium. |
| Solution I: 0.6% (NH₄)₂SO₄, 0.04% MgSO₄, 0.6% KH₂PO₄, and 0.2% NaCl were adjusted to pH 7.0. Agar was added to make a final concentration of 3%, and the medium was sterilized by autoclave. |
| Solution II: 0.6% racemic quercitol aqueous solution (filter sterilized) containing basically equal amounts of (−)-vibo-quercitol and scyllo-quercitol |
| LB agar medium: |
| 1% Tryptone, 0.5% yeast extract, and 0.5% sodium chloride were dissolved in distilled water and adjusted to pH 7.0 by NaOH. Agar was added to make a final concentration of 1.5%, and the medium as sterilized by autoclave. |

2. Acquiring Microorganisms Having the Ability to Convert 2-deoxy-scyllo-inosose (DOI) into (−)-vibo-quercitol The 109 strains of soil organisms acquired above were each inoculated onto 2 mL of quercitol medium (composition the same as the above agar medium with the agar removed) and cultured for 1-2 days at 30° C. Since 45 strains among them were found to grow well, the culture broth was centrifuged (15000 rpm, 10 min, 4° C.), and the cells were collected. The collected cells were suspended in 2 mL of 20 mM potassium phosphate buffer (pH 7.0) and treated five times by a sonication device (Tomy Seiko, UD-200, output: 60 W, frequency: 20 kHz) for 30 seconds. The cells were disrupted, and the supernatant was recovered by centrifugation (15000 rpm, 10 min, 4° C.). The recovered solution was taken as a crude enzyme solution and was subjected to enzymatic reaction evaluation by the following procedure.

(1) Evaluation of Enzymatic Reaction

The composition of the reaction solution was as follows. Furthermore, the amount of crude enzyme solution used was 10 μL.

TABLE 2

| Reaction solution composition | |
|---|---|
| Final concentration | Reagent or test solution |
| 0.3 mM | NADH |
| 0.1% | DOI |
| 0.05M | KPB pH 7.0 |
| | Crude enzyme solution |
| Total | 1 mL |

In the enzymatic reaction, the amount of the coenzyme NADH converted into NAD⁺ was measured quantitatively by spectrophotometer. Specifically, the reaction solution composition other than DOI (990 μL) was taken by cuvette and prewarmed for approximately 5 minutes at 25° C. After adding DOI solution (10 μL) and mixing quickly, the rate of decrease in the absorbance (wavelength 340 mm) over two minutes was measured using a spectrophotometer (Shimadzu, UV-2550) regulated to 25° C. with water as the control, and the decrease in absorbance per minute was calculated. Next, each strain was evaluated by calculating the U per mL of crude enzymatic solution, defining the amount that decreases [sic; converts] 1 μmol of NADH in one minute as 1 unit (U), taking the molecular extinction coefficient of NADH at a wavelength of 340 nm to be 6.22 mM⁻¹ cm⁻¹. The inventors succeeded in acquiring 10 strains showing activity exceeding 0.2 U/mL (crude enzyme solution) based on these results.

(2) Evaluation of Diastereomer Excess

Next, crude enzyme solution was acquired from these ten strains in the same way as above, and the diastereomer excess in the reaction from DOI to (−)-vibo-quercitol was evaluated. Specifically, DOI conversion was carried out using a coenzyme regeneration system by formate dehydrogenase (FDH hereinafter, Roche Diagnostics Inc., product no. 244678). Table 3 shows the composition of the conversion reaction solution. The reaction solution was incubated for three hours while shaking at 30° C. After the reaction was completed, the solution was centrifuged (15,000 rpm, 15 min), and the (−)-vibo-quercitol and scyllo-quercitol were quantified by HPLC analysis (conditions shown in Table 4) of the supernatant.

TABLE 3

Reaction solution composition

| | Final concentration |
|---|---|
| Crude enzyme solution | 0.5 U |
| DOI | 10 mM |
| NADH | 1 mM |
| Sodium formate | 0.02M |
| FDH | 0.2 U |
| 0.2M KBP, pH 7.0 | Total amount of reaction solution 0.5 mL |

TABLE 4

Conditions for analyzing quercitol by HPLC

Differential refractive index (RI) detector: Shodex RI-71 (product name, manufactured by Showa Denko KK)
Flow rate: 1.5 mL/min
Column: Shodex KS-801(product name, manufactured by Showa Denko KK)
Guard column: Shodex KS-G (product name, manufactured by Showa Denko KK)
Column temperature: 70° C.
Mobile layer: degassed water The diastereomer excess was calculated by the following formula. All ten strains achieved a high diastereomer excess of 80% or greater.

[Chemical formula 9]

$$\text{Diastereomer excess (\% d.e.)} = \frac{[(-)\text{-vibo-quercitol}] - [\text{scyllo-quercitol}]}{[(-)\text{-vibo-quercitol}] + [\text{scyllo-quercitol}]} \times 100$$

3. Identification of Microorganisms

The genome was extracted to identify the microorganisms. After culturing by 4 mL of LB medium and collecting the cells, the cells were suspended in 0.72 mL of 0.05 M Tris-HCl (pH 8.0), and lysozyme was added. After incubating for 30 minutes at 37° C., 0.08 mL of 2 M NaCl and proteinase K and 0.08 mL of 10% SDS were added, and treatment was carried out for ten minutes at 37° C. An equal amount of Tris-saturated phenol/chloroform/isoamyl alcohol (ratio 50: 48: 2) solution was added, and centrifugation (15,000 rpm, 10 in, 4° C.) was conducted after stirring vigorously. The upper layer was transferred to a fresh tube, a two-fold volume of ethanol was added, and the supernatant was discarded by centrifugation (15,000 rpm, 10 min, 4° C.). The residue was rinsed twice by 70% ethanol and resuspended in 0.1 mL of 0.05 M Tris-HCl (pH 8.0). RNase was added, and treatment was conducted for one hour at 37° C., a quantity of 0.4 mL of 0.05 M Tris-HCl (pH 8.0) and 0.1 mL of 2 M NaCl were added, and phenol/chloroform extraction was repeated. After precipitation by ethanol, the product was rinsed twice by 70% ethanol. The genome obtained was suspended in 0.5 mL of 0.05 M Tris-HCl (pH 8.0). Using the genome obtained as a template, a partial sequence of a 16SrRNA gene was amplified by PCR, and the partial base sequence thereof was determined using an ABI PRISM (registered trademark) 310 Genetic Analyzer. Table 5 shows the amplification conditions of the 16SrRNA gene.

TABLE 5

Table 5: Amplification conditions of the 16SrRNA gene (1) PCR reaction solution composition and amount added (50 µL)
DNA polymerase: KOD FX (trade name) manufactured by TOYOBO (1 unit)

Primer (1) used: name 16SrDNA-f, sequence 5'-agagtttgatcctggctcag-3' (SEQ ID NO: 84) (50 pmol)

Primer (2) used: name 16SrDNA-r, sequence 5'-acggctaccttgttacgactt-3' (SEQ ID NO: 85) (50 pmol)

2x PCR buffer for KOD FX (25 µL)

2 mM dNTPs (0.4 mM each)

Genomic DNA (200 ng)

Distilled water

PCR cycle
(Denature: 98° C., 10 sec, Annealing: 55° C., 30 sec, Extension: 68° C., 90 sec) x 30 cycles (2) 16SrRNA gene sequencing conditions
PCR reaction solution (20 µL)

BigDye (registered trademark) Terminator v3.1 Sequencing manufactured by Life Technologies (2 µL)

BigDye (registered trademark) Terminator v1.1/v3.1 Sequencing Buffer 5x (3 µL)

Primer (1) used: name 16SrDNA-f, sequence 5'-agagtttgatcctggctcag-3' (SEQ ID NO: 86) (3.2 pmol)

Template DNA (100 ng)

Distilled water

PCR cycle
(Denature: 96° C., 10 sec, Annealing: 50° C., 5 sec, Extension: 60° C., 240 sec) x 24 cycles As a result of identification by the 16SrRNA gene using a BLAST search (using the 16S ribosomal RNA sequences as the database searched), of the ten strains of microorganisms previously acquired, six strains were attributed to *Pseudomonas* sp., one to *Burkholderia sediminicola*, two to *Burkholderia terrae*, and the last one to *Burkholderia* sp. The 16SrRNA genes of these strains are shown as SEQ ID NOS: 74-83 in FIG. 1. Among these strains, one strain belonging to *Burkholderia terrae* was named strain AKC-020, and one strain belonging to *Pseudomonas* sp. was named strain AKC-019.

4. Purification of DOI Reductase

*Burkholderia terrae* strain AKC-020 was shake cultured overnight using LB liquid medium, and the product was taken as a preculture broth. The main culture was carried out by adding 1 mL of preculture broth to 100 mL of yeast extract/tryptone/DOI medium (composition shown in Table 6). One hundred mL of medium was placed in a 500 mL Sakaguchi flask, and the main culture was carried out at a speed of 120 rpm, 30° C., for 24 hours.

TABLE 6

Composition of medium (yeast extract/tryptone/DOI medium)

0.2 g of yeast extract
0.4 g of tryptone
1 mL of 50% DOI aqueous solution*

*Dissolved in 80 mL of distilled water, adjusted to pH 7.0 by NaOH, then diluted to 99 mL. Autoclaved after adding one drop of defoaming agent, and 1 mL of filter sterilized 50% DOI aqueous solution added after cooling to room temperature.

The cells were collected from 100 mL of culture broth, resuspended in 25 mL of 0.02 M potassium phosphate buffer (KPB) (pH 7.0), and sonicated (Tomy Seiko, sonication device UD-200, output: 200 W, frequency: 20 kHz) for five minutes at intervals of 30 seconds on ice. Thirty-five mL of 30% saturated ammonium sulfate concentrated solution was produced by adding 5.4 g of ammonium sulfate and KPB to the supernatant obtained by centrifuging (15,000 rpm, 10 min, 4° C.) the sonicated solution. The supernatant obtained by centrifuging (15,000 rpm, 10 min, 4° C.) after cooling for 40 minutes on ice was taken as the ammonium sulfate precipitate fraction.

Hydrophobic chromatography was conducted next. The column used was a Toyopearl Butyl-650M (Tosoh Corp.). The size of the open column used was 2.5 cm (diameter)×6.5 cm, the column volume was approximately 30 mL, the flow rate was approximately 0.8 mL/min, the fraction size was approximately 5 mL/tube, and elution was performed by creating an ammonium sulfate concentration gradient from 30% to 0% at a flow rate of 400 mL.

Anion-exchange chromatography was carried out next after dialyzing the hydrophobic chromatography fraction by MOPS buffer. The column used was a RESOURCE Q 1 mL (GE Health Care), the flow rate was 1 mL/min, the fraction size was 1 mL/tube, and elution was performed by creating an NaCl concentration gradient from 0 M to 0.5 M at a flow rate of 20 mL using 20 mM MOPS buffer (pH 7.0). The instrument used was an AKTA purifier (GE Health Care).

Finally, gel filtration chromatography was conducted. The column used was a TSK-Gel G3000SW (column size 21.5 mmL diameter×30 cm, manufactured by Tosoh Corp.), flow rate 1 mL/min, fraction size 1 mL/tube, eluted by 0.02 M KPB (pH 7.0) containing 0.3 M NaCl. MW-Marker (trade name) manufactured by Oriental Yeast Co., Ltd. was used as a molecular weight marker. An HPLC manufactured by Shimadzu was used as the instrument used.

The protein concentration in the enzyme solution was measured by the Bradford method. Protein Assay Reagent (Bio-Rad) was used as the protein assay reagent, and bovine serum albumin (BSA) was used as the standard. *B. terrae* strain AKC-020 was cultured in medium containing DOI to cause it to express DOI reductase. As a result of culture, 0.3 g of cells (wet weight) was obtained in 100 mL of medium. The total activity relative to DOI was 78.7 U. Table 7 and FIG. 2 show the results of purification and results of SDS-PAGE, respectively, when DOI reductase was purified by the ammonium sulfate fractionation, Butyl-Toyopearl 650M, Resource Q, and TSK-Gel G3000SW.

TABLE 7

Purification of DOI reductase from *Burkholderia terrae* strain AKC-020

| Purification sample | Total activity (U) | Protein (mg) | Fluid volume (mL) | Recovery rate (%) | Degree of purification (-fold) |
|---|---|---|---|---|---|
| Crude enzyme solution | 78.7 | 37.6 | 25 | 100.0 | 1.0 |
| Ammonium sulfate precipitate fraction | 74.7 | 18.55 | 35 | 95.0 | 1.9 |
| Butyl-Toyopearl 650M | 15.8 | 0.40 | 5 | 20.1 | 18.9 |
| Resoure Q | 11.2 | 0.24 | 1 | 14.2 | 22.3 |
| Gel filtration | 3.6 | 0.07 | 3 | 4.5 | 24.6 |

The retention time of the purified enzyme was 76.66 minutes based on the results of gel filtration chromatography using a TSK-Gel G3000SW column. The retention times of the MW-Marker (equine myocardial cytochrome c (molecular weight 12,400)), yeast myokinase (molecular weight 32,000), yeast enolase (molecular weight 67,000), porcine myocardial lactate dehydrogenase (molecular weight 142,000), and yeast glutamate dehydrogenase (molecular weight 290,000) under the same HPLC conditions were 105.44, 94.89, 86.40, 76.70, and 65.01 minutes, respectively. Therefore, the purified enzyme in aqueous solution was identified to have a molecular mass of approximately 130 kDa. On the other hand, this enzyme was assumed to be a homotetramer since the molecular mass of the monomer was approximately 36 kDa by SDS-PAGE (FIG. 2).

5. Properties of Purified DOI Reductase (1) Optimum pH

Figure 3:
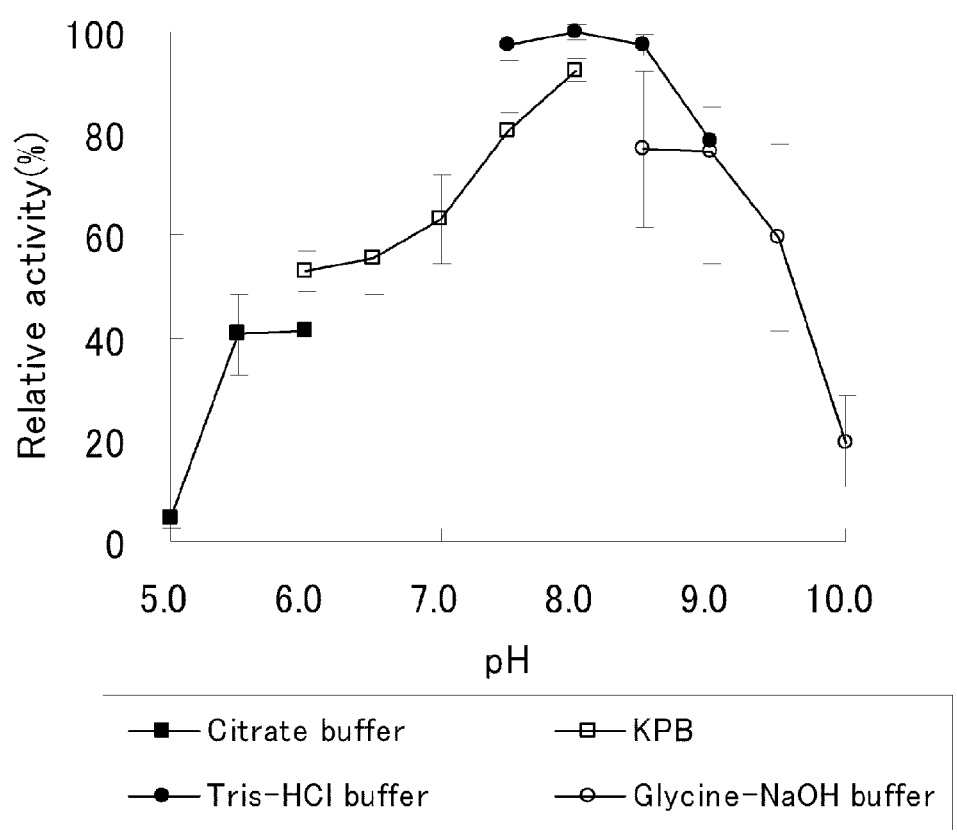
FIG. 3 A graph showing the optimum pH of the DOI reductase of the present invention. The horizontal axis shows the pH; the vertical axis shows the relative activity taking the rate of decrease in absorbance (340 nm) as the indicator. In the graph, the black squares show citrate buffer, the white squares show potassium phosphate buffer (abbreviated hereinafter as "KPB"), the black circles show Tris-hydrochloride buffer, and the white circles show glycine-sodium hydroxide buffer. The vertical bars represent the standard deviation.
Figure 6:
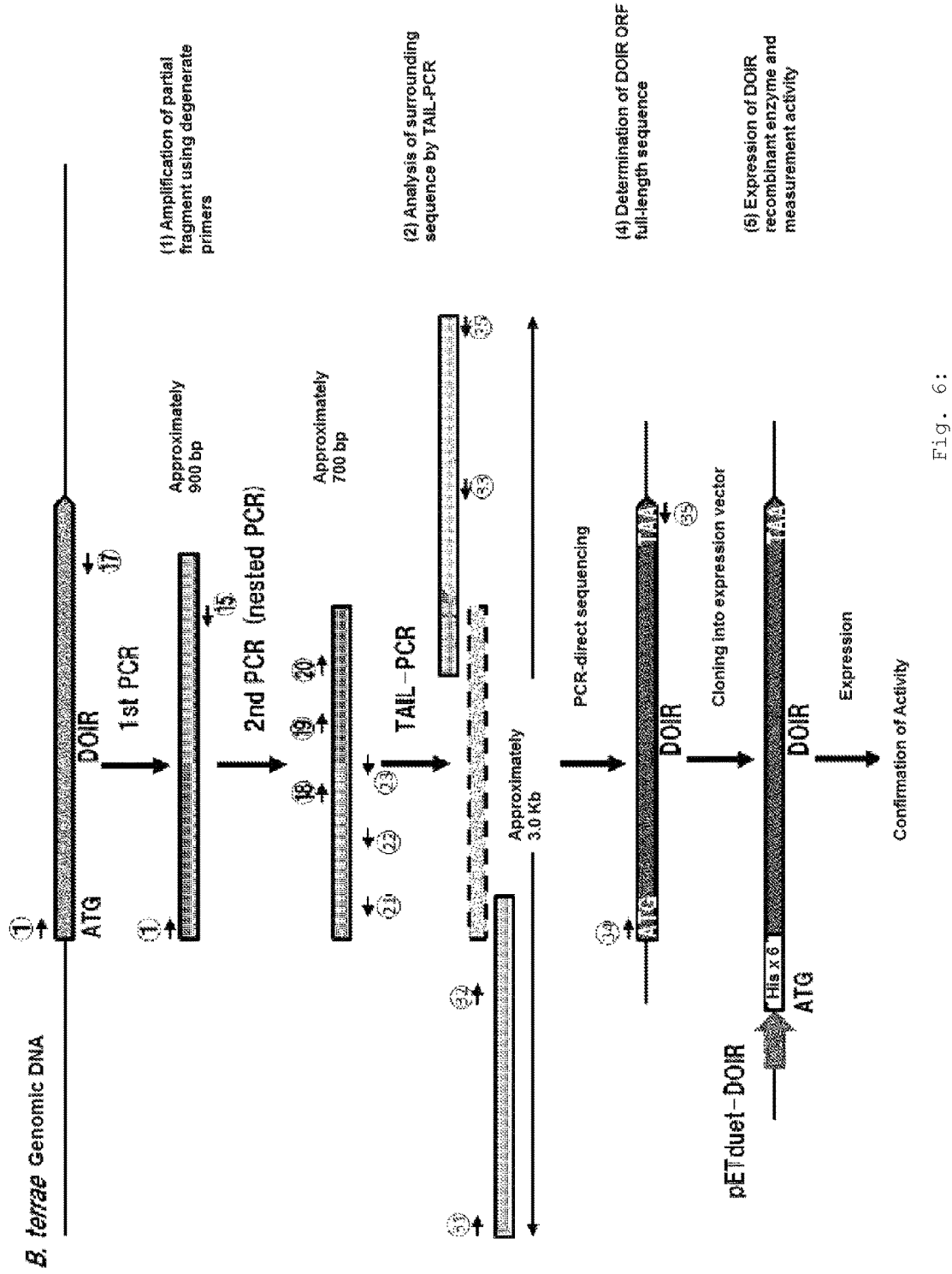
FIG. 6 is a scheme showing an overview of cloning of the DOI reductase gene of the present invention.

The reduction of DOI was measured by assaying the amount of coenzyme NADH converted into $NAD^+$ by spectrophotometer. A quantity of 10 µL of enzyme solution was added to 980 µL of 0.1 M buffer of each pH containing 0.3 µmol of NADH and prewarmed for five minutes at 25° C. A quantity of 10 µL of 0.1 M DOI was added and mixed immediately. The rate of decrease in the absorbance (wavelength 340 nm) over two minutes was measured by spectrophotometer, and the activity was compared at each pH. FIG. 3 shows the results.

(2) Substrate Specificity

The substrate specificity of DOI when moving in the opposite direction from the reduction reaction was measured by assaying the amount of coenzyme $NAD^+$ converted into NADH by spectrophotometer. A quantity of 10 µL of enzyme solution was added to 980 µL of 0.1 M buffer containing 1.0 µmol of $NAD^+$ and prewarmed for five minutes at 25° C. A quantity of 10 µL of each 0.1 M substrate was added and mixed immediately. The rate of increase in the absorbance (wavelength 340 nm) over two minutes was measured by spectrophotometer, and the activity by each substrate was compared. The amount that converts 1 µmol of NADH in one minute was defined as 1 unit (U), taking the molecular extinction coefficient of NADH at a wavelength of 340 nm to be 6.22 $mM^{-1}$ $cm^{-1}$. The results are shown in Table 8. In the table, N.D. means that no reaction could be detected.

TABLE 8

Substrate specificity (oxidation reaction)

| Substrate (5 mM) | U/mg | |
| --- | --- | --- |
| | pH 8.0 | pH 9.0 |
| Myo-inositol | 3.21 | 5.71 |
| (−)-vibo-quercitol | 8.21 | 13.93 |
| D-glucose | N.D. | N.D. |
| D-xylose | N.D. | N.D. |
| Cyclohexanol | N.D. | N.D. |
| Sorbitol | N.D. | N.D. |
| Trans-1,2-cyclohexanediol | N.D. | N.D. |
| 1,3-Cyclohexanediol | N.D. | N.D. |
| 1,2,3-Cyclohexanetriol (cis-, trans-mixture) | N.D. | N.D. |
| 2-Propanol (0.1M) | N.D. | N.D. |
| 1,2-Propanediol (0.1M) | N.D. | N.D. |

(3) Km Value and Vmax

The enzymatic activity was measured by assaying the amount of coenzyme NADH or NAD$^+$ changed by spectrophotometer. The amount that converts 1 μmol of NADH in one minute was defined as 1 unit (U), taking the molecular extinction coefficient of NADH at a wavelength of 340 nm to be 6.22 mM$^{-1}$ cm$^{-1}$. The protein concentration of the enzyme solution was also measured by the Bradford method. The activity was measured at substrate concentrations of 0.02, 0.04, 0.06, 0.08, 0.1, 0.2, 0.3, 1.0, and 2.0 mM, and the Km value and Vmax relative to NADH were calculated. The activity was also measured at coenzyme concentrations of 0.04, 0.06, 0.08, 0.1, and 0.2 mM, and the Km value relative to NADH was calculated. The activity was also measured at quercitol concentrations of 1.0, 2.0, 3.0, 4.0, and 5.0 mM, and the Km value and Vmax relative to quercitol were calculated. Similarly, the activity was measured at NAD$^+$ concentrations from 0.02 mM to 0.04, 0.06, 0.1, 0.2, and 0.3 mM, and the Km value relative to NAD$^+$ was calculated. The results are shown in Table 9.

TABLE 9

Dynamic parameters

| | |
| --- | --- |
| Km and V$_{max}$ to DOI | 0.41 mM, 116.28 U/mg |
| Km to NADH | 0.04 mM (0.1M Tris-HCl, pH 8.0) |
| Km and V$_{max}$ to (−)-vibo-quercitol | 1.60 mM, 16.45 U/mg |
| Km to NAD$^+$ | 0.11 mM (0.1M Gly-NaOH, pH 9.0) |

6. Cloning the DOI Reductase Gene (DOIR Gene)

Figure 4:
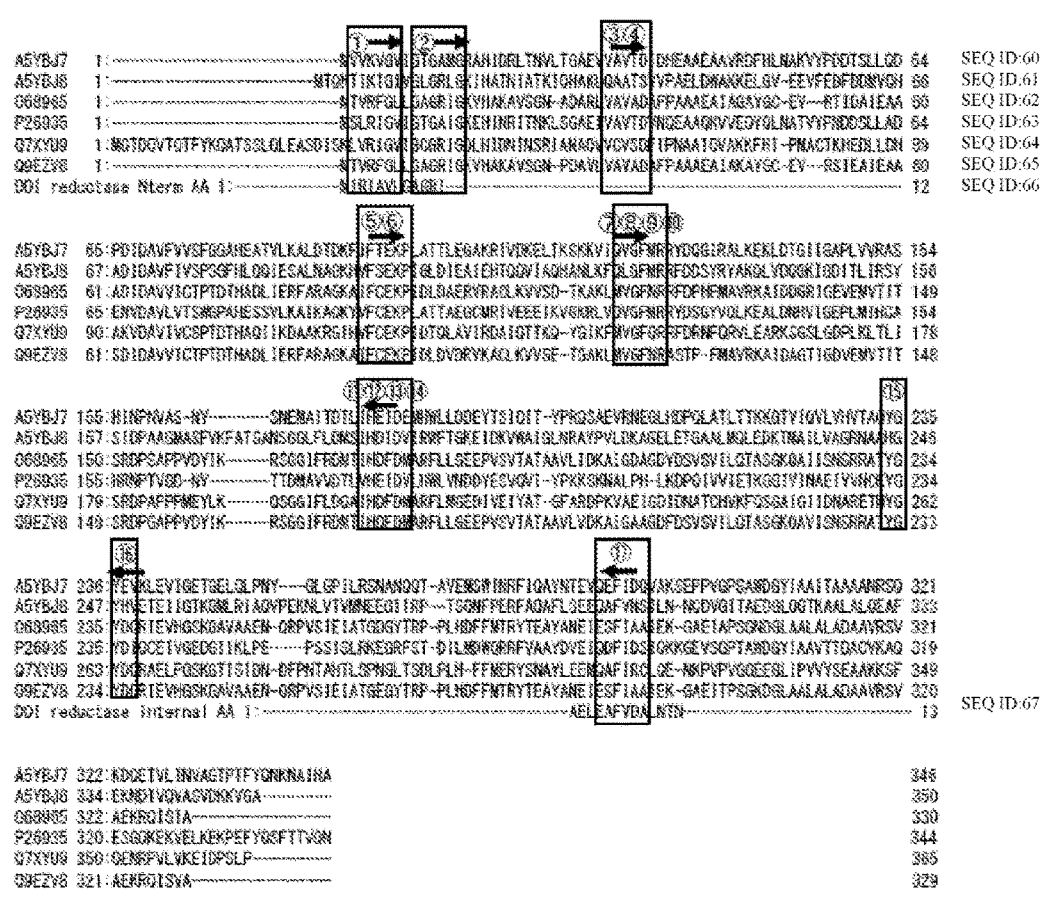

Amino acid sequences of known enzymes reported in the literature to have inositol dehydrogenase (IDH) activity were acquired from a database. A total of eight degenerate primer design regions were selected from regions having high homology with these amino acid sequences and the N-terminal amino acid sequence and internal amino acid sequence of DOIR. Table 10 and FIG. 4 show the alignments and degenerate primer sequences produced. Table 11 and FIG. 5 show the PCR conditions.

To explain in greater detail, a first PCR (gradient PCR having an annealing temperature condition in the 45-60° C. range) was conducted using the degenerate primers designed as described above with genomic DNA extracted from B. terrae strain AKC-020 as the template. As a result of conducting PCR by various primer combinations, amplification of an approximately 900 bp band was able to be confirmed at an annealing temperature of about 60° C. by a DOIRdgF1/DOIRdgR8 primer set ((1) and (17) in Table 10 and FIG. 4). Using this amplified fragment as a template, the amplified fragment was refined by a second PCR (nested PCR) using internal region primers. As a result, an approximately 700 bp fragment was amplified in the DOIRdgF1/DOIRdgR7Q primer set ((1) and (15) in Table 10 and FIG. 4), and the amino acid sequence encoding this base sequence was shown to have homology of about 34-53% with known IDH amino acid sequences.

Primers ((18)-(23)) were therefore produced based on the sequence information of the partial fragments of the DOIR gene acquired, and TAIL-PCR (thermal asymmetric interlaced PCR) was conducted (these primers are also shown in Table 10). Furthermore, PCR products containing the sequences of the downstream region and upstream region, respectively, were obtained by TAIL-PCR using (18)-(20) as forward primers and (25) as a reverse primer to clone the downstream region and by TAIL-PCR using (31) as a forward primer and (21)-(23) as reverse primers. An approximately 3.0 kb base sequence containing an ORF of DOIR could be conjectured from the base sequence information thereof. Primers ((32) and (33) in Table 10 and FIG. 4) were produced using the sequence of positions approximately 150 bp upstream and approximately 70 bp downstream of the DOIR gene ORF, and an approximately 1.2 kb region containing the total ORF length of the DOIR gene was amplified. This amplified fragment was purified, and the DOIR gene sequence was finalized by direct sequencing.

TABLE 10

Table 10: Summary of primers used

| No. | Name | Sequence (5'-3') | Other |
| --- | --- | --- | --- |
| Degenerate primers | | | |
| (1) | DIORdgnF1 | ATGATHMGNATHGCNGT (SEQ ID NO: 25) | Fragment acquired by 1$^{st}$ and 2$^{nd}$ PCR |
| (2) | DIORdgnF2 | GGNGCNGGNMGNATHGG (SEQ ID NO: 26) | |
| (3) | DIORdgnF3T | GTNGCNGTNACNGA (SEQ ID NO: 27) | |
| (4) | DIORdgnF3A | GTNGCNGTNGCNGA (SEQ ID NO: 28) | |
| (5) | DIORdgnF4I | TTYTGYGARAARCCNAT (SEQ ID NO: 29) | |
| (6) | DIORdgnF4L | TTYTGYGARAARCCNYT (SEQ ID NO: 30) | |
| (7) | DIORdgnF5QN | CARGTNGGNTTYAAYMG (SEQ ID NO: 31) | |
| (8) | DIORdgnF5QM | CARGTNGGNTTYATGMG (SEQ ID NO: 32) | |
| (9) | DIORdgnF5MN | ATGGTNGGNTTYAAYMG (SEQ ID NO: 33) | |
| (10) | DIORdgnF5MM | ATGGTNGGNTTYATGMG (SEQ ID NO: 34) | |
| (11) | DIORdgnR6FM | CATRTCRAARTCRTGDAT (SEQ ID NO: 35) | |
| (12) | DIORdgnR6FV | ACRTCRAARTCRTGDAT (SEQ ID NO: 36) | |

TABLE 10-continued

Table 10: Summary of primers used

| No. | Name | Sequence (5'-3') | Other |
|---|---|---|---|
| (13) | DIORdgnR6IM | CATRTCDATRTCRTGDAT (SEQ ID NO: 37) | |
| (14) | DIORdgnR6IV | ACRTCDATRTCRTGDAT (SEQ ID NO: 38) | |
| (15) | DIORdgnR7Q | DKYTGRTCRTANCCRTA (SEQ ID NO: 39) | Fragment acquired by $2^{nd}$ PCR |
| (16) | DIORdgnR7V | CKNACRTCRTANCCRTA (SEQ ID NO: 40) | |
| (17) | DIORdgnR8 | GCRTCNACRAANGCYTC (SEQ ID NO: 41) | Fragment acquired by $1^{st}$ PCR |

TAIL-PCR gene specific primers

| (18) | DOIRtailF1 | TCGACATGGAAAAGTCGCTTGC (SEQ ID NO: 42) | |
|---|---|---|---|
| (19) | DOIRtailF2 | TGCCTCCGCGTGACTATGT (SEQ ID NO: 43) | |
| (20) | DOIRtailF3 | TGACCGACTTCGATACGGTGAT (SEQ ID NO: 44) | |
| (21) | DOIRtailR1 | TCAATCGCGTTGCGGAATGC (SEQ ID NO: 45) | |
| (22) | DOIRtailF2 | TTCTCACACAGAACAGCCTTGC (SEQ ID NO: 46) | |
| (23) | DOIRtailR3 | TAGCCAACGATTTTGCTGCACT (SEQ ID NO: 47) | |

TAIL-PCR advanced primers

| (24) | TAIL-AD1 | NTCGASTWTSGWGTT (SEQ ID NO: 48) | |
|---|---|---|---|
| (25) | TAIL-AD2 | NGTCGASWGANAWGAA (SEQ ID NO: 49) | Acquisition of downstream region |
| (26) | TAIL-AD3 | WGTGNAGWANCANAGA (SEQ ID NO: 50) | |
| (27) | TAIL-AD4 | WGCNAGTNAGWANAAG (SEQ ID NO: 51) | |
| (28) | TAIL-AD5 | AWGCANGNCWGANATA (SEQ ID NO: 52) | |
| (29) | TAIL-AD6 | GTNCGASWCANAWGTT (SEQ ID NO: 53) | |
| (30) | TAIL-AD7 | AGWGNAGWANCAWAGG (SEQ ID NO: 54) | |
| (31) | TAIL-AD8 | GTCGASWGANAWGAAN (SEQ ID NO: 55) | Acquisition of upstream region |

Primers for acquisition of DOIR full-length sequence

| (32) | DOIRtopF2 | tacggcgtggaactcatc (SEQ ID NO: 56) | |
|---|---|---|---|
| (33) | DOIRbotR2 | tgagtgataccaagacatgcc (SEQ ID NO: 57) | |

Primers for constructing DOIR expression construct

| (34) | DOIRexF1Bam | agaggatccaATGATTCGAATCGCCGTACT (SEQ ID NO: 58) | Added at BamHI site |
|---|---|---|---|
| (35) | DOIRexR1Hind | agagaagcttCACCTTGACGGCTTTGC (SEQ ID NO:59) | Added at HindIII site |

Definition of nucleotides: R: G or A, Y: T or C, M: A or C, K: G or T, S: G or C, W: A or T, H: not G, D: not C, N: any

TABLE 11

PCR combinations by degenerate primers

| Final concentration | Composition |
|---|---|
| 100 ng | Genomic DNA (3-fold diluted PCR sample of 10) |
| 2 mM | Forward primer |
| 2 mM | Reverse primer |
| 1x | KOD Fx Neo Buffer |
| 4 mM | dNTP |
| 1 U | KOD Fx Neo |

Up to 0.05 mL with distilled water

7. Homology of DOIR Gene and Known Genes

The DOIR gene had a total length of 990 bp and an ORF comprising 330 amino acid residues (SEQ ID NOS: 1 and 2). The molecular weight estimated from the amino acid sequence was 36195.12, and the amino acid sequence contained an N-terminal "MIRIAVLGAGRI" (SEQ ID NO: 66) and internal amino acid sequence "AELEAFVDALNTN" (SEQ ID NO: 67) obtained from sequence analysis of the purified enzyme. The DOIR amino acid sequence was understood to be an example having homology of approximately 80% with inositol 2-dehydrogenase (IDH) from certain types of microorganisms as a result of a BLAST homology search (using UniProtKB/SwissProt as the database searched). However, the majority of these known sequences are classified as IDH based on the homology of the amino acid sequence; only those shown in Table 12 are actually reported to have IDH activity.

TABLE 12

Homology of amino acid sequences of DOIR and inositol dehydrogenases

| Enzyme name | Strain | UniProtKB Accession no. | Identity (%) | |
|---|---|---|---|---|
| IdhA | Sinorhizobium melilot 1021 | O68965 | 49.5 | Galbraith M. P. et al. |
| IdhA | Sinorhizobium fredii USDA191 | Q9EZV8 | 48.9 | Guoqiao J. et al. |
| IolG | Lactobacillus casei BL23 | A5YBJ7 | 24.3 | Yebra M. J. et al. |
| IolG | Bacillus subtilis 168 | P26935 | 24.0 | Fujita Y. et al. |

8. Construction of an Expression Vector pETduet-DOIR

Figure 7:
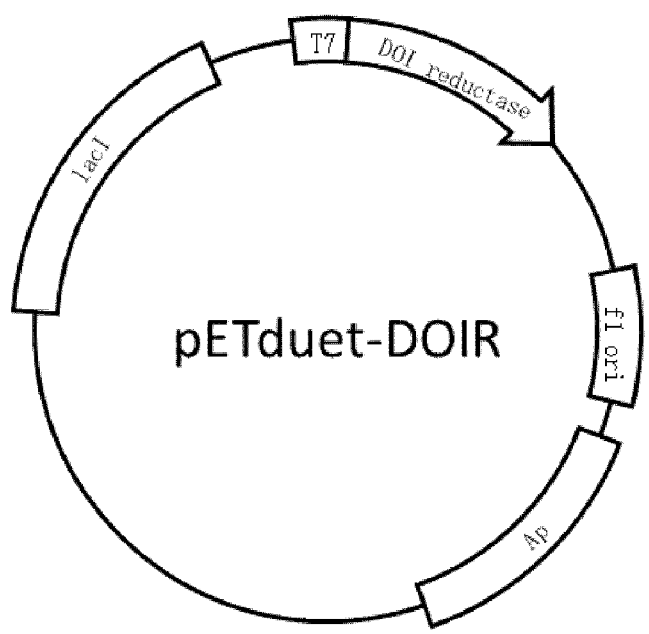
FIG. 7 shows the structure of an expression vector of the DOI reductase gene of the present invention.

A DOIR expression vector pETduet-DOIR was constructed for the expression of DOIR in a heterologous host by E. coli (FIG. 7). The DOIR gene of strain AKC-020 was amplified using primers (34) and (35), and pETDuet-1 (Merck) was cloned into the respective restriction enzyme-recognition sites using the restriction enzymes BamHI and HindIII (see Table 10 above). pETduet-DOIR was transformed into E. coli BL21 (DE3).

As a result of conducting a BLAST search as described above, multiple inositol 2-dehydrogenases showing homology with the DOIR of strain AKCO-020 were judged to exist. These inositol 2-dehydrogenase genes were therefore synthesized and expressed by the same method as the DOIR gene above to investigate whether these inositol 2-dehydrogenases catalyze DOI reduction. Specifically, six inositol dehydrogenases showing homology of approximately 80%, 70%, 60%, 50%, 40%, and 30% by a BLASTP search with the amino acid sequence of DOIR (using GenBank, PDB, and SwissProt as the databases searched) were selected (see Table 13).

In the start codon of Bs-iolX, ATF was changed for GTG when synthesizing the genes shown in Table 13. Furthermore, inositol dehydrogenase (Sf-Idh) from Sinorhizobium fredii USDA191 is an enzyme that oxidizes myo-inositol, and iolX (Bs-IolX) from Bacillus subtilis 168 is reported to encode an enzyme showing activity on scyllo-inositol. In addition, iolW (Bs-IolW) is said to be an NADPH-dependent inositol dehydrogenase. These six genes were introduced into an expression vector Pet21B(+) (Merck), and expressed by E. coli BL21 (DE3). Table 14 shows their respective activities relative to the culture broth.

TABLE 14

DOI reducing activity of various inositol dehydrogenases/DOIR

| Host | Vector | U/Ml culture |
|---|---|---|
| E. coli BL21 (DE3) | PETDuet-DOIR | 11.2 |
| | pET21b-Bh-IolG | 11.7 |
| | pET21b-Pa-Idh | 8.4 |
| | pET21b-Ps-Idh | 9.8 |
| | pET21b-Sf-Idh | 0.45 |
| | pET21b-BS-IolX | 0.13 |
| | pET21b-BS-IolW | 0.69 (using NADPH as coenzyme) |
| | pET21b(+) | ND |

ND: Below detection limit

Figure 12:
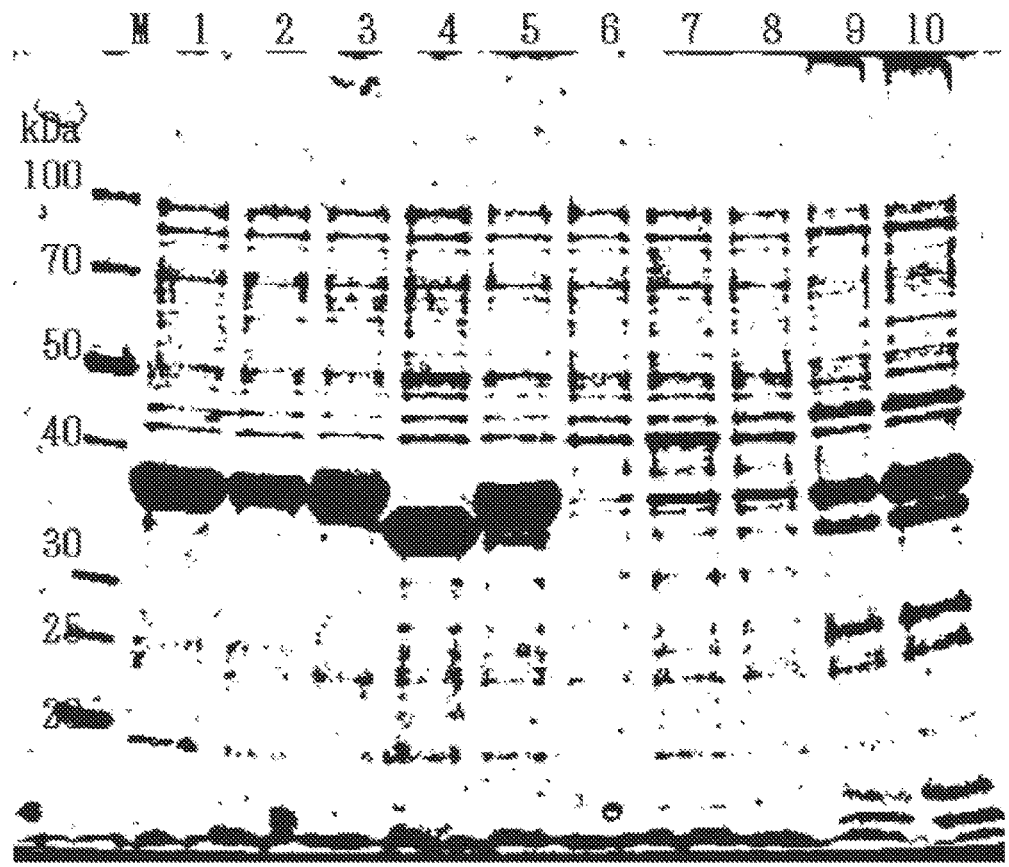
FIG. 12 is a photograph showing the results of SDS-PAGE of a recombinantly-produced enzyme.

The expression of recombinant proteins of DOIR and Bh-IolG, Pa-Idh, Ps-Idh, and Sf-Idh was confirmed by SDS-PAGE. When the expression levels were compared based on the bands in the gel using an ImageJ 1.46, the expression levels of Bh-IolG, Pa-Idh, Ps-Idh, and Sf-Idh relative to DOIR were 0.61, 0.99, 1.25, and 0.97 times (FIG. 12). These presented activity on DOI (Table 14).

Table 15 shows the DOI conversion rates and diastereomer excesses of the products. DOIR and Bh-IolG, Pa-Idh, and Ps-Idh converted DOI to (−)-vibo-quercitol at a diastereomer excess of 89% d.e. or greater.

TABLE 13

Inositol dehydrogenases the activity of which was measured

| Enzyme name | No. of amino acids | Molecular weight | Accession (protein) | Strain | Homology with DOIR (%) |
|---|---|---|---|---|---|
| BH-IolG | 330 | 36,308.11 | EDS70356.1 | Burkholderia sp. SJ98 | 79 |
| Pa-Idh | 329 | 36,160.26 | AD072508.1 | Pantoea sp. At-9b | 58 |
| Ps-Idh | 334 | 36,618.38 | EIK69154.1 | Pseudomonas synxantha BG33R | 68 |
| Sf-Idh | 329 | 34,648.16 | AAG44816.1 | Sinorhizobium fredii | 50 |
| Bs-IolX | 342 | 37,482.98 | CAB12924.1 | Bacillus subtilis subsp. Subtilis str. 168 | 36 |
| Bs-IolW | 359 | 40,226.62 | CAB15358 | Bacillus subtilis subsp. Subtilis str. 168 | 27 |

Bs-IolX converted DOI to scyllo-quercitol at a diastereomer excess of 99%. Sf-Idh presented weak reduction of DOI relative to the culture broth. An excess of sonicated cell solution was added, but the product quercitol could not be detected.

TABLE 15

Conversion to quercitol (from recombinant E. coli)

| Enzyme name | (−)-Vibo-quercitol (mM) | Remaining DOI (mM) | Conversion rate | Diastereomer excess (% d.e.) |
|---|---|---|---|---|
| DOIR | 9.9 | N.D. | ≥99% | 89.0 |
| Bh-IolG | 9.9 | N.D. | ≥99% | 90.3 |
| Pa-Idh | 9.9 | N.D. | ≥99% | 89.1 |
| Ps-Idh | 9.9 | N.D. | ≥99% | 90.8 |
| Sf-Idh | N.D. | 9.9 | — | — |

TABLE 15-continued

Conversion to quercitol (from recombinant E. coli)

| Enzyme name | (−)-Vibo-quercitol (mM) | Remaining DOI (mM) | Conversion rate | Diastereomer excess (% d.e.) |
|---|---|---|---|---|
| BS-IolX | 9.6* | 0.4 | 96% | ≥99% |
| BS-IolW | N.D. | 9.9 | — | — |

*(however, converted into scyllo-quercitol.)
ND: below detection limit

INDUSTRIAL APPLICABILITY

The present invention can be utilized in the industrial fermentation production of (−)-vibo-quercitol very simply, efficiently, and at high purity.

The invention claimed is:

1. A method of producing (−)-vibo-quercitol, the method comprising
   contacting 2-deoxy-scyllo-inosose with an isolated enzyme comprising a protein of (a) or (b):
   (a) a protein comprising the amino acid sequence of SEQ ID NO: 2, 4, 6 or 8; or
   (b) a protein comprising an amino acid sequence having 85% or greater identity to the amino acid sequence of SEQ ID NO: 2, 4, 6 or 8 and having 2-deoxy-scyllo-inosose reductase activity, and
   reacting under conditions of pH 5.0-10.0.

2. The method according to claim 1, wherein the isolated enzyme comprises:
   (a) the protein comprising the amino acid sequence of SEQ ID NO: 2; or
   (b) the protein comprising an amino acid sequence having 85% or greater identity to the amino acid sequence of SEQ ID NO: 2 and having 2-deoxy-scyllo-inosose reductase activity.

3. The method according to claim 1, wherein the isolated enzyme comprises:
   (a) the protein comprising the amino acid sequence of SEQ ID NO: 6; or
   (b) the protein comprising an amino acid sequence having 85% or greater identity to the amino acid sequence of SEQ ID NO: 6 and having 2-deoxy-scyllo-inosose reductase activity.

4. The method according to claim 1, wherein the isolated enzyme comprises:
   (a) the protein comprising the amino acid sequence of SEQ ID NO: 8; or (b) the protein comprising an amino acid sequence having 85% or greater identity to the amino acid sequence of SEQ ID NO: 8 and having 2-deoxy-scyllo-inosose reductase activity.

5. The method according to claim 1, wherein the isolated enzyme comprises (a) the protein comprising the amino acid sequence of SEQ ID NO: 2, 4, 6 or 8.

6. The method according to claim 1, wherein the isolated enzyme comprises:
(a) the protein comprising the amino acid sequence of SEQ ID NO: 4; or
(b) the protein comprising an amino acid sequence having 85% or greater identity to the amino acid sequence of SEQ ID NO: 4 and having 2-deoxy-scyllo-inosose reductase activity.

7. The method according to claim 1, further comprising culturing a transformant for (−)-vibo-quercitol conversion comprising a gene encoding the protein of (a) or (b) for a time and under conditions to produce the isolated enzyme, and
purifying and recovering the isolated enzyme from the culture.

8. A recombinant vector for (−)-vibo-quercitol conversion including a gene encoding a protein of (a) or (b) below:
(a) a protein comprising the amino acid sequence of SEQ ID NO: 2; or
(b) a protein comprising an amino acid sequence having 85% or greater identity to the amino acid sequence of SEQ ID NO: 2 and having 2-deoxy-scyllo-inosose reductase activity.

9. The recombinant vector according to claim 8, wherein the gene encodes (a) the protein comprising the amino acid sequence of SEQ ID NO: 2.

10. A transformant for (−)-vibo-quercitol conversion comprising the recombinant vector of claim 8 introduced.

11. A transformant for (−)-vibo-quercitol conversion comprising a gene encoding a protein of (a) or (b) below:
(a) a protein comprising the amino acid sequence of SEQ ID NO: 2; or
(b) a protein comprising an amino acid sequence having 85% or greater identity to the amino add sequence of SEQ ID NO: 2 and having 2-deoxy-scyllo-inosose reductase activity.

12. The transformant according to claim 11, wherein the gene encodes (a) the protein comprising the amino acid sequence of SEQ ID NO: 2.

13. A method of producing 2-deoxy-scyllo-inosose reductase, comprising
culturing the transformant of claim 11 for a time and under conditions suited to the production of a protein having 2-deoxy-scyllo-inosose reductase activity, and purifying and recovering the protein from the culture.

14. A recombinant vector for (−)-vibo-quercitol conversion comprising a nucleotide sequence of (a) or (b) below:
(a) the nucleotide sequence of SEQ ID NO: 1; or
(b) a nucleotide sequence (i) comprising a nucleotide sequence having 85% or greater identity to the nucleotide sequence of SEQ ID NO: 1, (ii) hybridizing under stringent conditions with DNA comprising a sequence complementary to the nucleotide sequence of SEQ ID NO: 1, and (iii) encoding a protein having 2-deoxy-scyllo-inosose reductase activity,
wherein said stringent conditions comprises hybridizing at a constant temperature of 65° C. for 8-16 hours in a solution containing 6×SSC (composition of 1×SSC: 0.15 M sodium chloride, 0.015 M sodium citrate, pH 7.0 ), 0.5% SDS, 5× Denhardt's solution, and 100 mg/mL of herring sperm DNA, and washing by 2×SSC and 0.1% SDS at 68° C.

15. A transformant for (−)-vibo-quercitol conversion comprising a nucleotide sequence of (a) or (b) below:
(a) the nucleotide sequence of SEQ ID NO: 1; or
(b) a nucleotide sequence (i) comprising a nucleotide sequence having 85% or greater identity to the nucleotide sequence of SEQ ID NO: 1, (ii) hybridizing under stringent conditions with DNA comprising a sequence complementary to the nucleotide sequence of SEQ ID NO: 1, and (iii) encoding a protein having 2-deoxy-scyllo-inosose reductase activity,
wherein said stringent conditions comprises hybridizing at a constant temperature of 65° C. for 8 -16 hours in a solution containing 6×SSC (composition of 1×SSC: 0.15 M sodium chloride, 0.015 M sodium citrate, pH 7.0), 0.5% SDS, 5× Denhardt's solution, and 100 mg/mL of herring sperm DNA, and washing by 2×SSC and 0.1% SDS at 68° C.

16. A method of producing 2-deoxy-scyllo-inosose reductase, comprising
culturing the transformant of claim 15 for a time and under conditions suited to the production of a protein having 2-deoxy-scyllo-inosose reductase activity, and purifying and recovering the protein from the culture.

* * * * *